(12) United States Patent
Norman et al.

(10) Patent No.: US 8,703,103 B2
(45) Date of Patent: *Apr. 22, 2014

(54) VOLATILE IMIDAZOLES AND GROUP 2 IMIDAZOLE BASED METAL PRECURSORS

(75) Inventors: John Anthony Thomas Norman, Encinitas, CA (US); Melanie K. Perez, San Diego, CA (US); Moo-Sung Kim, Gyunggi-Do (KR)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/016,127

(22) Filed: Jan. 28, 2011

(65) Prior Publication Data
US 2012/0035351 A1    Feb. 9, 2012

Related U.S. Application Data

(60) Provisional application No. 61/301,824, filed on Feb. 5, 2010, provisional application No. 61/369,448, filed on Jul. 30, 2010.

(51) Int. Cl.
*A61B 5/055*     (2006.01)

(52) U.S. Cl.
USPC .......... 424/9.365; 534/10; 438/681; 540/477; 540/579; 544/333; 546/63; 546/272.7; 548/303.1; 548/312.4; 548/314.4; 548/314.7; 548/315.4; 548/335.1; 548/107; 117/104

(58) Field of Classification Search
None
See application file for complete search history.

(56) References Cited

U.S. PATENT DOCUMENTS

| 4,719,309 A * | 1/1988 | Mesch ...................... 548/335.1 |
| 5,319,118 A | 6/1994 | Norman et al. |
| 2005/0132959 A1 * | 6/2005 | Bauch et al. .................. 118/667 |
| 2008/0242880 A1 | 10/2008 | Chen et al. |
| 2009/0171098 A1 * | 7/2009 | Bara et al. .................. 548/335.1 |
| 2009/0200524 A1 * | 8/2009 | Thompson et al. ....... 252/519.21 |
| 2012/0028846 A1 * | 2/2012 | Yaghi et al. ...................... 506/39 |

FOREIGN PATENT DOCUMENTS

| JP | 48-019291 | | 6/1973 |
| JP | 02-083372 | | 3/1990 |
| JP | 05255336 A | * | 10/1993 |
| JP | 2000-206735 | | 7/2000 |
| JP | 2002-148864 A | | 5/2002 |
| JP | 2011-001362 | | 1/2011 |
| JP | 2011-080144 | | 4/2011 |
| WO | 2009/094259 A1 | | 7/2009 |
| WO | 2009086263 A1 | | 7/2009 |

OTHER PUBLICATIONS

Schumann et al. Chem. Commun. 1999. 2091-2092.*
Tang et al. JACS. 1978, 3918-3922.*
Hitzbleck et al. Inorg. Chem. 2006, 10329-10337.*
J. A. T. Norman, et al., Volatile Barium, Strontium and Calcium Bis(hexafluoroacetylacetonate) (crown ether) Complexes, J. Chem. Soc., Chem. Commun., (1991) p. 971-972.
Sjoerd Harder, et al., Homoleptic B-Diketiminato Complexes of the Alkaline-Earth Metals: Trends in the Series Mg, Ca, Sr, and Ba, Organometallics (2002), 21, 3782-3787.
Hani M. El-Kaderi, et al., Sandwich Complexes of the Heavier Alkaline Earth Metals Containing B-Diketiminato Ligand Sets, Organometallics 2004, 23 (21), 4995-5002.
Mark J. Saly, et al., Volatility, High Thermal Stability, and Low Melting Points in Heavier Alkaline Earth Metal Complexes Containing Tris(pyrazolyl)borate Ligands, (Web): Apr. 27, 2009.
Baburam Sedai, et al., Volatility Enhancement in Calcium, Strontium, and Barium Complexes Containing B-Diketiminate Ligands with Dimethylamino Groups on the Ligand Core Nitrogen Atoms, Organometallis 2009, 28, 1032-1038.
Timo Hatanpaa, et al., Synthesis and Characterisation of Cyclopentadienyl Complexes of Barium: Precursors for Atomic Layer Deposition of BaTiO3, Dalton Trans., (2004) p. 1181-1188.
Jie-Peng Zhang, et al., Crystal Engineering of Binary Metal Imidazolate and Triazolate Frameworks, Chem. Commun., 2006, p. 1689-1699.
Hayley A. Every, et al., Substituted Imidazoles as Proton Transport Facilitators in Fuel Cell Membranes, Electrochemical Society Proceedings vol. 2004-21, p. 277-286.
Palaniandavar, M., et al; "Copper(II)-Dusulphide Interaction: A Spectroscopic and Electrochemical Study of the Interatction of Copper(II) with an Imidazole-Containing Disulphide"; Transition Metal Chemistry; vol. 19, No. 4; 1994; pp. 439-441; XP-002630382.
Moreno-Vida, M.I., et al.; "Bromopalladates(II) of Xanthine Derivatives. Crystal Structure of 1,3,8-Trimethylxanthininium Tribromopalladte(II) Monohydrate"; Inorganica Chimica ACTA; vol. 157, No. 2; 1989; pp. 201-207; XP-002630383.
Baumann, G.C., et al; "Preparation of a New Ligand Containing Disulfide and Imidazole Donor Groups. Structure of Dibromo[5-(1,2,5-Dithiazepan-5-Ylmethylene)-4-Methyl-2-Ethylimidzole]Cadmium(II). Cadmium-113 and Carbon-13 NMR Studies of Complex Formation"; Inorganic Chemistry; vol. 23, No. 20; 1984; pp. 3104-3108; XP-002630384.
Bernarducci,E.E., et al.; "Molecular Structures, Electronic Spectra, and ESR Spectra of Bis(4,4', 5,5'-Tetramethyl-2,2'-Biimidazole)Copper(II) Dinitrate and Bis(4,4' ,5,5'-Tetramethyl-2,2'-Biimidazole)Zinc(II)0.90Copper(II) 0.10 Dinitrate"; Inorganic Chemistry; vol. 22; 1983; pp. 3911-3920; XP-002630385.

(Continued)

*Primary Examiner* — Michael G Hartley
*Assistant Examiner* — Sean R Donohue
(74) *Attorney, Agent, or Firm* — Geoffrey L. Chase; Joseph D. Rossi

(57) ABSTRACT

Sterically hindered imidazole ligands are described, along with their synthesis, which are capable of coordinating to Group 2 metals, such as: calcium, magnesium, strontium, in an eta-5 coordination mode which permits the formation of monomeric or dimeric volatile complexes.

A compound comprising one or more polysubstituted imidazolate anions coordinated to a metal selected from the group consisting of barium, strontium, magnesium, radium or calcium or mixtures thereof. Alternatively, one anion can be substituted with and a second non-imidazolate anion.

Synthesis of the novel compounds and their use to form BST films is also contemplated.

7 Claims, 22 Drawing Sheets

(56) References Cited

OTHER PUBLICATIONS

Troeger; "Weitere Beitrage Zur Kenntniss Der Recutionspoudukte Des Starren Alpha-Dichlorcyanathyls"; Journal Fue Praktische Chemie (Leipzig); vol. 2, No. 50; 1894; pp. 447-452; XP-009146427.

Deng, X., et al; "CuI-Catalyzed Amination of Arylhaldies with Guanidines or Amidines: A Facile Synthesis of 1-H-2-Substituted Benzimidazoles"; Journal of Organic Chemistry; vol. 74, No. 15; 2009; pp. 5742-5745; XP-002630387.

Beccalli, E.M., et al; "Imidazoles and Pyrrolo<2,3-d>Isoxazoles from Isozazol-5(4H)-Ones"; vol. 2; 1991; pp. 127-131; XP-002630388.

Gompper, R., et al; "2.4.5-Tris-(Diethylamino)-4H-Imidazol Und Davon Abgeleitete Fulvene Und Fulvalene"; Tetrahedron Letters; vol. 22, No. 31; 1981; pp. 2973-2976; XP-002630389.

Iwashita, S.; "Novel Imidozle Ring Formation for Alfa Olefins, Carbon Monoxide and Ammonia"; Journal of Organic Chemistry; vol. 36, No. 25; 1971; pp. 3927-3928; XP-002630390.

R. S. Brown et al., "Synthesis and physical studies of pyridine and imidazole containing tridentate metal binding ligans," Canadian Journal of Chemistry, 1980, 58(9), pp. 889-901.

* cited by examiner

VOLATILE IMIDAZOLES AND GROUP 2 IMIDAZOLE BASED METAL PRECURSORS

CROSS REFERENCE TO RELATED APPLICATIONS

This patent application claims the benefit of prior U.S. Provisional Patent Applications Ser. No. 61/301,824 filed Feb. 5, 2010 and 61/369,448 filed Jul. 30, 2010.

BACKGROUND OF THE INVENTION

The semiconductor fabrication industry continues to source volatile metal containing precursors for vapor deposition processes, including chemical vapor deposition (CVD) and atomic layer deposition (ALD), for fabricating conformal metal containing films on substrates, such as silicon, metal nitride, metal oxide and other metal-containing layers, using these metal-containing precursors.

Barium and strontium containing precursors are especially sought after for the deposition of thin barium and strontium oxide containing thin films, such as: strontium titanate (STO) and barium strontium titanate oxide (BST) for advanced memory device manufacture. Strontium precursors are also useful for the thin film deposition of ferroelectric materials of the type $SrBi_2Ta_2O_9$ for non-volatile memory, for the fabrication of thin film high temperature (Tc) superconductors of the type $Bi_2Sr_2Ca_{n-1}Cu_nO_{5+(2n-1)d}$ and for the manufacture of SrS:Ce and SrS:Cu phosphors for electroluminescent displays. Although there are fluorinated barium precursors which have excellent volatility, their use for BST manufacturing is effectively precluded, since fluoride ion can form in the oxide film and act as a charge carrier, which degrades the dielectric constant of the oxide film. Numerous strontium sources for strontium oxide and strontium titanate exist, but none have the ALD performance of the precursors of this disclosure.

Thus, there is a strong need for volatile unfluorinated barium and strontium precursor compounds with high ALD performance, but such compounds are scarce, especially so for barium. This stems from the large ionic radius of the barium +2 and strontium +2 ions requiring ionic ligands which can provide a coordinating environment sufficient to provide compounds which are monomeric or dimeric in strontium or barium. If this requirement is not met, the strontium, and especially the barium compounds tend to form highly associated or polymeric structures of limited volatility. However, even if monomeric or dimeric structures can be achieved, they may still not possess the thermal stability required to survive the high sublimation or distillation temperatures required for their vaporization and to maintain their thermal stability when adsorbed as monolayers in ALD. For all of these reasons, unfluorinated barium and strontium precursors, which are monomeric or dimeric, thermally stable, readily volatile and highly suited to BST and STO manufacture by ALD or CVD, are extremely scarce but highly sought after. Even more sought after are group 2 volatile precursors which have high deposition rates in ALD.

The prior art has attempted to provide precursors for these applications, as set forth below. However, none of the metal complexes in the prior art share the special characteristic of the complexes disclosed in the present invention. The compounds disclosed herein are exceptional in their volatility and thermal stability under conditions of vaporization. In addition, they have exceptionally high ALD deposition rates enabling them to grow 1 monolayer of metal oxide per ALD cycle. This makes them highly effective as precursors for STO and BST film growth and any other application which requires volatile sources of barium, strontium, magnesium, radium or calcium precursors.

Barium and other alkaline earth metal diketiminates are described in the literature. For beta-diketonates the compound $[Ba(THD)_2]_4$ (where THD is 3,3,5,5-tetramethylheptanedionate) has been reported. Although it is a stable and volatile compound, its molecular weight of >2000 renders its utility in ALD or CVD process challenging, especially when compared to smaller, more volatile, compounds, such as the barocenes and especially when compared to the new compounds of the present invention, which are more cleanly volatile and have higher ALD deposition rates and lowered melting points when compared to the barocenes.

Thermally stable and volatile tri(pyrazoyl)borate alkaline earth complexes, including those of barium have been reported. However, these compounds suffer from containing the element boron, which under oxidation conditions, deposits boron oxide into the metal oxide of a CVD or ALD process.

Volatile barium and strontium complexes based on diketiminate ligands bearing $NMe_2$ groups substituted on the core diimine nitrogens are reported. But the barium molecule in this series sublimed to give only a 79% sublimation recovery leaving a 14 wt % involatile residue. This sublimation was performed at 0.05 Torr. If it had been conducted at atmospheric pressure, its involatile residue would have been significantly higher. These results indicate this molecule to have limited suitability as a precursor for CVD or ALD processes.

The synthesis and thermal properties of a series of nine different barium cyclopentadienyl, also known as barocenes', have been reported. Selected species from these barocenes, particularly the barium bis(tri-tert-butlycyclopentadienyl), are 'state of the art' precursors possessing an attractive combination of thermal stability and volatility. However, the new molecules of the present invention are shown to be superior to them with regard to these two key properties. Additionally, the new precursors of this disclosure, due to their unique molecular characteristics, also have exceptionally high ALD deposition rates making them more attractive from a device manufacturing perspective.

OTHER REFERENCES OF INTEREST INCLUDE

WO 2009/086263.

J. Norman, G. Pez, *J. Chem. Soc. Chem. Commun.*, 971, (1991)

Harder, S. (2002); "Homoleptic beta Diketiminate Complexes of the Alkaline Earth Metals Trends in the Series Mg, Ca, Sr, and Ba"; Organometallics 21(18), 3782-3787.

U.S. Pat. No. 5,319,118

El-Kaderi, H. M. and M. J. W. Heeg, C. H.; (2004). "Sandwich Complexes of the Heavier Alkaline Earth Metals Containing 5-Diketiminato Ligand Sets." Organometallics 23: 4995-5002.

M. J. Saly, M. J. Heeg and C. Winters, Inorganic Chemistry, publication date (Web) Apr. 27, 2009.

B. Sedai, M. J. Heeg and C. Winter, Organometallics, 2009, 18 (4) p 1032-1038.

Timo Hatanpaa, Marko Vehkamaki, Ilpo Mutikainen, Jarno Kansikas and Mikko Ritala "Synthesis and characterization of cyclopentadienyl complexes of barium: precursors for atomic layer deposition of $BaTiO_3$" Dalton Trans., 2004, p. 1181-1188.

J. Zhang, X. Chen, *Chem. Comm.* 1689-1699 (2006). , Electrochem

H. A. Every, T. A. Zawodzinski ical Society Proceedings, 277-286, Volume 21 (2001).

BRIEF SUMMARY OF THE INVENTION

Sterically hindered imidazole ligands are disclosed, along with the syntheses of the same, which when complexed to a Group 2 metal, form highly volatile and stable complexes that are exceptionally useful as precursor molecules for CVD, ALD and the like thin film deposition processes.

The present invention is an imidazole molecule which can be deprotonated to yield an imidazolate substituted in at least the 2,5-positions with a bulky group, R, of the formula:

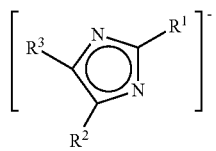

wherein $R^1$ and $R^3$ are individually bulky groups having sufficient 3-dimensional form to impart a property to the imidazolate to bond with metals in an eta1, eta-2, eta-3, eta-4 or eta-5 bond; and $R_2$ can be a bulky group or a group which is not a bulky group.

Preferably, the imidazolate's $R_1$ and $R_3$ are individually selected from the group consisting of tert-butyl, isopropyl, tert-amyl, neopentyl, adamantly, hexyl, cyclohexyl, propyl, butyl, isobutyl, pentyl, isopentyl, neopenty, norbornyl, bicyclo[2.2.1]heptyl, dimethylpropyl, dimethylbutyl, dimethylpentyl, dimethylhexyl, ethylmethylpropyl, isohexyl, isopentyl Preferably, the imidazolate's $R_2$ is a bulky group.

Preferably, the imidazolate comprises 2,4,5-tris-t-butyl-imidazolate.

In another aspect, the present invention teaches compounds comprising one or more polysubstituted imidazolate anions coordinated to a metal selected from the group consisting of barium, strontium, magnesium, calcium or radium or mixtures thereof.

Mixtures of these novel imidazolate metal complexes combined with other metal complexes are also contemplated where the additional metal complex can be a titanium imidazolate complex or a non-imidazolate complex including where the complexes are dissolved in a solvent and the resulting formulation used in DLI mode. Particularly useful combinations would include those where a strontium imidazole is combined with a titanium complex as a simple mixture or co-dissolved in a suitable solvent as a DLI formulation for STO ALD or CVD. Similarly, barium imidazolate complexes can be combined with suitable titanium complexes for BST film growth.

Alternatively, one imidazolate anion can be substituted with a second non-imidazolate anion. In addition, the imidazolate anion may also bear a substituent, which is also deprotonated to yield a dianionic species, and this dianion is coordinated to a metal, such as barium, strontium, magnesium, calcium or radium or mixtures thereof.

Preferably, the second non-imidazolate anion is selected from the group consisting of polysubstituted imidazolate anion, polyalkylated pyrrolyl anion, beta-diketonates, acetates, ketoiminates, diimines, alkoxides, amides, hydrides, beta-ketoesters, amidinates, guanidinates, cyclopentadienyl, cyanide, isocyanide, formate, oxalate, malonate, phenoxide, thiolate, sulfide, nitrate, alkyl, silylalkyl, fluoroalkyl, aryl, imidazolate, hydride and mixtures thereof.

Synthesis of the novel compounds and their use to form BST films is also contemplated.

Most preferably, the imidazolate is:
2,4,5-tri-tert-butylimidazolate
2-tert-butyl-4,5-di-(1,1-dimethylpropyl)imidazolate
2-(1,1-dimethylbutyl)-4,5-di-tert-butylimidazolate
2-(1,1-dimethylbutyl)-4,5-di-(1,1-dimethylpropyl)imidazolate; and their barium, strontium, magnesium and calcium salts.

An embodiment of the present invention's imidazolate comprises a mixture of strontium imidazolate with a volatile titanium source. More preferably, this embodiment includes as the volatile titanium source an imidazolate based titanium precursor Alternatively, in the imidazole, $R^1$, $R^2$ and $R^3$ are linked together to form a cyclic structure.

Alternately, the imidazole has at least two of $R^1$, $R^2$ and $R^3$ joined so that two or more imidazole ligands are joined together.

Preferred metal imidazolates include; Di-barium tetra(2,4,5-tris-t-butylimidazolate); Di-barium tetra(2-tert-butyl-4,5-di-(1,1-dimethylpropyl)imidazolate); Di-barium tetra(2-(1,1-dimethylbutyl)-4,5-di-tert-butylimidazolate); and, Di-barium tetra(2-(1,1-dimethylbutyl)-4,5-di-(1,1-dimethylpropyl)imidazolate); Di-strontium tetra(2,4,5-tris-t-butylimidazolate); Di-strontium tetra(2-tert-butyl-4,5-di-(1,1-dimethylpropyl)imidazolate); Di-strontium tetra(2-(1,1-dimethylbutyl)-4,5-di-tert-butylimidazolate); and, Di-strontium tetra(2-(1,1-dimethylbutyl)-4,5-di-(1,1-dimethylpropyl)imidazolate).

Preferably, the present invention's metal imidazolates are contained in a stainless steel container. More preferably, the stainless steel container is electropolished in its interior. Most preferably, the stainless steel container is outfitted with inlet and outlet valves for high purity, low dead space service.

DETAILED DESCRIPTION OF THE INVENTION

Figure 1:
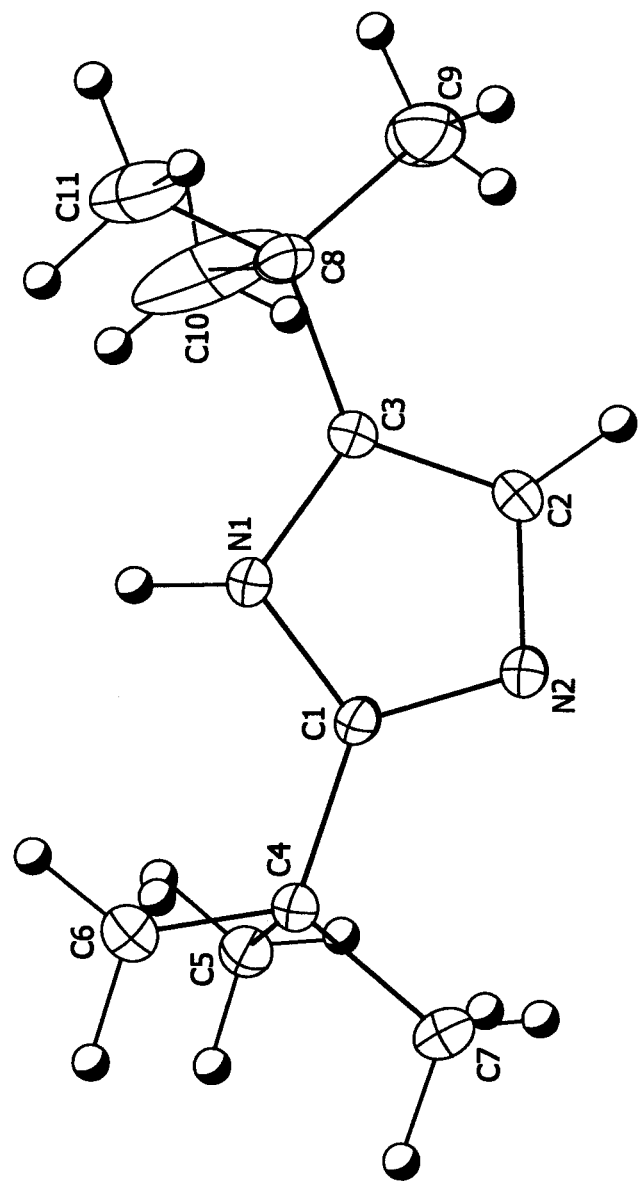
FIG. 1 is an illustration of the X-ray structure of 2,5-di-tert-butylimidazole.

Currently, a major use of ALD in the semiconductor industry is the growth of metal oxides, such as: strontium oxide, barium oxide and the perovskite oxides: strontium titanate (STO) and barium titanate (BST). Often, these processes are required to grow perfectly conformal films into deeply bored cyclindrical volumes (vias) or over colulmar structures (pillars), where it is imperative that there is no thermal decomposition or CVD component that will degrade conformality.

One major mechanism by which precursors thermally degrade is when the anionic ligand to which the metal coordinates starts to decompose. Thus, making metal precursors which are coordinated to anions which are thermally robust is highly desirable. The novel imidazolate ligand anions of this disclosure are demonstrated to be of high thermal stability. Also, it is important that in the evaporation phase the anionic ligand does not coordinate to multiple metal centers to form compounds of high nuclearity, such as; tetramers or polymers, which are either of low volatility or are involatile. So, in summation, the anionic ligands need to coordinate a relatively low number of metal centers, such as; 1, 2 or 3 and are thermally very resilient against degradation.

However, notwithstanding this need for high thermal stability, the precursors also need to be chemically highly reactive under ALD conditions. To achieve such a highly stable anionic ligand also means that its formal negative charge needs to be stabilized by the structure of the ligand. The novel imidazolate anions of this disclosure stabilize their negative charge by being a five membered ring aromatic anion which contains two nitrogen atoms. The electrogenativity of the latter two atoms also increase the stability of the formal negative charge. Other five memebered aromatic ring anions exist, such as; cyclopentadienyl and pyrrolyl, but these are not as stable as the imidazolate anions of this disclosure. The cyclopentadienyl ring contains only five carbon atoms and the pyrrolyl ring contains four carbon atoms and one nitrogen atom. Also, the relative acidities of the ligands cyclopentadiene, pyrrole and imidazole are 16.0, 16.45 and 14.5, respectively, showing that imidazole is the most acidic of the three, indicating that its conjugate base, i.e., the imidazolate anion, is the most stable of the three. Also, the practical steric limit for substituting large bulky groups, such as; tert-butyl onto cyclopentadienyl, pyrrolyl and imidazolate anions is anticipated to be three. This means that such a substituted cyclopentadienyl ring will have two ring carbons remaining substituted with only hydrogen, and pyrrolyl will have one ring carbon substituted with only hydrogen. However, the analogous tri-substituted imidazolate ring has no such ring carbons bearing only hydrogen, since all three of its ring carbons are substituted with the three tert-butyl type substituents.

While not wishing to be bound by theory, it is believed that the absence of hydrogen substituents on the ring of imidazolate anions renders them more thermally stable than either comparably substituted cyclopenatdienyl or pyrrolly anions. Also important is the shape and volume of the anionic ligand, because if its structure bears large bulky groups, such as; tert-butyl, these can ensure that the nuclearity of the resulting metal complexes will be low, since bonding access to the ligand will be restricted to 3 or less metal centers. The novel imidazole ligands of this disclosure are shown to be readily functionalized with such bulky groups and demonstrated to be capable of binding 3 or less metal centers to make metal complexes that are volatile and highly useful as precursors. Besides these features, it is also desirable if the synthesis of the organic ligand can be accomplished efficiently and in high yield and can produce pure product with no side reactions.

It is desirable if the synthesis of the ligand permits precise control over the introduction of different organic groups to its structure, and this is readily achieved with the imidazole ligands of this disclosure. Thus, if a specifically trisubstituted imidazole ligand is targeted, it can be readily prepared in pure form, while avoiding the formation of by products, where the different substituents are more randomly distributed. The latter case is more common for cyclopentadiene and pyrrole ligands, resulting in a mixture of isomers, which need extensive separation into their components.

It is shown that the novel imidazole ligands of this disclosure can be synthesized in high yield and purity as only one isomer, when asymmetrically substituted with different bulky groups, such as; tert-butyl. This is particularly important with respect to making a pure metal complex of lowered melting point or a liquid, which is highly desirable, since liquid precursors are easier to evaporate than solid precursors and are typically more soluble in solvents to make solutions for direct liquid injection (DLI) delivery.

To synthesize such a precursor typically entails building ligands that are asymmetrically functionalized with steric protecting groups, since this results in an asymmetric metal complex, which in turn results in a lowered melting point, due to the asymmetry lowering the crystal lattice packing energies of the metal precursor. Thus, it is preferable that the ligand can be efficiently asymmetrically functionalized, if desired, in a controlled and efficient manner.

This can readily be achieved in the synthesis of the novel imidazolate ligands of this disclosure by first synthesizing an alpha-diketone substituted with bulky alkyl groups, which will ultimately occupy the 4 and 5 ring positions of the imidazole ring, then cyclizing this in the presence of ammonium acetate with an aldehyde substituted with a bulky alkyl group, which will ultimately occupy the 2 position of the imidazole ring. In this way the ultimate substitution pattern of the imidazole, including asymmetric alkylation, is readily controlled.

Figure 6:
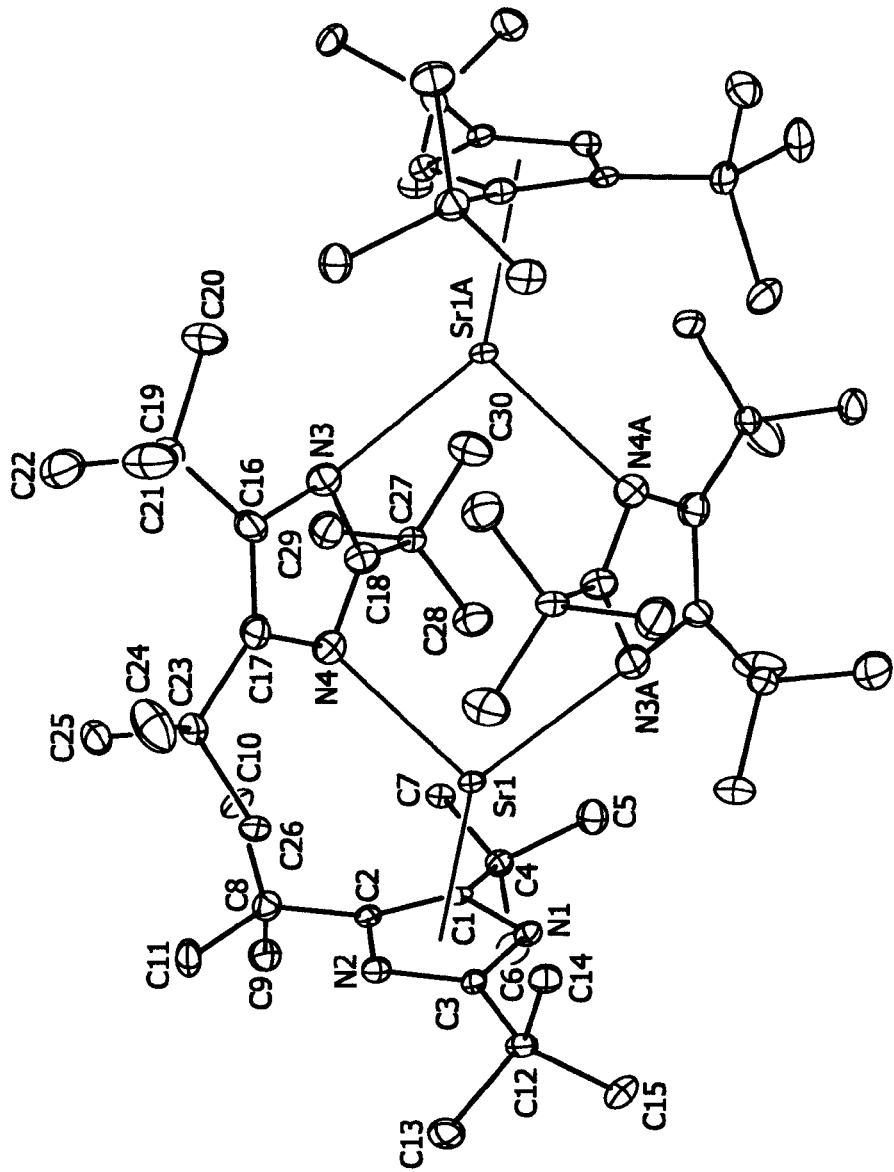
FIG. 6 is an illustration of di-strontium tetra(2,4,5-tri-tert-butylimidazolate) (hydrogen atoms are not illustrated for purposes of clarity).
Figure 8:
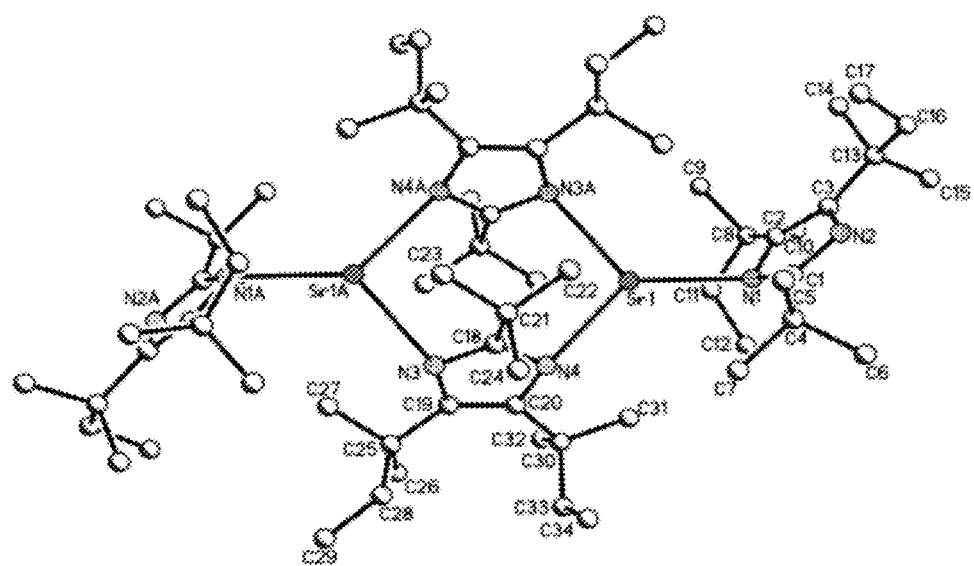
FIG. 8 is an illustration of di-strontium tetra(2-tert-butyl-4,5-di(1,1-dimethylpropyl)imidazolate(hydrogen atoms are not illustrated for purposes of clarity).

An example of asymmetric alkylation is found in the comparison of FIGS. 6 and 8, which show the strontium complexes of the tri-substituted imidazoles: 2,4,5-tri-tert-butyl-imidazole and 2-tert-butyl-4,5-di-(1,1-dimethylpropyl)imidazole respectively.

The former imidazole is symmetrically substituted with three tert-butyl groups, whereas the latter imidazole is substituted with one tert-butyl group in the 2 position and two tert-amyl groups in the positions 4 and 5 and is thus asymmetric.

Figure 7:
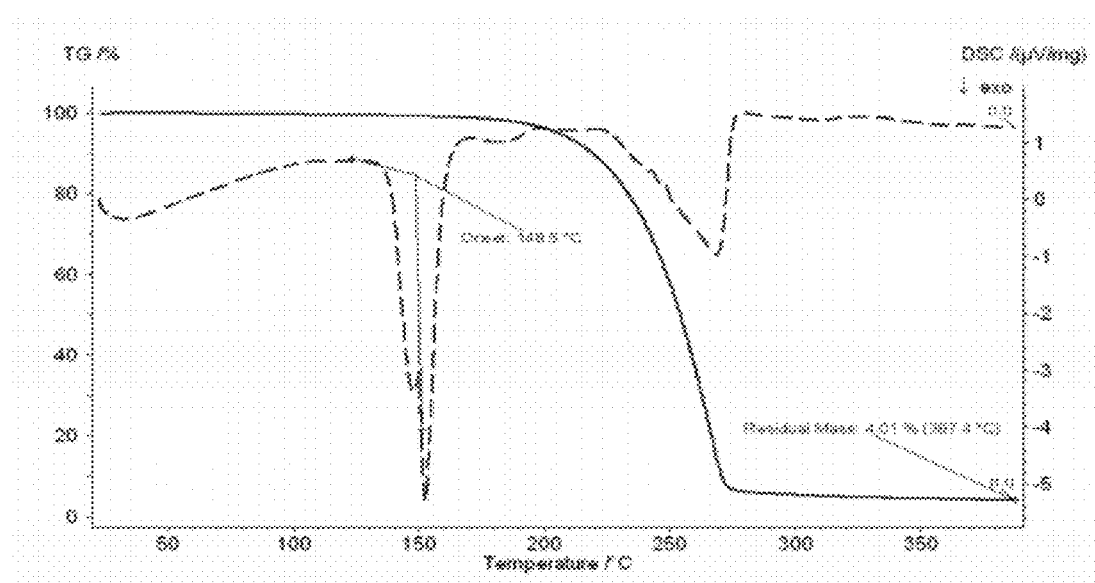
FIG. 7 is the TGA/DSC of di-strontium tetra(2,4,5-tri-tert-butylimidazolate), wherein the TGA is a solid line and the DSC is a dashed line.
Figure 9:
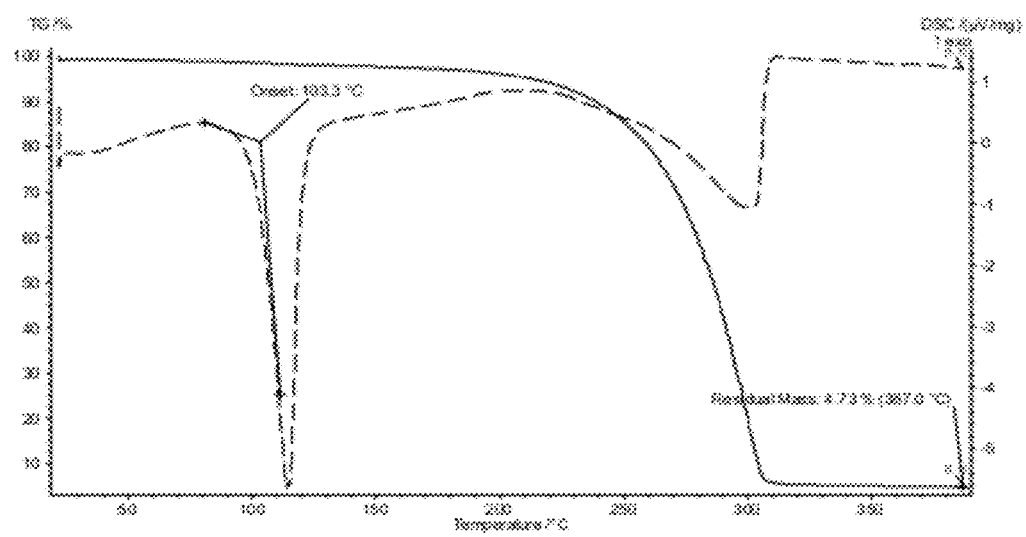
FIG. 9 is the TGA /DSC result for di-strontium tetra(2-tert-butyl-4,5-di(1,1-dimethylpropyl)imidazolate), wherein the TGA is a solid line and the DSC is a dashed line.

FIGS. 7 and 9 show the thermogravimetric analysis (TGA) results for the structures of FIGS. 6 and 8, respectively, where the complex of FIG. 6 is shown to melt at 148° C., whereas the melting point of the structure of FIG. 8 is only 103° C.

Figure 4:
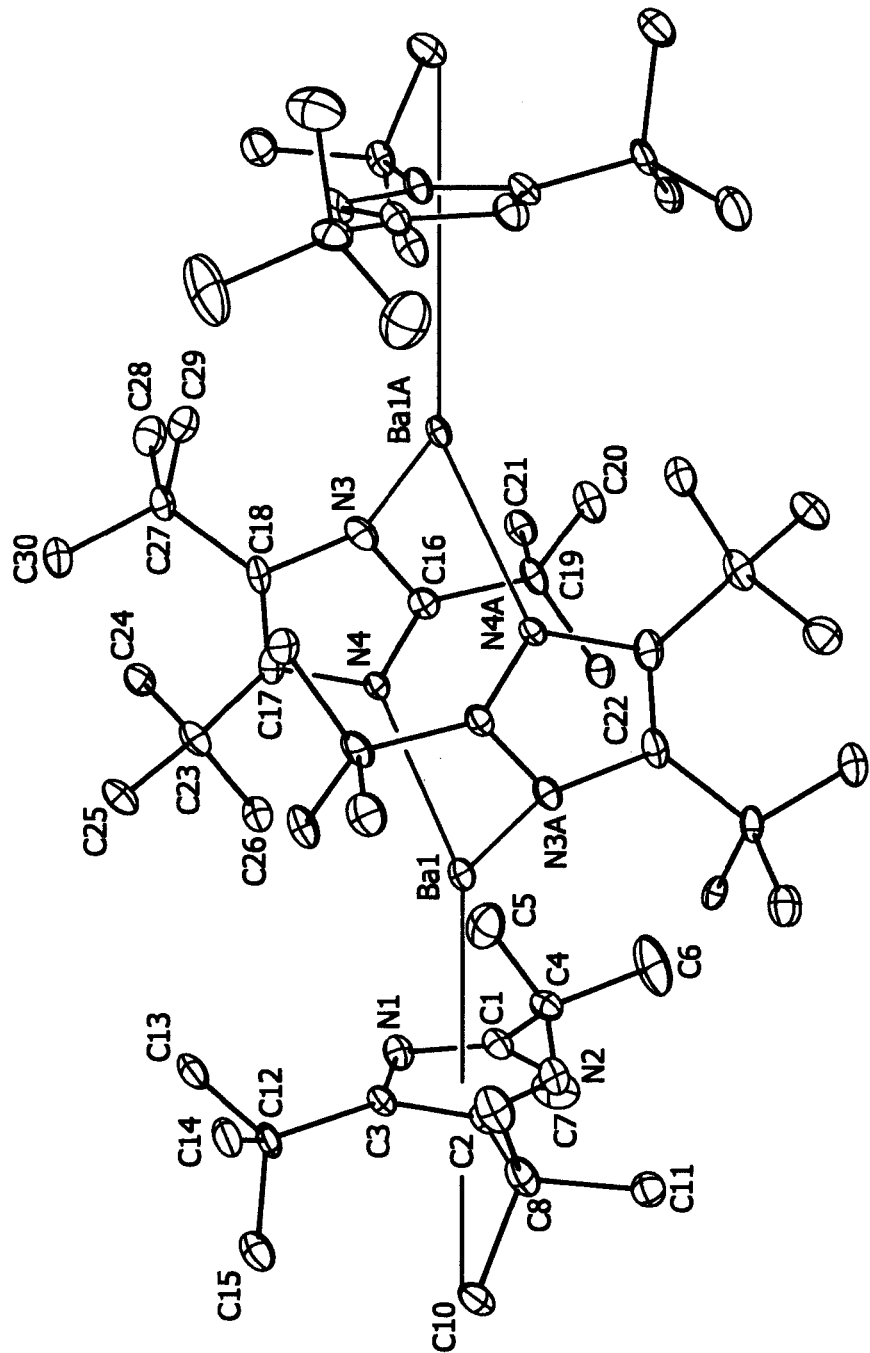
FIG. 4 is an illustration of di-barium tetra(2,4,5-tri-tert-butylimidazolate) (hydrogen atoms are not illustrated for purposes of clarity).
Figure 10:
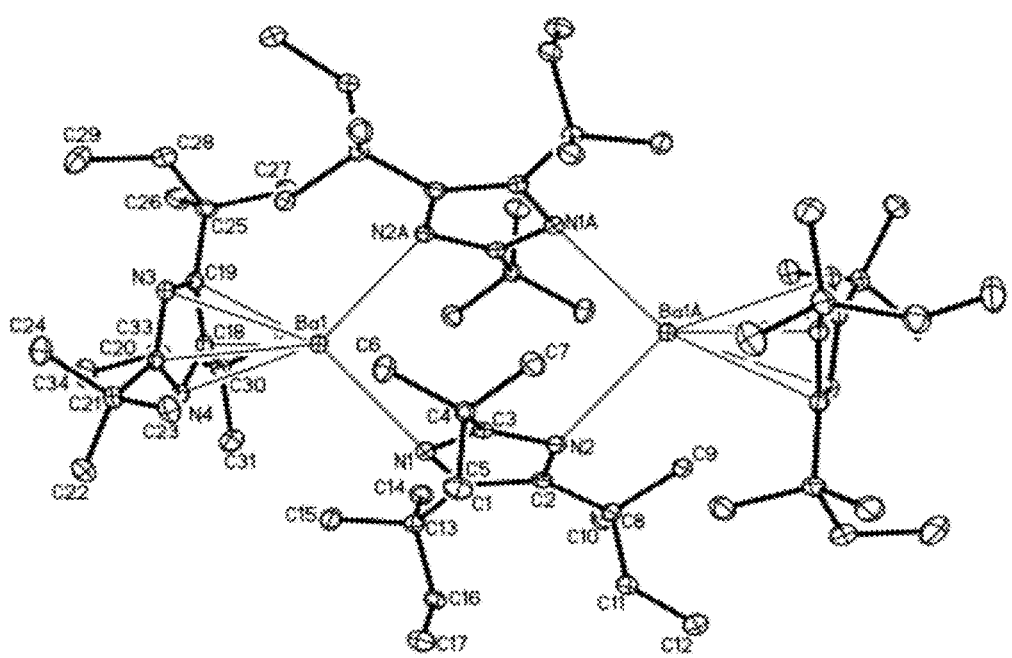
FIG. 10 is an illustration of di-barium tetra(2-tert-butyl-4,5-di(1,1-dimethylpropyl)imidazolate) (hydrogen atoms are not illustrated for purposes of clarity).
Figure 11:
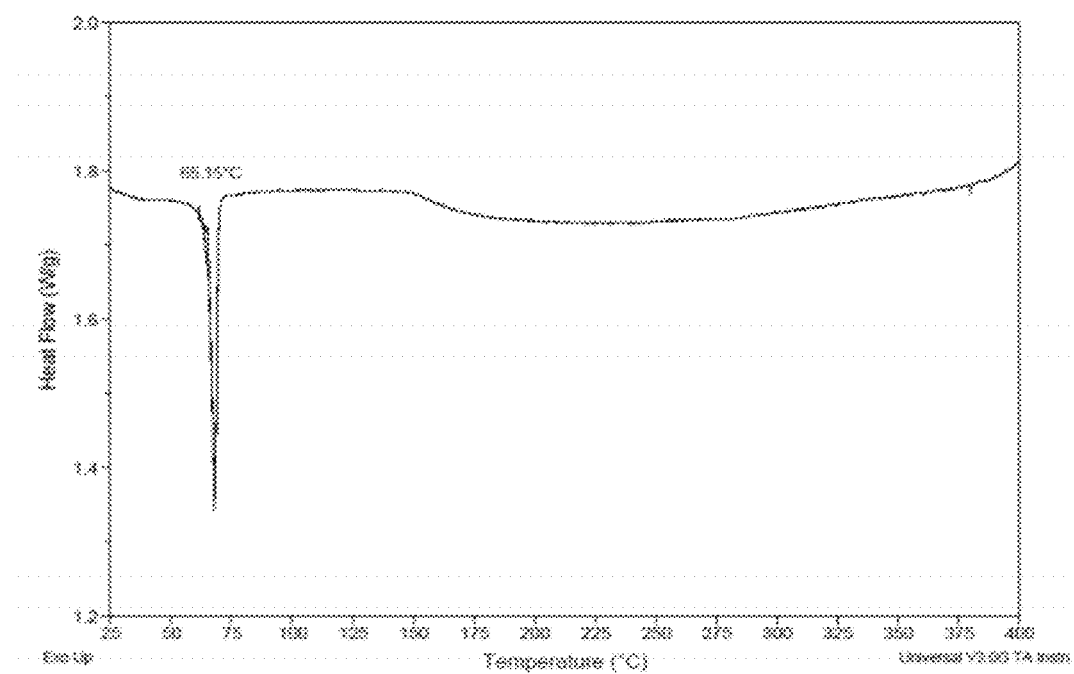
FIG. 11 is the DSC result for di-barium tetra(2-tert-butyl-4,5-di(1,1-dimethylpropyl)imidazolate).
Figure 12:
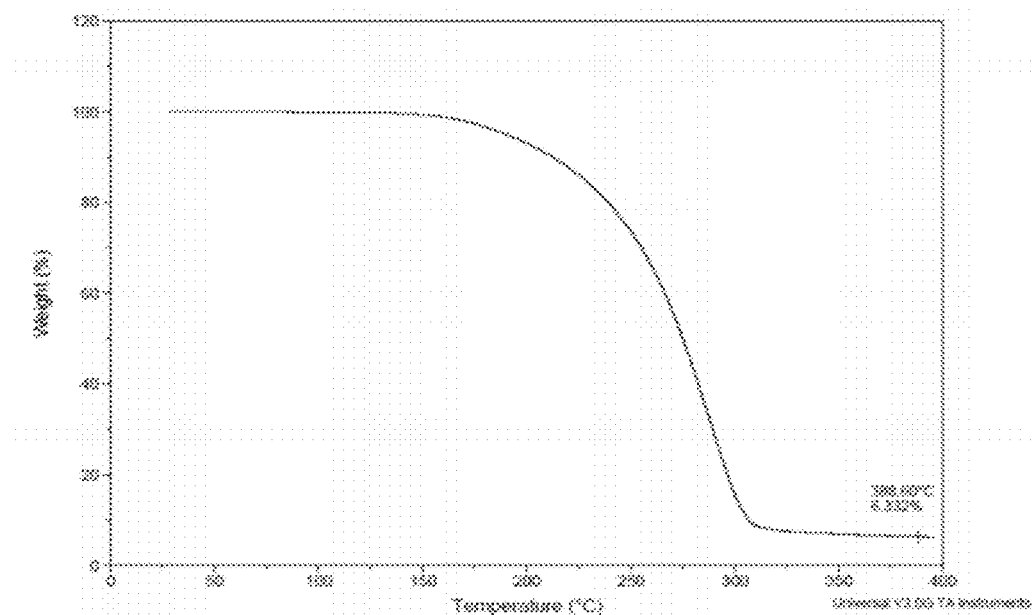
FIG. 12 is the TGA results for di-barium tetra(2-tert-butyl-4,5-di(1,1-dimethylpropyl)imidazolate).
Figure 13:
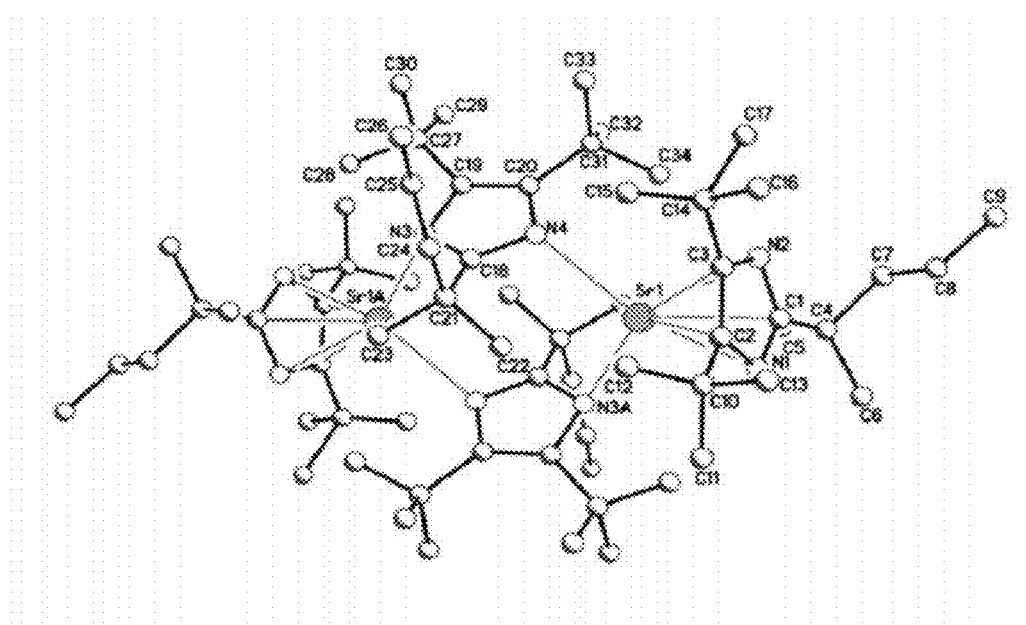
FIG. 13 is an illustration of di-strontium tetra(2-(1,1-dimethylbutyl)-4,5-di-tert-butyl)imidazolate) (hydrogen atoms are not illustrated for purposes of clarity).
Figure 14:
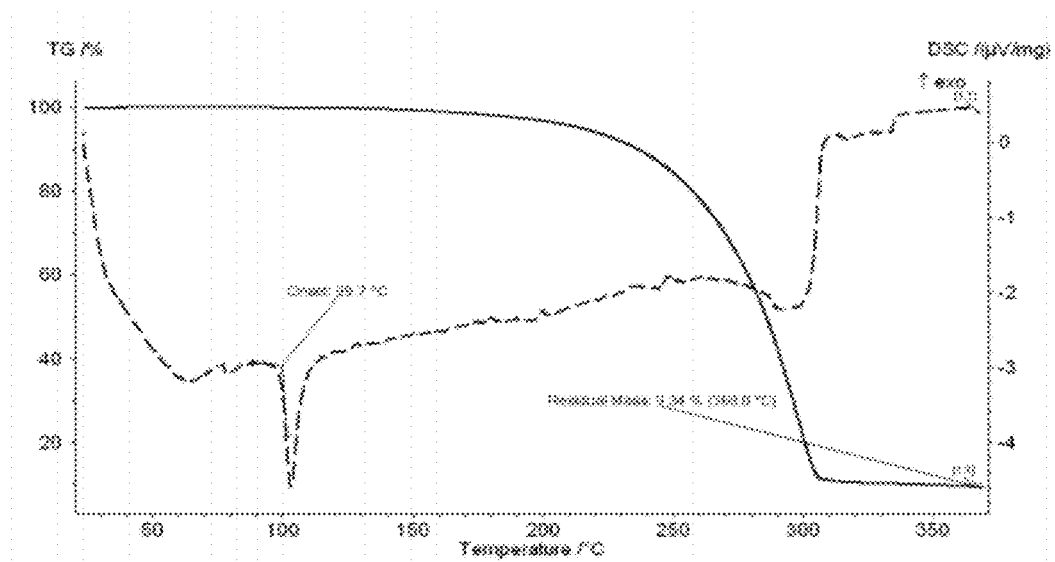
FIG. 14 is the TGA/DSC result for di-strontium tetra(2-(1,1-dimethylbutyl)-4,5-di-tert-butyl)imidazolate), wherein the TGA is a solid line and the DSC is a dashed line.
Figure 15:
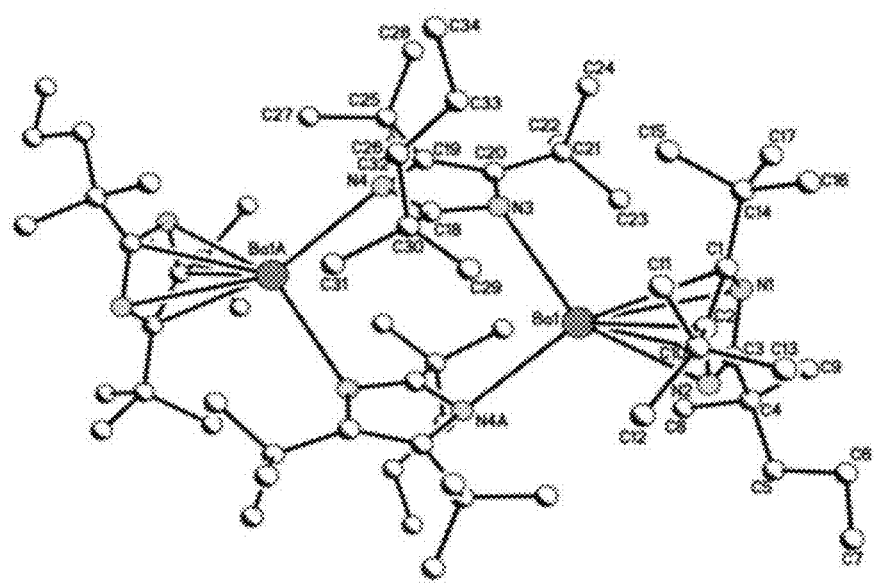
FIG. 15 is an illustration of di-barium tetra(2-(1,1-dimethylbutyl)-4,5-di-tert-butyl)imidazolate) (hydrogen atoms are not illustrated for purposes of clarity).

The barium complexes of these two imidazoles, shown in FIGS. 4 and 10, show a more dramatic lowering of melting point from 151° C. (shown in FIG. 5) to 65° C. (shown in FIG. 11), respectively.

Thus, the effect of asymmetric tri-substitution upon imidazole yields metal complexes of lowered melting point. It is further anticipated that even lower melting points can be achieved, when each of the three substituents is unique. Additionally, larger asymmetric alkyl groups can also be used to lower the final precursor melting point.

The novel compounds of the present invention comprise anionic functionalized imidazolate ligands, which may be coordinated to barium or strontium or magnesium, radium or calcium ions to yield either monomeric or dimeric compounds, in addition to neutral ligand adducts of those compounds, which have exceptional thermal stability and clean evaporation characteristics.

Figure 19:
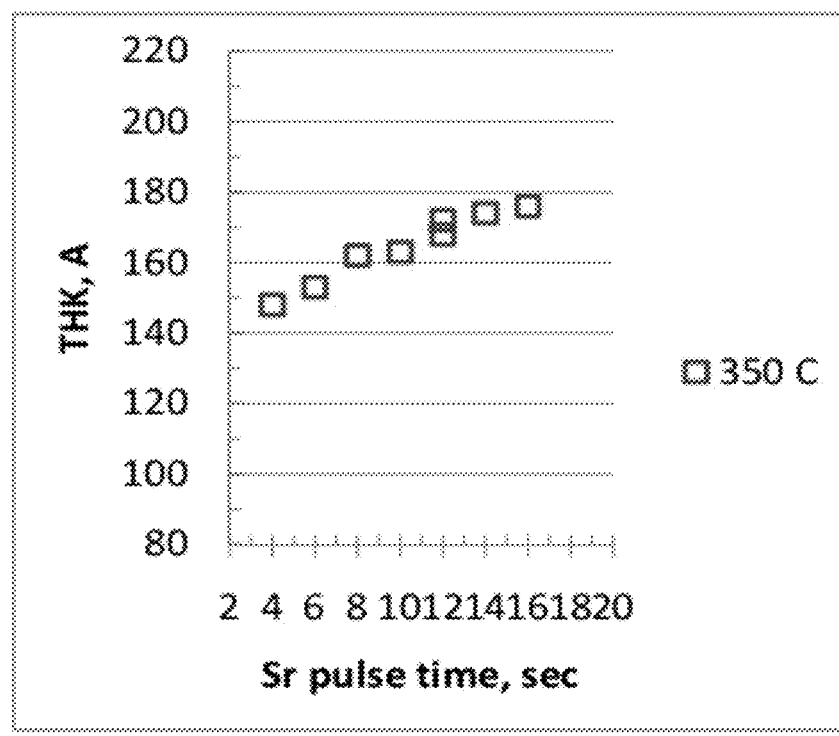
FIG. 19 illustrates the ALD saturation curve for a di-strontium tetra(2-tert-butyl-4,5-di-(1,1-dimethylpropyl)imidazolate)/ozone ALD process at 350° C. substrate temperature.
Figure 20:
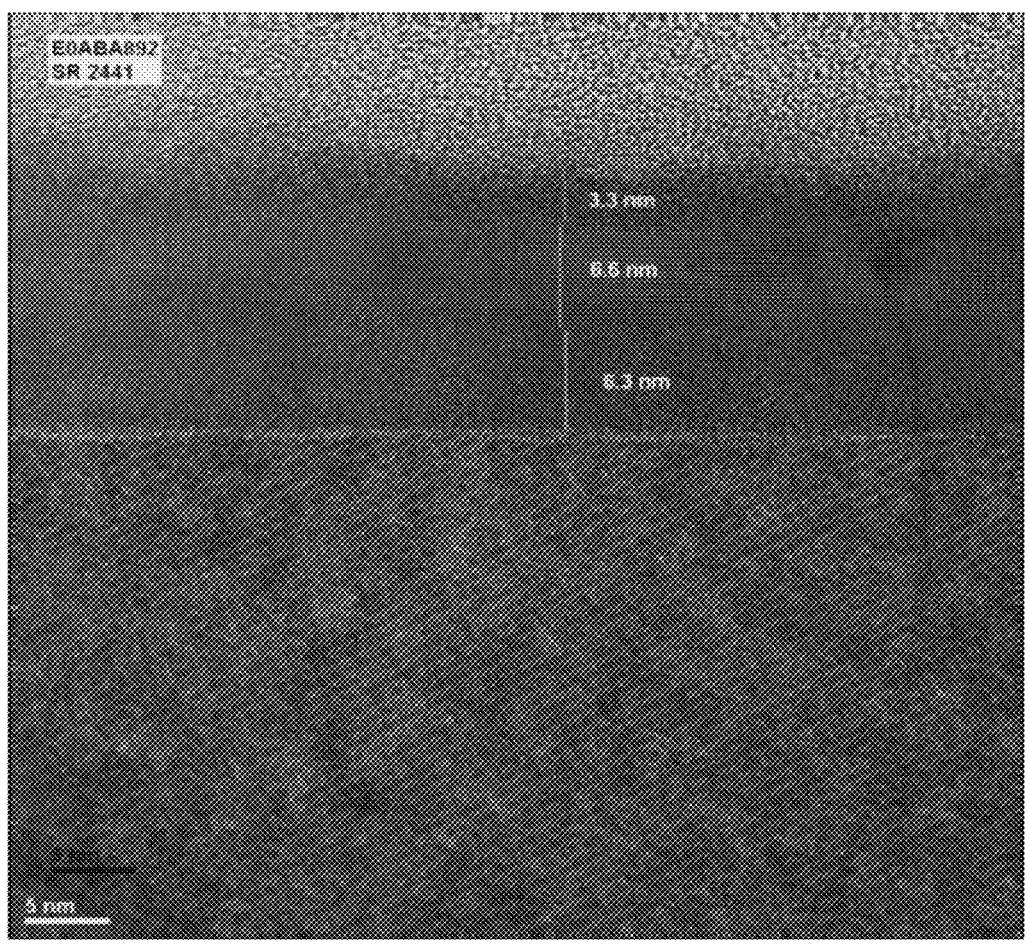
FIG. 20 illustrates the transmission electron microscopy (TEM) of an ALD SrO film grown from di-strontium tetra(2-tert-butyl-4,5-di-(1,1-dimethylpropyl)imidazolate) at 375° C., capped with 3.3 nm of titanium dioxide.

These new complexes are also demonstrated to deliver exceptional ALD performance with growth rates of metal oxides >2 Angstroms per cycle thereby permitting the growth of one monolayer of metal oxide per ALD cycle. Additionally, the ALD metal oxides grown from these new precursors are crystalline as deposited. Typically ALD metal oxide films are not crystalline as deposited and hence do not exhibit their full permittivity value. Hence they need to be thermally annealed at higher than deposition temperatures for crystallization to occur. This requires additional processing time and subjects the device upon which the film is grown to excessive heating which can potentially deteriorate it performance. Therefore, being able to deliver crystalline oxide films as deposited represents a significant manufacturing advantage. Experimentally we find that after about 10-16 seconds of precursor pulse, sufficient strontium is delivered to achieve a monolayer of SrO after oxidation. Thus, good control over the effective saturation of the initially adsorbed layers can be achieved quickly, as shown in FIG. 19. Thus, the imidazolate metal complexes of this disclosure are unique in their ability to grow metal oxides at exceptionally high ALD deposition rates when contrasted to comparable cyclopentadienyl or pyrrolyl metal precursors. TEM analysis of an ALD SrO film grown at 375° C. using di-strontium tetra(2-tert-butyl-4,5-di-(1,1-dimethylpropyl) and ozone reagent, as shown in FIG. 20, clearly indicates a regular array of metal oxide atoms which are spaced at 24 grains per 6.6 nm=66/24=2.75 Angstroms which corresponds precisely with the unit cell dimensions of pure (001) strontium oxide. In addition, if the amorphous layer below this array were annealed into a crystalline phase it should yield about 23 layer to give a total of 24+23=47 layers of SrO. Experimentally, 50 ALD cycles were used so this confirms the effective deposition of ~1 monolayer of SrO/cycle.

The imidazolate rings can also be asymmetrically substituted to yield lower melting point compounds of high solubility, well suited to direct liquid injection (DLI). The structure of the ligand 2,5-di-tertbutylimidazole, an imidazole ligand created according to this disclosure, Example 1, is shown in FIG. 1.

The present invention is, in one embodiment, an imidazole substituted in at least the 2,5-positions with a bulky group, R, of the formula:

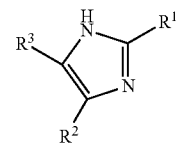

Wherein $R^1$ and $R^3$ are individually bulky groups having sufficient 3-dimensional form to impart a property to the imidazole so that after it is deprotonated to give imidazolate anion it can bond with metals in a eta-5 bond, eta-4, eta-3, eta-2 or eta-1 bond; and $R_2$ can be a bulky group or a group which is not a bulky group. $R^1$, $R^2$ and $R^3$ can also be bulky groups which contain an unsaturation such as a carbon-carbon double bond or a carbon-carbon triple bond.

Preferably, the imidazole is:

2,4,5-tri-tert-butylimidazole
2-tert-butyl-4,5-di-(1,1-dimethylpropyl)imidazole
2-tert-butyl-4,5-di-(1,1-dimethylbutyl)imidazole
2-tert-butyl-4,5-di-(1,1-dimethylpentyl)imidazole
2-tert-butyl-4,5-di-(1,1-dimethylhexyl)imidazole
2-(1,1-dimethylpropyl)-4,5-di-tert-butlyimidazole
2,4,5-tri-(1,1-dimethylpropyl)imidazole
2-(1,1-dimethylpropyl)-4,5-di-(1,1-dimethylbutyl)imidazole
2-(1,1-dimethylpropyl)-4,5-di-(1,1-dimethylpentyl)imidazole
2-(1,1-dimethylpropyl)-4,5-di-(1,1-dimethylhexyl)imidazole
2-(1,1-dimethylbutyl)-4,5-di-tert-butylimidazole
2-(1,1-dimethylbutyl)-4,5-di-(1,1-dimethylpropyl)
2,4,5-tri-(1,1-dimethylbutyl)imidazole
2-(1,1-dimethylbutyl)-4,5-di-(1,1-dimethylpentyl)imidazole
2-(1,1-dimethylbutyl)-4,5-di-(1,1-dimethylhexyl)imidazole
2-(1,1-dimethylpentyl)-4,5-di-tert-butylimidazole
2-(1,1-dimethylpentyl)-4,5-di-(1,1-dimethylpropyl)limidazole
2-(1,1-dimethylpentyl)-4,5-di-(1,1-dimethylbutyl)imidazole
2,4,5-tri-(1,1-dimethylpentyl)imidazole
2-(1,1-dimethylpentyl)-4,5-di-(1,1-dimethylhexyl)limidazole
2-(1,1-dimethylhexyl)-4,5-di-tert-butylimidazole
2-(1,1-dimethylhexyl)-4,5-di-(1,1-dimethylpropyl)imidazole 2-(1,1-dimethylhexyl)-4,5-di-(1,1-dimethylbutyl)imidazole
2-(1,1-dimethylhexyl)-4,5-di-(1,1-dimethylpentyl)imidazole
2,4,5-tri-(1,1-dimethylhexyl)imidazole
2,4-di-tert-butyl-5-(1,1-dimethylpropyl)imidazole
2,5-di-tert-butyl-4-(1,1-dimethylpropyl)imidazole
2,4-di-tert-butyl-5-(1,1-dimethylbutyl)imidazole
2,5-di-tert-butyl-4-(1,1-dimethylbutyl)imidazole
2,4-di-tert-butyl-5-(1,1-dimethylpentyl)imidazole
2,5-di-tert-butyl-4-(1,1-dimethylpentyl)imidazole
2,4-di-tert-butyl-5-(1,1-dimethylhexyl)imidazole
2,5-di-tert-butyl-4-(1,1-dimethylhexyl)imidazole
2-tert-butyl-4-(1,1-dimethylpropyl)-5-(1,1-dimethylbutyl)imidazole
2-tert-butyl-4-(1,1-dimethylbutyl)-5-(1,1-dimethylpropyl)imidazole
2-tert-butyl-4-(1,1-dimethylpropyl)-5-(1,1-dimethylpentyl)imidazole
2-tert-butyl-4-(1,1-dimethylpentyl)-5-(1,1-dimethylpropyl)imidazole
2-tert-butyl-4-(1,1-dimethylpropyl)-5-(1,1-dimethylhexyl)imidazole
2-tert-butyl-4-(1,1-dimethylhexyl)-5-(1,1-dimethylpropyl)imidazole
2-tert-butyl-4-(1,1-dimethylpentyl)-5-(1,1-dimethylbutyl)imidazole
2-tert-butyl-4-(1,1-dimethylbutyl)-5-(1,1-dimethylpentyl)imidazole
2-tert-butyl-4-(1,1-dimethylpentyl)-5-(1,1-dimethylhexyl)imidazole
2-tert-butyl-4-(1,1-dimethylhexyl)-5-(1,1-dimethylpentyl)imidazole
2-(1,1-dimethylpropyl)-4-tert-butyl-5-(1,1-dimethylpropyl)imidazole
2-(1,1-dimethylpropyl)-4-(1,1-dimethylpropyl)-5-tert-butyl-imidazole
2-(1,1-dimethylpropyl)-4-tert-butyl-5-(1,1-dimethylbutyl)imidazole
2-(1,1-dimethylpropyl)-4-(1,1-dimethylbutyl)-5-tert-butyl-imidazole
2-(1,1-dimethylpropyl)-4-tert-butyl-5-(1,1-dimethylpentyl)imidazole
2-(1,1-dimethylpropyl)-4-(1,1-dimethylpentyl)-5-tert-butyl-imidazole
2-(1,1-dimethylpropyl)-4-tert-butyl-5-(1,1-dimethylhexyl)imidazole
2-(1,1-dimethylpropyl)-4-(1,1-dimethylhexyl)-5-tert-butyl-imidazole
2,4-di-(1,1-dimethylpropyl)-5-(1,1-dimethylbutyl)imidazole
2,5-di-(1,1-dimethylpropyl)-4-(1,1-dimethylbutyl)imidazole
2,4-di-(1,1-dimethylpropyl)-5-(1,1-dimethylpentyl)imidazole
2,5-di-(1,1-dimethylpropyl)-4-(1,1-dimethylpentyl)imidazole
2,4-di-(1,1-dimethylpropyl)-5-(1,1-dimethylhexyl)imidazole
2,5-di-(1,1-dimethylpropyl)-4-(1,1-dimethylhexyl)imidazole
2-(1,1-dimethylpropyl)-4-(1,1-dimethylpentyl)-5-(1,1-dimethylbutyl)imidazole
2-(1,1-dimethylpropyl)-4-(1,1-dimethylbutyl)-5-(1,1-dimethylpentyl)imidazole
2-(1,1-dimethylpropyl)-4-(1,1-dimethylpentyl)-5-(1,1-dimethylhexyl)imidazole
2-(1,1-dimethylpropyl)-4-(1,1-dimethylhexyl)-5-(1,1-dimethylpentyl)imidazole
2-(1,1-dimethylbutyl)-4-tert-butyl-5-(1,1-dimethylbutyl)imidazole
2-(1,1-dimethylbutyl)-4-(1,1-dimethylbutyl)-5-tert-butyl-imidazole
2,4-di(1,1-dimethylbutyl)-5-tert-butyl-imidazole
2,5-di(1,1-dimethylbutyl)-4-tert-butyl-imidazole
2-(1,1-dimethylbutyl)-4-tert-butyl-5-(1,1-dimethylpentyl)imidazole
2-(1,1-dimethylbutyl)-4-(1,1-dimethylpentyl)-5-tert-butyl imidazole
2-(1,1-dimethylbutyl)-4-tert-butyl-5-(1,1-dimethylhexyl)imidazole
2-(1,1-dimethylbutyl)-4-(1,1-dimethylhexyl)-5-tert-butyl-imidazole
2,4-di(1,1-dimethylbutyl)-5-(1,1-dimethylpropylimidazole
2,5-di(1,1-dimethylbutyl)-4-(1,1-dimethylpropyl)imidazole
2-(1,1-dimethylbutyl)-4-(1,1-dimethylpropyl)-5-(1,1-dimethylpentyl)imidazole
2-(1,1-dimethylbutyl)-4-(1,1-dimethylpentyl)-5-(1,1-dimethylpropyl)imidazole
2-(1,1-dimethylbutyl)-4-(1,1-dimethylpropyl)-5-(1,1-dimethylhexyl)imidazole
2-(1,1-dimethylbutyl)-4-(1,1-dimethylhexyl)-5-(1,1-dimethylpropyl)imidazole
2,4-(1,1-dimethylbutyl)-5-(1,1-dimethylbutyl)imidazole
2,5-(1,1-dimethylbutyl)-4-(1,1-dimethylbutyl)imidazole
2-(1,1-dimethylbutyl)-4-(1,1-dimethylpentyl)-5-(1,1-dimethylhexyl)imidazole
2-(1,1-dimethylbutyl)-4-(1,1-dimethylhexyl)-5-(1,1-dimethylpentyl)imidazole
2-(1,1-dimethylpentyl)-4-tert-butyl-5-(1,1-dimethylpropyl)imidazole
2-(1,1-dimethylpentyl)-4-(1,1-dimethylpropyl)-5-tert-butyl-imidazole
2-(1,1-dimethylpentyl)-4-tert-butyl-5-(1,1-dimethylbutyl)imidazole
2-(1,1-dimethylpentyl)-4-(1,1-dimethylbutyl)-5-tert-butyl-imidazole
2-(1,1-dimethylpentyl)-4-tert-butyl-5-(1,1-dimethylpentyl)imidazole
2-(1,1-dimethylpentyl)-4-(1,1-dimethylpentyl)-5-tert-butyl-imidazole
2-(1,1-dimethylpentyl)-4-tert-butyl-5-(1,1-dimethylhexyl)imidazole
2-(1,1-dimethylpentyl)-4-(1,1-dimethylhexyl)-5-tert-butyl imidazole
2-(1,1-dimethylpentyl)-4-(1,1-dimethylpropyl)-5-(1,1-dimethylbutyl)imidazole
2-(1,1-dimethylpentyl)-4-(1,1-dimethylbutyl)-5-(1,1-dimethylpropyl)imidazole
2,4-di-(1,1-dimethylpentyl)-5-(1,1-dimethylpropyl)imidazole
2,5-di-(1,1-dimethylpentyl)-4-(1,1-dimethylpropyl)imidazole
2-(1,1-dimethylpentyl)-4-(1,1-dimethylpropyl)-5-(1,1-dimethylhexyl)imidazole
2-(1,1-dimethylpentyl)-4-(1,1-dimethylhexyl)-5-(1,1-dimethylpropyl)imidazole
2,4-(1,1-dimethylpentyl)-5-(1,1-dimethylbutyl)imidazole
2,5-(1,1-dimethylpentyl)-4-(1,1-dimethylbutyl)imidazole
2,4-(1,1-dimethylpentyl)-5-(1,1-dimethylhexyl)imidazole
2,5-(1,1-dimethylpentyl)-4-(1,1-dimethylhexyl)imidazole
2-(1,1-dimethylhexyl)-4-tert-butyl-5-(1,1-dimethylpropyl)imidazole 2-(1,1-dimethylhexyl)-4-(1,1-dimethylpropyl)-5-tert-butyl-imidazole
2-(1,1-dimethylhexyl)-4-tert-butyl-5-(1,1-dimethyl butyl)imidazole
2-(1,1-dimethylhexyl)-4-(1,1-dimethyl butyl)-5-tert-butyl-imidazole
2-(1,1-dimethylhexyl)-4-tert-butyl-5-(1,1-dimethyl pentyl)imidazole
2-(1,1-dimethylhexyl)-4-(1,1-dimethyl pentyl)-5-tert-butyl-imidazole
2-(1,1-dimethylhexyl)-4-tert-butyl-5-(1,1-dimethyl hexyl)imidazole
2-(1,1-dimethylhexyl)-4-(1,1-dimethyl hexyl)-5-tert-butyl-imidazole
2-(1,1-dimethylhexyl)-4-(1,1-dimethylpropyl)-5-(1,1-dimethyl butyl)imidazole
2-(1,1-dimethylhexyl)-4-(1,1-dimethyl butyl)-5-(1,1-dimethylpropyl)imidazole
2-(1,1-dimethylhexyl)-4-(1,1-dimethylpropyl)-5-(1,1-dimethyl pentyl)imidazole
2-(1,1-dimethylhexyl)-4-(1,1-dimethyl pentyl)-5-(1,1-dimethylpropyl)imidazole
2,4-di(1,1-dimethylhexyl)-5-(1,1-dimethylpropyl)imidazole
2,5-di(1,1-dimethylhexyl)-4-(1,1-dimethylpropyl)imidazole
2-(1,1-dimethylhexyl)-4-(1,1-dimethylpentyl)-5-(1,1-dimethyl butyl)imidazole
2-(1,1-dimethylhexyl)-4-(1,1-dimethyl butyl)-5-(1,1-dimethylpentyl)imidazole
2,4-di(1,1-dimethylhexyl)-5-(1,1-dimethylpentyl)imidazole
2,5-di(1,1-dimethylhexyl)-4-(1,1-dimethylpentyl)imidazole
2-(1-methylethyl)-4,5-di-tert-butylimidazole
2-(1-methylethyl)-4,5-di(1,1-dimethylpropyl)imidazole
2-(1-methylethyl)-4,5-di(1,1-dimethylbutyl)imidazole
2-(1-methylethyl)-4,5-di(1,1-dimethylpentyl)imidazole
2-(1-methylethyl)-4,5-di(1,1-dimethylhexyl)imidazole
2,4,5-tri(1-methylethyl)imidazole
2-(1-methylethyl)-4-tert-butyl-5-(1,1-dimethylpropyl)imidazole
2-(1-methylethyl)-4-(1,1-dimethylpropyl)-5-tert-butylimidazole
2-(1-methylethyl)-4-(1,1-dimethylbutyl)-5-tert-butylimidazole
2-(1-methylethyl)-4-tert-butylimidazole-5-(1,1-dimethylbutyl)imidazole
2-(1-methylethyl)-4-(1,1-dimethylpentyl)-5-tert-butylimidazole
2-(1-methylethyl)-4-tert-butylimidazole-5-(1,1-dimethylpentyl)imidazole
2-(1-methylethyl)-4-(1,1-dimethylhexyl)-5-tert-butylimidazole
2-(1-methylethyl)-4-tert-butylimidazole-5-(1,1-dimethylhexyl)imidazole
2-(1-methylethyl)-4-(1,1-dimethylhexyl)-5-tert-butylimidazole
2-(1-methylethyl)-4-(1,1-dimethylpropyl)-5-(1,1-dimethylbutyl)imidazole
2-(1-methylethyl)-4-(1,1-dimethylbutyl)-5-(1,1-dimethylpropyl)-imidazole
2-(1-methylethyl)-4-(1,1-dimethylpropyl)-5-(1,1-dimethylpentyl)imidazole
2-(1-methylethyl)-4-(1,1-dimethylpentyl)-5-(1,1-dimethylpropyl)-imidazole
2-(1-methylethyl)-4-(1,1-dimethylpropyl)-5-(1,1-dimethylhexyl)imidazole
2-(1-methylethyl)-4-(1,1-dimethylhexyl)-5-(1,1-dimethylpropyl)-imidazole
2-(1-methylethyl)-4-(1,1-dimethylpentyl)-5-(1,1-dimethylbutyl)-imidazole
2-(1-methylethyl)-4-(1,1-dimethylbutyl)-5-(1,1-dimethylpentyl)-imidazole
2-(1-methylethyl)-4-(1,1-dimethylpentyl)-5-(1,1-dimethylhexyl)-imidazole
2-(1-methylethyl)-4-(1,1-dimethylhexyl)-5-(1,1-dimethylpentyl)-imidazole
2,4-di-tert-butyl-5-(1-methylethyl)imidazole
2,5-di-tert-butyl-4-(1-methylethyl)imidazole
2-tert-butyl-4-(1,1-dimethylpropyl)-5-(1-methylethyl)imidazole
2-tert-butyl-4-(1-methylethyl)-5-(1,1-dimethylbutyl)imidazole
2-tert-butyl-4-(1,1-dimethylbutyl)-5-(1-methylethyl)imidazole
2-tert-butyl-4-(1-methylethyl)-5-(1,1-dimethylpentyl)imidazole
2-tert-butyl-4-(1,1-dimethylpentyl)-5-(1-methylethyl)imidazole
2-tert-butyl-4-(1-methylethyl)-5-(1,1-dimethylhexyl)imidazole
2-tert-butyl-4-(1,1-dimethylhexyl)-5-(1-methylethyl)imidazole
2-(1,1-dimethylpropyl)-4-tert-butyl-5-(1-methylethyl)imidazole
2-(1,1-dimethylpropyl)-4-(1-methylethyl)-5-tert-butylimidazole
2-(1,1-dimethylpropyl)-4-tert-butyl-5-(1-methylethyl)imidazole
2,4-di(1,1-dimethylpropyl)-5-(1-methylethyl)-imidazole
2,5-di(1,1-dimethylpropyl)-4-(1-methylethyl)-imidazole
2-(1,1-dimethylpropyl)-4-(1,1-dimethylethyl)-5-(1,1-dimethylbutyl)imidazole
2-(1,1-dimethylpropyl)-4-(1,1-dimethylbutyl)-5-(1,1-dimethylethyl)imidazole
2-(1,1-dimethylpropyl)-4-(1,1-dimethylethyl)-5-(1,1-dimethylpentyl)imidazole
2-(1,1-dimethylpropyl)-4-(1,1-dimethylpentyl)-5-(1,1-dimethylethyl)imidazole
2-(1,1-dimethylpropyl)-4-(1,1-dimethylethyl)-5-(1,1-dimethylhexyl)imidazole
2-(1,1-dimethylpropyl)-4-(1,1-dimethylhexyl)-5-(1,1-dimethylethyl)imidazole
2-(1,1-dimethylbutyl)-4-tert-butyl-5-(1-methylethyl)imidazole
2-(1,1-dimethylbutyl)-4-(1-methylethyl)-5-tert-butyl-5-imidazole
2-(1,1-dimethylbutyl)-4-(1-methylethyl)-5-(1,1-dimethylpropyl)imidazole
2-(1,1-dimethylbutyl)-4-(1,1-dimethylpropyl)-5-(1-methylethyl)imidazole
2-(1,1-dimethylbutyl)-4-(1-methylethyl)-5-(1,1-dimethylbutyl)imidazole
2-(1,1-dimethylbutyl)-4-(1,1-dimethylbutyl)-5-(1-methylethyl)imidazole
2-(1,1-dimethylbutyl)-4-(1-methylethyl)-5-(1,1-dimethylpentyl)imidazole
2-(1,1-dimethylbutyl)-4-(1,1-dimethylpenyl)-5-(1-methylethyl)imidazole
2-(1,1-dimethylbutyl)-4-(1-methylethyl)-5-(1,1-dimethylhexyl)imidazole
2-(1,1-dimethylbutyl)-4-(1,1-dimethylhexyl)-5-(1-methylethyl)imidazole
2-(1,1-dimethylpentyl)-4-(1,1-dimethylethyl)-5-tert-butyl-imidazole 2-(1,1-dimethylpentyl)-4-tert-butyl-5-(1,1-dimethylethyl)imidazole
2-(1,1-dimethylpentyl)-4-(1,1-dimethylethyl)-5-tert-butylimidazole
2-(1,1-dimethylpentyl)-4-(1,1-dimethylpropyl)-5-(1,1-dimethylethyl)imidazole
2-(1,1-dimethylpentyl)-4-(1,1-dimethylethyl)-5-(1,1-dimethylpropyl)-5-midazole
2-(1,1-dimethylpentyl)-4-(1,1-dimethylbutyl)-5-(1,1-dimethylethyl)imidazole
2-(1,1-dimethylpentyl)-4-(1,1-dimethylethyl)-5-(1,1-dimethylbutyl)-5-midazole
2-(1,1-dimethylpentyl)-4-(1,1-dimethylbutyl)-5-(1,1-dimethylethyl)imidazole
2,4-di(1,1-dimethylpentyl)-5-(1,1-dimethylethyl)imidazole
2,5-di(1,1-dimethylpentyl)-4-(1,1-dimethylethyl)imidazole
2-(1,1-dimethylpentyl)-4-(1,1-dimethylethyl)-5-(1,1-dimethylhexyl)-5-midazole
2-(1,1-dimethylpentyl)-4-(1,1-dimethylhexyl)-5-(1,1-dimethylethyl)imidazole
2-(1,1-dimethylhexyl)-4-tert-butyl-5-(1,1-dimethylethyl)imidazole
2-(1,1-dimethylhexyl)-4-(1,1-dimethylethyl)-5-tert-butylimidazole
2-(1,1-dimethylhexyl)-4-(1,1-dimethylpropyl)-5-(1,1-dimethylethyl)imidazole
2-(1,1-dimethylhexyl)-4-(1,1-dimethylethyl)-5-(1,1-dimethylpropyl)imidazole
2-(1,1-dimethylhexyl)-4-(1,1-dimethylbutyl)-5-(1-methylethyl)imidazole
2-(1,1-dimethylhexyl)-4-(1-methylethyl)-5-(1,1-dimethylbutyl)-5 imidazole
2-(1,1-dimethylhexyl)-4-(1,1-dimethylpentyl)-5-(1-methylethyl)imidazole
2-(1,1-dimethylhexyl)-4-(1-methylethyl)-5-(1,1-dimethylpentyl)imidazole
2,4-di(1,1-dimethylhexyl)-5-(1-methylethyl)imidazole
2,5-di(1,1-dimethylhexyl)-4-(1-methylethyl)imidazole
2,4-(1-methylethyl)-5-tert-butylimidazole
2,5-(1-methylethyl)-4-tert-butylimidazole
2,4-(1-methylethyl)-5-(1,1-dimethylpropyl)imidazole
2,5-(1-methylethyl)-4-(1,1-dimethylpropyl)imidazole
2,4-(1-methylethyl)-5-(1,1-dimethylbutyl)imidazole
2,5-(1-methylethyl)-4-(1,1-dimethylbutyl)imidazole
2,4-(1-methylethyl)-5-(1,1-dimethylpentyl)imidazole
2,5-(1-methylethyl)-4-(1,1-dimethylpentyl)imidazole
2,4-(1-methylethyl)-5-(1,1-dimethylhexyl)imidazole
2,5-(1-methylethyl)-4-(1,1-dimethylhexyl)imidazole
2-(1,2-dimethylpropyl)-4,5-di-tert-butylimidazole
2-(1,2-dimethylpropyl)-4,5-di-(1,1-dimethylpropyl)imidazole
2-(1,2-dimethylpropyl)-4,5-di-(1,1-dimethylbutyl)imidazole
2-(1,2-dimethylpropyl)-4,5-di-(1,1-dimethylpentyl)imidazole
2-(1,2-dimethylpropyl)-4,5-di-(1,1-dimethylhexyl)imidazole
2-(1,2-dimethylpropyl)-4,5-di-(1-methylethyl)imidazole
2-(1,2-dimethylpropyl)-4-tert-butyl-5-(1,1-dimethylpropyl)imidazole
2-(1,2-dimethylpropyl)-4-(1,1-dimethylpropyl)-5-tert-butylimidazole
2-(1,2-dimethylpropyl)-4-tert-butyl-5-(1,1-dimethylbutyl)imidazole
2-(1,2-dimethylpropyl)-4-(1,1-dimethylbutyl)-5-tert-butylimidazole
2-(1,2-dimethylpropyl)-4-tert-butyl-5-(1,1-dimethypentyl)imidazole
2-(1,2-dimethylpropyl)-4-(1,1-dimethypentyl)-5-tert-butylimidazole
2-(1,2-dimethylpropyl)-4-tert-butyl-5-(1,1-dimethyhexyl)imidazole
2-(1,2-dimethylpropyl)-4-(1,1-dimethyhexyl)-5-tert-butylimidazole
2-(1,2-dimethylpropyl)-4-(1,1-dimethylpropyl)-5-(1,1-dimethylbutyl)imidazole
2-(1,2-dimethylpropyl)-4-(1,1-dimethylbutyl)-5-(1,1-dimethylpropyl)imidazole
2-(1,2-dimethylpropyl)-4-(1,1-dimethylpropyl)-5-(1,1-dimethypentyl)imidazole
2-(1,2-dimethylpropyl)-4-(1,1-dimethypentyl)-5-(1,1-dimethylpropyl)imidazole
2-(1,2-dimethylpropyl)-4-(1,1-dimethylpropyl)-5-(1,1-dimethyhexyl)imidazole
2-(1,2-dimethylpropyl)-4-(1,1-dimethyhexyl)-5-(1,1-dimethylpropyl)imidazole
2-(1,2-dimethylpropyl)-4-(1,1-dimethypentyl)-5-(1,1-dimethylbutyl)imidazole
2-(1,2-dimethylpropyl)-4-(1,1-dimethylbutyl)-5-(1,1-dimethypentyl)imidazole
2-(1,2-dimethylpropyl)-4-(1,1-dimethyhexyl)-5-(1,1-dimethylbutyl)imidazole
2-(1,2-dimethylpropyl)-4-(1,1-dimethylbutyl)-5-(1,1-dimethyhexyl)imidazole
2-(1,2-dimethylpropyl)-4-tert-butyl-5-(1-methyethyl)imidazole
2-(1,2-dimethylpropyl)-4-(1-methyethyl)-5-tert-butylimidazole
2-(1,2-dimethylpropyl)-4-tert-butyl-5-(1-methyethyl)imidazole
2-(1,2-dimethylpropyl)-4-(1-methyethyl)-5-(1,1-dimethylpropyl)imidazole
2-(1,2-dimethylpropyl)-4-(1,1-dimethylpropyl)-(1-methyethyl)imidazole
2-(1,2-dimethylpropyl)-4-(1-methyethyl)-5-(1,1-dimethylbutyl)imidazole
2-(1,2-dimethylpropyl)-4-(1,1-dimethylbutyl)-(1-methyethyl)imidazole
2-(1,2-dimethylpropyl)-4-(1-methyethyl)-5-(1,1-dimethylpentyl)imidazole
2-(1,2-dimethylpropyl)-4-(1,1-dimethylpentyl)-5-(1-methyethyl)imidazole
2-(1,2-dimethylpropyl)-4-(1-methyethyl)-5-(1,1-dimethylhexyl)imidazole
2-(1,2-dimethylpropyl)-4-(1,1-dimethylhexyl)-5-(1-methyethyl)imidazole
2,4-di-tert-butyl-5-(1,2-dimethylpropyl)imidazole
2,5-di-tert-butyl-4-(1,2-dimethylpropyl)imidazole
2-tert-butyl-4-(1,1-dimethylpropyl)-5-(1,2-dimethylpropyl)imidazole
2-tert-butyl-4-(1,2-dimethylpropyl)-5-(1,1-dimethylpropyl)imidazole
2-tert-butyl-4-(1,1-dimethylbutyl)-5-(1,2-dimethylpropyl)imidazole
2-tert-butyl-4-(1,2-dimethylpropyl)-5-(1,1-dimethylbutyl)imidazole
2-tert-butyl-4-(1,1-dimethylpentyl)-5-(1,2-dimethylpropyl)imidazole
2-tert-butyl-4-(1,2-dimethylpropyl)-5-(1,1-dimethylpentyl)imidazole
2-tert-butyl-4-(1,1-dimethylhexyl)-5-(1,2-dimethylpropyl)imidazole 2-tert-butyl-4-(1,2-dimethylpropyl)-5-(1,1-dimethylhexyl)imidazole
2-tert-butyl-4-(1-methylethyl)-5-(1,2-dimethylpropyl)imidazole
2-tert-butyl-4-(1,2-dimethylpropyl)-5-(1-methylethyl)imidazole
2-(1,1-dimethylpropyl)-4-tert-butyl-5-(1,2-dimethylpropyl)imidazole
2-(1,1-dimethylpropyl)-4-(1,2-dimethylpropyl)-5-tert-butylimidazole
2,4-(1,1-dimethylpropyl)-5-(1,2-dimethylpropyl)imidazole
2,5-(1,1-dimethylpropyl)-4-(1,2-dimethylpropyl)imidazole
2-(1,1-dimethylpropyl)-4-(1,2-dimethylpropyl)-5-(1,1-dimethylbutyl)imidazole
2-(1,1-dimethylpropyl)-4-(1,1-dimethylbutyl)-5-(1,2-dimethylpropyl)imidazole
2-(1,1-dimethylpropyl)-4-(1,2-dimethylpropyl)-5-(1,1-dimethylpentyl)imidazole
2-(1,1-dimethylpropyl)-4-(1,1-dimethylpentyl)-5-(1,2-dimethylpropyl)imidazole
2-(1,1-dimethylpropyl)-4-(1,2-dimethylpropyl)-5-(1,1-dimethylhexyl)imidazole
2-(1,1-dimethylpropyl)-4-(1,1-dimethylhexyl)-5-(1,2-dimethylpropyl)imidazole
2-(1,1-dimethylpropyl)-4-(1,2-dimethylpropyl)-5-(1-methylethyl)imidazole
2-(1,1-dimethylpropyl)-4-(1-methylethyl)-5-(1,2-dimethylpropyl)imidazole
2-(1,1-dimethylpropyl)-4-tert-butyl-5-(1,2-dimethylpropyl)imidazole
2-(1,1-dimethylbutyl)-4-(1,2-dimethylpropyl)-5-tert-butylimidazole
2-(1,1-dimethylbutyl)-4-tert-butyl-5-(1,2-dimethylpropyl)-5-imidazole
2-(1,1-dimethylbutyl)-4-(1,2-dimethylpropyl)-5-(1,1-dimethylpropyl)imidazole
2-(1,1-dimethylbutyl)-4-(1,1-dimethylpropyl)-5-(1,2-dimethylpropyl)imidazole
2,4-di(1,1-dimethylbutyl)-5-(1,2-dimethylpropyl)imidazole
2,5-di(1,1-dimethylbutyl)-4-(1,2-dimethylpropyl)imidazole
2-(1,1-dimethylbutyl)-4-(1,1-dimethyl pentyl)-5-(1,2-dimethylpropyl)imidazole
2-(1,1-dimethylbutyl)-4-(1,1-dimethylpropyl)-5-(1,1-dimethylpentyl)-5-imidazole
2-(1,1-dimethylbutyl)-4-(1,1-dimethyl hexyl)-5-(1,2-dimethylpropyl)imidazole
2-(1,1-dimethylbutyl)-4-(1,2-dimethylpropyl)-5-(1,1-dimethylhexyl)-5-imidazole
2-(1,1-dimethylbutyl)-4-(1-methylethyl)-5-(1,2-dimethylpropyl)imidazole
2-(1,1-dimethylbutyl)-4-(1,2-dimethylpropyl)-5-(1-methylethyl)-5-imidazole
2-(1,1-dimethylpentyl)-4-tert-butyl-5-(1,2-dimethylpropyl)imidazole
2-(1,1-dimethylpentyl)-4-(1,2-dimethylpropyl)-5-tert-butylimidazole
2-(1,1-dimethylpentyl)-4-(1,2-dimethylpropyl)-5-(1,1-dimethylpropyl)imidazole
2-(1,1-dimethylpentyl)-4-(1,1-dimethylpropyl)-5-(-1,2-dimethylpropyl)-5imidazole
2-(1,1-dimethylpentyl)-4-(1,2-dimethylpropyl)-5-(1,1-dimethylbutyl)imidazole
2,4-di(1,1-dimethylpentyl)-5-(1,2-dimethylpropyl))imidazole
2,5-di(1,1-dimethylpentyl)-4-(1,2-dimethylpropyl))imidazole
2-(1,1-dimethylpentyl)-4-(1,1-dimethylhexyl)-5-(1,2-dimethylpropyl)imidazole
2-(1,1-dimethylpentyl)-4-(1,2-dimethylpropyl)-5-(1,1-dimethylhexyl)imidazole
2-(1,1-dimethylpentyl)-4-(1-methylethyl)-5-(1,2-dimethylpropyl)imidazole
2-(1,1-dimethylpentyl)-4-(1,2-dimethylpropyl)-5-(1-methylethyl)imidazole
2-(1,1-dimethylhexyl)-4-(1,2-dimethylpropyl)-5-tert-butylimidazole
2-(1,1-dimethylhexyl)-4-tert-butyl-5-(1,2-dimethylpropyl)imidazole
2-(1,1-dimethylhexyl)-4-(1,2-dimethylpropyl)-5-(1,1-dimethylpropyl)imidazole
2-(1,1-dimethylhexyl)-4-(1,1-dimethylpropyl)-5-(1,2-dimethylpropyl)imidazole
2-(1,1-dimethylhexyl)-4-(1,2-dimethylpropyl)-5-(1,1-dimethylbutyl)imidazole
2-(1,1-dimethylhexyl)-4-(1,1-dimethylbutyl)-5-(1,2-dimethylpropyl)imidazole
2-(1,1-dimethylhexyl)-4-(1,2-dimethylpropyl)-5-(1,1-dimethylpentyl)imidazole
2-(1,1-dimethylhexyl)-4-(1,1-dimethylpentyl)-5-(1,2-dimethylpropyl)imidazole
2,4-di(1,1-dimethylhexyl)-5-(1,2-dimethylpropyl)imidazole
2,5-di(1,1-dimethylhexyl)-4-(1,2-dimethylpropyl)imidazole
2-(1,1-dimethylhexyl)-4-(1,2-dimethylpropyl)-5-(1-methylethyl)imidazole
2-(1,1-dimethylhexyl)-4-(1-methylethyl)-5-(1,2-dimethylpropyl)imidazole
2-(1-methylethyl)-4-tert-butyl-5-(1,2-dimethylpropyl)imidazole
2-(1-methylethyl)-4-(1,2-dimethylpropyl)-5-tert-butyl-imidazole
2-(1-methylethyl)-4-tert-butyl-5-(1,2-dimethylpropyl)imidazole
2-(1-methylethyl)-4-(1,2-dimethylpropyl)-5-(1,1-dimethylpropyl)imidazole
2-(1-methylethyl)-4-(1,1-dimethylpropyl)-5-(1,2-dimethylpropyl)imidazole
2-(1-methylethyl)-4-(1,2-dimethylpropyl)-5-(1,1-dimethylbutyl)imidazole
2-(1-methylethyl)-4-(1,1-dimethylbutyl)-5-(1,2-dimethylpropyl)imidazole
2-(1-methylethyl)-4-(1,2-dimethylpropyl)-5-(1,1-dimethylpentyl)imidazole
2-(1-methylethyl)-4-(1,1-dimethylpentyl)-5-(1,2-dimethylpropyl)imidazole
2-(1-methylethyl)-4-(1,2-dimethylpropyl)-5-(1,1-dimethylhexyl)imidazole
2-(1-methylethyl)-4-(1,1-dimethylhexyl)-5-(1,2-dimethylpropyl)imidazole
2,4-di(1-methylethyl)-5-(1,2-dimethylpropyl)imidazole
2,5-di(1-methylethyl)-4-(1,2-dimethylpropyl)imidazole
2,4-di(1,2-dimethylpropyl)-5-tert-butylimidazole
2,5-di(1,2-dimethylpropyl)-4-tert-butylimidazole
2,4-di(1,2-dimethylpropyl)-5-(1,1-dimethylpropyl)imidazole
2,5-di(1,2-dimethylpropyl)-4-(1,1-dimethylpropyl)imidazole
2,4-di(1,2-dimethylpropyl)-5-(1,1-dimethylbutyl)imidazole
2,5-di(1,2-dimethylpropyl)-4-(1,1-dimethylbutyl)imidazole
2,4-di(1,2-dimethylpropyl)-5-(1,1-dimethylpentyl)imidazole
2,5-di(1,2-dimethylpropyl)-4-(1,1-dimethylpentyl)imidazole
2,4-di(1,2-dimethylpropyl)-5-(1,1-dimethylhexyl)imidazole 2,5-di(1,2-dimethylpropyl)-4-(1,1-dimethylhexyl)imidazole
2,4-di(1,2-dimethylpropyl)-5-(1-methylethyl)imidazole
2,5-di(1,2-dimethylpropyl)-4-(1-methylethyl)imidazole
Preferably the imidazole is
2,4,5-tri-tert-butylimidazole
2-tert-butyl-4,5-di-(1,1-dimethylpropyl)imidazole
2-tert-butyl-4,5-di-(1,1-dimethylbutyl)imidazole
2-tert-butyl-4,5-di-(1,1-dimethylpentyl)imidazole 2-tert-butyl-4,5-di-(1,1-dimethylhexyl)imidazole
2-(1,1-dimethylpropyl)-4,5-di-tert-butylimidazole
2,4,5-tri-(1,1-dimethylpropyl)imidazole
2-(1,1-dimethylpropyl)-4,5-di-(1,1-dimethylbutyl)imidazole
2-(1,1-dimethylpropyl)-4,5-di-(1,1-dimethylpentyl)imidazole
2-(1,1-dimethylpropyl)-4,5-di-(1,1-dimethylhexyl)imidazole
2-(1,1-dimethylbutyl)-4,5-di-tert-butylimidazole
2-(1,1-dimethylbutyl)-4,5-di-(1,1-dimethylpropyl)
2,4,5-tri-(1,1-dimethylbutyl)imidazole
2-(1,1-dimethylbutyl)-4,5-di-(1,1-dimethylpentyl)imidazole
2-(1,1-dimethylbutyl)-4,5-di-(1,1-dimethylhexyl)imidazole
2-(1,1-dimethylpentyl)-4,5-di-tert-butylimidazole
2-(1,1-dimethylpentyl)-4,5-di-(1,1-dimethylpropyl)limidazole
2-(1,1-dimethylpentyl)-4,5-di-(1,1-dimethylbutyl)limidazole
2,4,5-tri-(1,1-dimethylpentyl)imidazole
2-(1,1-dimethylpentyl)-4,5-di-(1,1-dimethylhexyl)limidazole
2-(1,1-dimethyl hexyl)-4,5-di-tert-butylimidazole
2-(1,1-dimethylhexyl)-4,5-di-(1,1-dimethylpropyl)imidazole
2-(1,1-dimethylhexyl)-4,5-di-(1,1-dimethylbutyl)imidazole
2-(1,1-dimethylhexyl)-4,5-di-(1,1-dimethylpentyl)imidazole
2,4,5-tri-(1,1-dimethylhexyl)imidazole
2,4-di-tert-butyl-5-(1,1-dimethylpropyl)imidazole
2,5-di-tert-butyl-4-(1,1-dimethylpropyl)imidazole
2,4-di-tert-butyl-5-(1,1-dimethylbutyl)imidazole
2,5-di-tert-butyl-4-(1,1-dimethylbutyl)imidazole
2,4-di-tert-butyl-5-(1,1-dimethylpentyl)imidazole
2,5-di-tert-butyl-4-(1,1-dimethylpentyl)imidazole
2,4-di-tert-butyl-5-(1,1-dimethylhexyl)imidazole
2,5-di-tert-butyl-4-(1,1-dimethylhexyl)imidazole
2-tert-butyl-4-(1,1-dimethylpropyl)-5-(1,1-dimethylbutyl)imidazole
2-tert-butyl-4-(1,1-dimethylbutyl)-5-(1,1-dimethylpropyl)imidazole
2-tert-butyl-4-(1,1-dimethylpropyl)-5-(1,1-dimethylpentyl)imidazole
2-tert-butyl-4-(1,1-dimethylpentyl)-5-(1,1-dimethylpropyl)imidazole
2-tert-butyl-4-(1,1-dimethylpropyl)-5-(1,1-dimethylhexyl)imidazole
2-tert-butyl-4-(1,1-dimethylhexyl)-5-(1,1-dimethylpropyl)imidazole
2-tert-butyl-4-(1,1-dimethylpentyl)-5-(1,1-dimethylbutyl)imidazole
2-tert-butyl-4-(1,1-dimethylbutyl)-5-(1,1-dimethylpentyl)imidazole
2-tert-butyl-4-(1,1-dimethylpentyl)-5-(1,1-dimethylhexyl)imidazole
2-tert-butyl-4-(1,1-dimethylhexyl)-5-(1,1-dimethylpentyl)imidazole
2-(1,1-dimethylpropyl)-4-tert-butyl-5-(1,1-dimethylpropyl)imidazole
2-(1,1-dimethylpropyl)-4-(1,1-dimethylpropyl)-5-tert-butyl-imidazole
2-(1,1-dimethylpropyl)-4-tert-butyl-5-(1,1-dimethylbutyl)imidazole
2-(1,1-dimethylpropyl)-4-(1,1-dimethylbutyl)-5-tert-butyl-imidazole
2-(1,1-dimethylpropyl)-4-tert-butyl-5-(1,1-dimethylpentyl)imidazole
2-(1,1-dimethylpropyl)-4-(1,1-dimethylpentyl)-5-tert-butyl-imidazole
2-(1,1-dimethylpropyl)-4-tert-butyl-5-(1,1-dimethylhexyl)imidazole
2-(1,1-dimethylpropyl)-4-(1,1-dimethylhexyl)-5-tert-butyl-imidazole
2,4-di-(1,1-dimethylpropyl)-5-(1,1-dimethylbutyl)imidazole
2,5-di-(1,1-dimethylpropyl)-4-(1,1-dimethylbutyl)imidazole
2,4-di-(1,1-dimethylpropyl)-5-(1,1-dimethylpentyl)imidazole
2,5-di-(1,1-dimethylpropyl)-4-(1,1-dimethylpentyl)imidazole
2,4-di-(1,1-dimethylpropyl)-5-(1,1-dimethylhexyl)imidazole
2,5-di-(1,1-dimethylpropyl)-4-(1,1-dimethylhexyl)imidazole
2-(1,1-dimethylpropyl)-4-(1,1-dimethylpentyl)-5-(1,1-dimethylbutyl)imidazole
2-(1,1-dimethylpropyl)-4-(1,1-dimethylbutyl)-5-(1,1-dimethylpentyl)imidazole
2-(1,1-dimethylpropyl)-4-(1,1-dimethylpentyl)-5-(1,1-dimethylhexyl)imidazole
2-(1,1-dimethylpropyl)-4-(1,1-dimethylhexyl)-5-(1,1-dimethylpentyl)imidazole
2-(1,1-dimethylbutyl)-4-tert-butyl-5-(1,1-dimethyl butyl) imidazole
2-(1,1-dimethylbutyl)-4-(1,1-dimethyl butyl)-5-tert-butyl-imidazole
2,4-di(1,1-dimethylbutyl)-5-tert-butyl-imidazole
2,5-di(1,1-dimethylbutyl)-4-tert-butyl-imidazole
2-(1,1-dimethylbutyl)-4-tert-butyl-5-(1,1-dimethyl pentyl) imidazole
2-(1,1-dimethyl butyl)-4-(1,1-dimethylpentyl)-5-tert-butyl imidazole
2-(1,1-dimethylbutyl)-4-tert-butyl-5-(1,1-dimethylhexyl) imidazole
2-(1,1-dimethylbutyl)-4-(1,1-dimethylhexyl)-5-tert-butyl-imidazole
2,4-di(1,1-dimethylbutyl)-5-(1,1-dimethylpropylimidazole
2,5-di(1,1-dimethylbutyl)-4-(1,1-dimethylpropyl)imidazole
2-(1,1-dimethylbutyl)-4-(1,1-dimethylpropyl)-5-(1,1-dimethylpentyl)imidazole
2-(1,1-dimethylbutyl)-4-(1,1-dimethylpentyl)-5-(1,1-dimethylpropyl)imidazole
2-(1,1-dimethylbutyl)-4-(1,1-dimethylpropyl)-5-(1,1-dimethylhexyl)imidazole
2-(1,1-dimethylbutyl)-4-(1,1-dimethylhexyl)-5-(1,1-dimethylpropyl)imidazole
2,4-(1,1-dimethylbutyl)-5-(1,1-dimethylbutyl)imidazole
2,5-(1,1-dimethylbutyl)-4-(1,1-dimethylbutyl)imidazole
2-(1,1-dimethylbutyl)-4-(1,1-dimethylpentyl)-5-(1,1-dimethylhexyl)imidazole
2-(1,1-dimethylbutyl)-4-(1,1-dimethylhexyl)-5-(1,1-dimethylpentyl)imidazole
2-(1,1-dimethylpentyl)-4-tert-butyl-5-(1,1-dimethylpropyl) imidazole 2-(1,1-dimethylpentyl)-4-(1,1-dimethylpropyl)-5-tert-butyl-imidazole
2-(1,1-dimethylpentyl)-4-tert-butyl-5-(1,1-dimethylbutyl)imidazole
2-(1,1-dimethylpentyl)-4-(1,1-dimethylbutyl)-5-tert-butyl-imidazole
2-(1,1-dimethylpentyl)-4-tert-butyl-5-(1,1-dimethylpentyl)imidazole
2-(1,1-dimethylpentyl)-4-(1,1-dimethylpentyl)-5-tert-butyl-imidazole
2-(1,1-dimethylpentyl)-4-tert-butyl-5-(1,1-dimethylhexyl)imidazole
2-(1,1-dimethylpentyl)-4-(1,1-dimethylhexyl)-5-tert-butyl-imidazole
2-(1,1-dimethylpentyl)-4-(1,1-dimethylpropyl)-5-(1,1-dimethylbutyl)imidazole
2-(1,1-dimethylpentyl)-4-(1,1-dimethylbutyl)-5-(1,1-dimethylpropyl)imidazole
2,4-di-(1,1-dimethylpentyl)-5-(1,1-dimethylpropyl)imidazole
2,5-di-(1,1-dimethylpentyl)-4-(1,1-dimethylpropyl)imidazole
2-(1,1-dimethylpentyl)-4-(1,1-dimethylpropyl)-5-(1,1-dimethylhexyl)imidazole
2-(1,1-dimethylpentyl)-4-(1,1-dimethylhexyl)-5-(1,1-dimethylpropyl)imidazole
2,4-(1,1-dimethylpentyl)-5-(1,1-dimethylbutyl)imidazole
2,5-(1,1-dimethylpentyl)-4-(1,1-dimethylbutyl)imidazole
2,4-(1,1-dimethylpentyl)-5-(1,1-dimethylhexyl)imidazole
2,5-(1,1-dimethylpentyl)-4-(1,1-dimethylhexyl)imidazole
2-(1,1-dimethylhexyl)-4-tert-butyl-5-(1,1-dimethylpropyl)imidazole
2-(1,1-dimethylhexyl)-4-(1,1-dimethylpropyl)-5-tert-butyl-imidazole
2-(1,1-dimethylhexyl)-4-tert-butyl-5-(1,1-dimethyl butyl)imidazole
2-(1,1-dimethylhexyl)-4-(1,1-dimethyl butyl)-5-tert-butyl-imidazole
2-(1,1-dimethylhexyl)-4-tert-butyl-5-(1,1-dimethyl pentyl)imidazole
2-(1,1-dimethylhexyl)-4-(1,1-dimethyl pentyl)-5-tert-butyl-imidazole
2-(1,1-dimethylhexyl)-4-tert-butyl-5-(1,1-dimethyl hexyl)imidazole
2-(1,1-dimethylhexyl)-4-(1,1-dimethyl hexyl)-5-tert-butyl-imidazole
2-(1,1-dimethylhexyl)-4-(1,1-dimethylpropyl)-5-(1,1-dimethyl butyl)imidazole
2-(1,1-dimethylhexyl)-4-(1,1-dimethyl butyl)-5-(1,1-dimethylpropyl)imidazole
2-(1,1-dimethylhexyl)-4-(1,1-dimethylpropyl)-5-(1,1-dimethyl pentyl)imidazole
2-(1,1-dimethylhexyl)-4-(1,1-dimethyl pentyl)-5-(1,1-dimethylpropyl)imidazole
2,4-di(1,1-dimethylhexyl)-5-(1,1-dimethylpropyl)imidazole
2,5-di(1,1-dimethylhexyl)-4-(1,1-dimethylpropyl)imidazole
2-(1,1-dimethylhexyl)-4-(1,1-dimethylpentyl)-5-(1,1-dimethyl butyl)imidazole
2-(1,1-dimethylhexyl)-4-(1,1-dimethyl butyl)-5-(1,1-dimethylpentyl)imidazole
2,4-di(1,1-dimethylhexyl)-5-(1,1-dimethylpentyl)imidazole
2,5-di(1,1-dimethylhexyl)-4-(1,1-dimethylpentyl)imidazole
Preferably the imidazole is
2,4,5-tri-tert-butylimidazole
2-tert-butyl-4,5-di-(1,1-dimethylpropyl)imidazole
2-(1,1-dimethylbutyl)-4,5-di-tert-butylimidazole
2-(1,1-dimethylbutyl)-4,5-di-(1,1-dimethylpropyl)imidazole
2-tertbutyl-4,5-di(1-methyl-1-ethylpropyl)imidazole
2-(1,1-dimethylpropyl)-4,5-di(1-methyl-1-ethylpropyl)imidazole
2-(1,1-dimethylbutyl)-4,5-di(1-methyl-1-ethylpropyl)imidazole
2-(1,1-dimethylpentyl)-4,5-di(1-methyl-1-ethylpropyl)imidazole
2-(1,1-dimethylhexyl)-4,5-di(1-methyl-1-ethylpropyl)imidazole
2-(1,1-dimethylhexyl)-4,5-di(1-methyl-1-ethylpropyl)imidazole
2-(1-methylethyl)-4,5-di(1-methyl-1-ethylpropyl)imidazole
2,4,5-tri(1-methyl-1-ethylpropyl)imidazole
2,4-di-ter-butyl-5-(1-methyl-1-ethylpropyl)imidazole
2,5-di-ter-butyl-4-(1-methyl-1-ethylpropyl)imidazole
2-tert-butyl-4-(1,1-dimethylpropyl)-5-(1-methyl-1-ethylpropyl)imidazole
2-tert-butyl-5-(1,1-dimethylpropyl)-4-(1-methyl-1-ethylpropyl)imidazole
2-tert-butyl-4-(1,1-dimethylbutyl)-5-(1-methyl-1-ethylpropyl)imidazole
2-tert-butyl-5-(1,1-dimethylbutyl)-4-(1-methyl-1-ethylpropyl)imidazole
2-tert-butyl-4-(1,1-dimethylpentyl)-5-(1-methyl-1-ethylpropyl)imidazole
2-tert-butyl-5-(1,1-dimethylpentyl)-4-(1-methyl-1-ethylpropyl)imidazole
2-tert-butyl-4-(1,1-dimethylhexyl)-5-(1-methyl-1-ethylpropyl)imidazole
2-tert-butyl-5-(1,1-dimethylhexyl)-4-(1-methyl-1-ethylpropyl)imidazole
2-tert-butyl-4-(1-methylpropyl)-5-(1-methyl-1-ethylpropyl)imidazole
2-tert-butyl-5-(1-methylpropyl)-4-(1-methyl-1-ethylpropyl)imidazole
2-tert-butyl-4-(1,2-dimethylpropyl)-5-(1-methyl-1-ethylpropyl)imidazole
2-tert-butyl-5-(1,2-dimethylpropyl)-4-(1-methyl-1-ethylpropyl)imidazole
2-(1,1-dimethylpropyl)-4-tert-butyl-5-(1-methyl-1-ethylpropyl)imidazole
2-(1,1-dimethylpropyl)-5-tert-butyl-4-(1-methyl-1-ethylpropyl)imidazole
2,4-(1,1-dimethylpropyl)-5-(1-methyl-1-ethylpropyl)imidazole
2-(1,1-dimethylpropyl)-4-(1,1-dimethylbutyl)-5-(1-methyl-1-ethylpropyl)imidazole
2-(1,1-dimethylpropyl)-5-(1,1-dimethylbutyl)-4-(1-methyl-1-ethylpropyl)imidazole
2-(1,1-dimethylpropyl)-4-(1,1-dimethylpentyl)-5-(1-methyl-1-ethylpropyl)imidazole
2-(1,1-dimethylpropyl)-5-(1,1-dimethylpentyl)-4-(1-methyl-1-ethylpropyl)imidazole
2-(1,1-dimethylpropyl)-4-(1,1-dimethylhexyl)-5-(1-methyl-1-ethylpropyl)imidazole
2-(1,1-dimethylpropyl)-5-(1,1-dimethyl hexyl)-4-(1-methyl-1-ethylpropyl)imidazole
2-(1,1-dimethylpropyl)-4-(1-methylethyl)-5-(1-methyl-1-ethylpropyl)imidazole
2-(1,1-dimethylpropyl)-5-(1-methylethyl)-4-(1-methyl-1-ethylpropyl)imidazole
2-(1,1-dimethylpropyl)-4-(1,2-dimethylpropyl)-5-(1-methyl-1-ethylpropyl)imidazole
2-(1,1-dimethylpropyl)-5-(1,1-dimethylpropyl)-4-(1-methyl-1-ethylpropyl)imidazole 2-(1,1-dimethylbutyl)-4-tert-butyl-5-(1-methyl-1-ethylpropyl)imidazole
2-(1,1-dimethylbutyl)-5-tert-butyl-4-(1-methyl-1-ethylpropyl)imidazole
2-(1,1-dimethylbutyl)-4-(1,1-dimethylpropyl)-5-(1-methyl-1-ethylpropyl)imidazole
2-(1,1-dimethylbutyl)-5-(1,1-dimethylpropyl)-4-(1-methyl-1-ethylpropyl)imidazole
2,4-di(1,1-dimethylbutyl)-5-(1-methyl-1-ethylpropyl)imidazole
2,5-di(1,1-dimethylbutyl)-4-(1-methyl-1-ethylpropyl)imidazole
2-(1,1-dimethylbutyl)-4-(1,1-dimethylpentyl)-5-(1-methyl-1-ethylpropyl)imidazole
2-(1,1-dimethylbutyl)-5-(1,1-dimethylpentyl)-4-(1-methyl-1-ethylpropyl)imidazole
2-(1,1-dimethylbutyl)-4-(1,1-dimethylhexyl)-5-(1-methyl-1-ethylpropyl)imidazole
2-(1,1-dimethylbutyl)-5-(1,1-dimethylhexyl)-4-(1-methyl-1-ethylpropyl)imidazole
2-(1,1-dimethylbutyl)-4-(1-methylethyl)-5-(1-methyl-1-ethylpropyl)imidazole
2-(1,1-dimethylbutyl)-5-(1-methylethyl)-4-(1-methyl-1-ethylpropyl)imidazole
2-(1,1-dimethylbutyl)-4-(1,2-dimethylpropyl)-5-(1-methyl-1-ethylpropyl)imidazole
2-(1,1-dimethylbutyl)-5-(1,2-dimethylpropyl)-4-(1-methyl-1-ethylpropyl)imidazole
2-(1,1-dimethylpentyl)-4-tert-butyl-5-(1-methyl-1-ethylpropyl)imidazole
2-(1,1-dimethylpentyl)-5-tert-butyl-4-(1-methyl-1-ethylpropyl)imidazole
2-(1,1-dimethylpentyl)-4-(1,1-dimethylpropyl)-5-(1-methyl-1-ethylpropyl)imidazole
2-(1,1-dimethylpentyl)-5-(1,1-dimethylpropyl)-4-(1-methyl-1-ethylpropyl)imidazole
2-(1,1-dimethylpentyl)-4-(1,1-dimethylbutyl)-5-(1-methyl-1-ethylpropyl)imidazole
2-(1,1-dimethylpentyl)-5-(1,1-dimethylbutyl)-4-(1-methyl-1-ethylpropyl)imidazole
2-4-di(1,1-dimethylpentyl)-5-(1-methyl-1-ethylpropyl)imidazole
2-5-di(1,1-dimethylpentyl)-4-(1-methyl-1-ethylpropyl)imidazole
2-(1,1-dimethylpentyl)-4-(1,1-dimethylhexyl)-5-(1-methyl-1-ethylpropyl)imidazole
2-(1,1-dimethylpentyl)-5-(1,1-dimethylhexyl)-4-(1-methyl-1-ethylpropyl)imidazole
2-(1,1-dimethylpentyl)-4-(1-methylethyl)-5-(1-methyl-1-ethylpropyl)imidazole
2-(1,1-dimethylpentyl)-5-(1-methylethyl)-4-(1-methyl-1-ethylpropyl)imidazole
2-(1,1-dimethylpentyl)-4-(1,2-dimethylpropyl)-5-(1-methyl-1-ethylpropyl)imidazole
2-(1,1-dimethylpentyl)-5-(1,2-dimethylpropyl)-4-(1-methyl-1-ethylpropyl)imidazole
2-(1,1-dimethylhexyl)-4-tert-butyl-5-(1-methyl-1-ethylpropyl)imidazole
2-(1,1-dimethylhexyl)-5-tert-butyl-4-(1-methyl-1-ethylpropyl)imidazole
2-(1,1-dimethylhexyl)-4-(1,1-dimethylpropyl)-5-(1-methyl-1-ethylpropyl)imidazole
2-(1,1-dimethylhexyl)-5-(1,1-dimethylpropyl)-4-(1-methyl-1-ethylpropyl)imidazole
2-(1,1-dimethylhexyl)-4-(1,1-dimethylbutyl)-5-(1-methyl-1-ethylpropyl)imidazole
2-(1,1-dimethylhexyl)-5-(1,1-dimethylbutyl)-4-(1-methyl-1-ethylpropyl)imidazole
2-(1,1-dimethylhexyl)-4-(1,1-dimethylpentyl)-5-(1-methyl-1-ethylpropyl)imidazole
2-(1,1-dimethylhexyl)-5-(1,1-dimethylpentyl)-4-(1-methyl-1-ethylpropyl)imidazole
2,4-(1,1-dimethylhexyl)-5-(1-methyl-1-ethylpropyl)imidazole
2,5-(1,1-dimethylhexyl)-4-(1-methyl-1-ethylpropyl)imidazole
2-(1,1-dimethylhexyl)-4-(1-methylethyl)-5-(1-methyl-1-ethylpropyl)imidazole
2-(1,1-dimethylhexyl)-5-(1-methylethyl)-4-(1-methyl-1-ethylpropyl)imidazole
2-(1,1-dimethylhexyl)-4-(1,2-dimethylpropyl)-5-(1-methyl-1-ethylpropyl)imidazole
2-(1,1-dimethylhexyl)-5-(1,2-dimethylpropyl)-4-(1-methyl-1-ethylpropyl)imidazole
2-(1-methylethyl)-4-tert-butyl-5-(1-methyl-1-ethylpropyl)imidazole
2-(1-methylethyl)-5-tert-butyl-4-(1-methyl-1-ethylpropyl)imidazole
2-(1-methylethyl)-4-(1,1-dimethylpropyl)-5-(1-methyl-1-ethylpropyl)imidazole
2-(1-methylethyl)-5-(1,1-dimethylpropyl)-4-(1-methyl-1-ethylpropyl)imidazole
2-(1-methylethyl)-4-(1,1-dimethylbutyl)-5-(1-methyl-1-ethylpropyl)imidazole
2-(1-methylethyl)-5-(1,1-dimethylbutyl)-4-(1-methyl-1-ethylpropyl)imidazole
2-(1-methylethyl)-4-(1,1-dimethylpentyl)-5-(1-methyl-1-ethylpropyl)imidazole
2-(1-methylethyl)-5-(1,1-dimethylpentyl)-4-(1-methyl-1-ethylpropyl)imidazole
2-(1-methylethyl)-4-(1,1-dimethylhexyl)-5-(1-methyl-1-ethylpropyl)imidazole
2-(1-methylethyl)-5-(1,1-dimethylhexyl)-4-(1-methyl-1-ethylpropyl)imidazole
2,4-di(1-methylethyl)-5-(1-methyl-1-ethylpropyl)imidazole
2,5-di(1-methylethyl)-4-(1-methyl-1-ethylpropyl)imidazole
2-(1-methylethyl)-4-(1,2-dimethylpropyl)-5-(1-methyl-1-ethylpropyl)imidazole
2-(1-methylethyl)-5-(1,2-dimethylpropyl)-4-(1-methyl-1-ethylpropyl)imidazole
2-(1,2-dimethylpropyl)-4-tert-butyl-5-(1-methyl-1-ethylpropyl)imidazole
2-(1,2-dimethylpropyl)-5-tert-butyl-4-(1-methyl-1-ethylpropyl)imidazole
2-(1,2-dimethylpropyl)-4-(1,1-dimethylpropyl)-5-(1-methyl-1-ethylpropyl)imidazole
2-(1,2-dimethylpropyl)-5-(1,1-dimethylpropyl)-4-(1-methyl-1-ethylpropyl)imidazole
2-(1,2-dimethylpropyl)-4-(1,1-dimethylbutyl)-5-(1-methyl-1-ethylpropyl)imidazole
2-(1,2-dimethylpropyl)-5-(1,1-dimethylbutyl)-4-(1-methyl-1-ethylpropyl)imidazole
2-(1,2-dimethylpropyl)-4-(1,1-dimethylpentyl)-5-(1-methyl-1-ethylpropyl)imidazole
2-(1,2-dimethylpropyl)-5-(1,1-dimethylpentyl)-4-(1-methyl-1-ethylpropyl)imidazole
2-(1,2-dimethylpropyl)-4-(1,1-dimethylhexyl)-5-(1-methyl-1-ethylpropyl)imidazole
2-(1,2-dimethylpropyl)-5-(1,1-dimethylhexyl)-4-(1-methyl-1-ethylpropyl)imidazole
2-(1,2-dimethylpropyl)-4-(1-methylethyl)-5-(1-methyl-1-ethylpropyl)imidazole 2-(1,2-dimethylpropyl)-5-(1-methylethyl)-4-(1-methyl-1-ethylpropyl)imidazole
2,4-(1,2-dimethylpropyl)-5-(1-methyl-1-ethylpropyl)imidazole
2,5-(1,2-dimethylpropyl)-4-(1-methyl-1-ethylpropyl)imidazole
2-(1-methyl-1-ethylpropyl)-4-tert-butyl-5-(1,1-dimethylpropyl)imidazole
2-(1-methyl-1-ethylpropyl)-5-tert-butyl-4-(1,1-dimethylpropyl)imidazole
2-(1-methyl-1-ethylpropyl)-4-tert-butyl-5-(1,1-dimethylbutyl)imidazole
2-(1-methyl-1-ethylpropyl)-5-tert-butyl-4-(1,1-dimethylbutyl)imidazole
2-(1-methyl-1-ethylpropyl)-4-tert-butyl-5-(1,1-dimethylpentyl)imidazole
2-(1-methyl-1-ethylpropyl)-5-tert-butyl-4-(1,1-dimethylpentyl)imidazole
2-(1-methyl-1-ethylpropyl)-4-tert-butyl-5-(1,1-dimethylhexyl)imidazole
2-(1-methyl-1-ethylpropyl)-5-tert-butyl-4-(1,1-dimethylhexyl)imidazole
2-(1-methyl-1-ethylpropyl)-4-(1,1-dimethylpropyl)-5-(dimethylbutyl)imidazole 2-(1-methyl-1-ethylpropyl)-4-(1,1-dimethylpropyl)-5-(dimethylbutyl)imidazole 2-(1-methyl-1-ethylpropyl)-4-(1,1-dimethylpropyl)-5-(dimethylpentyl)imidazole 2-(1-methyl-1-ethylpropyl)-4-(1,1-dimethylpropyl)-5-(dimethylpentyl)imidazole 2-(1-methyl-1-ethylpropyl)-4-(1,1-dimethylpropyl)-5-(dimethylhexyl)imidazole 2-(1-methyl-1-ethylpropyl)-4-(1,1-dimethylpropyl)-5-(dimethylhexyl)imidazole 2-(1-methyl-1-ethylpropyl)-4-(dimethylpentyl)-5-(1,1-dimethylbutyl)imidazole
2-(1-methyl-1-ethylpropyl)-5-(dimethylpentyl)-4-(1,1-dimethylbutyl)imidazole
2-(1-methyl-1-ethylpropyl)-4-(dimethylpentyl)-5-(1,1-dimethylhexyl)imidazole
2-(1-methyl-1-ethylpropyl)-5-(dimethylpentyl)-4-(1,1-dimethylhexyl)imidazole
2-(1-methyl-1-ethylpropyl)-4-tert-butyl-5-(1-methylethyl)imidazole
2-(1-methyl-1-ethylpropyl)-5-tert-butyl-4-(1-methylethyl)imidazole
2-(1-methyl-1-ethylpropyl)-4-(1,1-dimethylpropyl)-5-(1-methylethyl)imidazole
2-(1-methyl-1-ethylpropyl)-5-(1,1-dimethylpropyl)-4-(1-methylethyl)imidazole
2-(1-methyl-1-ethylpropyl)-4-(1,1-dimethylbutyl)-5-(1-methylethyl)imidazole
2-(1-methyl-1-ethylpropyl)-5-(1,1-dimethylbutyl)-4-(1-methylethyl)imidazole
2-(1-methyl-1-ethylpropyl)-4-(1,1-dimethylpentyl)-5-(1-methylethyl)imidazole
2-(1-methyl-1-ethylpropyl)-5-(1,1-dimethylpentyl)-4-(1-methylethyl)imidazole
2-(1-methyl-1-ethylpropyl)-4-(1,1-dimethylhexyl)-5-(1-methylethyl)imidazole
2-(1-methyl-1-ethylpropyl)-5-(1,1-dimethylhexyl)-4-(1-methylethyl)imidazole
2-(1-methyl-1-ethylpropyl)-4-tert-butyl-5-(1,2-dimethylpropyl)imidazole
2-(1-methyl-1-ethylpropyl)-5-tert-butyl-4-(1,2-dimethylpropyl)imidazole
2-(1-methyl-1-ethylpropyl)-4-tert-butyl-5-(1,2-dimethylpropyl)imidazole
2-(1-methyl-1-ethylpropyl)-4-(1,1-dimethylpropyl)-5-(1,2-dimethylpropyl)imidazole
2-(1-methyl-1-ethylpropyl)-5-(1,1-dimethylpropyl)-4-(1,2-dimethylpropyl)imidazole
2-(1-methyl-1-ethylpropyl)-4-(1,1-dimethylbutyl)-5-(1,2-dimethylpropyl)imidazole
2-(1-methyl-1-ethylpropyl)-5-(1,1-dimethylbutyl)-4-(1,2-dimethylpropyl)imidazole
2-(1-methyl-1-ethylpropyl)-4-(1,1-dimethylpentyl)-5-(1,2-dimethylpropyl)imidazole
2-(1-methyl-1-ethylpropyl)-5-(1,1-dimethylpentyl)-4-(1,2-dimethylpropyl)imidazole
2-(1-methyl-1-ethylpropyl)-4-(1,1-dimethylhexyl)-5-(1,2-dimethylpropyl)imidazole
2-(1-methyl-1-ethylpropyl)-5-(1,1-dimethylhexyl)-4-(1,2-dimethylpropyl)imidazole
2-(1-methyl-1-ethylpropyl)-4-(1-methylethyl)-5-(1,2-dimethylpropyl)imidazole
2-(1-methyl-1-ethylpropyl)-5-(1-methylethyl)-4-(1,2-dimethylpropyl)imidazole
2,4-di(1-methyl-1-ethylpropyl)-5-tert-butylimidazole
2,5-di(1-methyl-1-ethylpropyl)-4-tert-butylimidazole
2,4-di(1-methyl-1-ethylpropyl)-5-(1,1-dimethylpropyl)imidazole
2,5-di(1-methyl-1-ethylpropyl)-4-(1,1-dimethylpropyl)imidazole
2,4-di(1-methyl-1-ethylpropyl)-5-(1,1-dimethylbutyl)imidazole
2,5-di(1-methyl-1-ethylpropyl)-4-(1,1-dimethylbutyl)imidazole
2,4-di(1-methyl-1-ethylpropyl)-5-(1,1-dimethylpentyl)imidazole
2,5-di(1-methyl-1-ethylpropyl)-4-(1,1-dimethylpentyl)imidazole
2,4-di(1-methyl-1-ethylpropyl)-5-(1,1-dimethylhexyl)imidazole
2,5-di(1-methyl-1-ethylpropyl)-4-(1,1-dimethylhexyl)imidazole
2,4-di(1-methyl-1-ethylpropyl)-5-(1-methylethyl)imidazole
2,5-di(1-methyl-1-ethylpropyl)-4-(1-methylethyl)imidazole
2,4-di(1-methyl-1-ethylpropyl)-5-(1,2-dimethylpropyl)imidazole
2,5-di(1-methyl-1-ethylpropyl)-4-(1,2-dimethylpropyl)imidazole
2-tertbutyl-4,5-di(1-methylpropyl)imidazole
2-(1,1-dimethylpropyl)-4,5-di(1-methylpropyl)imidazole
2-(1,1-dimethylbutyl)-4,5-di(1-methylpropyl)imidazole
2-(1,1-dimethylpentyl)-4,5-di(1-methylpropyl)imidazole
2-(1,1-dimethylhexyl)-4,5-di(1-methylpropyl)imidazole
2-(1,1-dimethylhexyl)-4,5-di(1-methylpropyl)imidazole
2-(1-methylethyl)-4,5-di(1-methylpropyl)imidazole
2,4,5-tri(1-methylpropyl)imidazole
2,4-di-ter-butyl-5-(1-methylpropyl)imidazole
2,5-di-ter-butyl-4-(1-methylpropyl)imidazole
2-tert-butyl-4-(1,1-dimethylpropyl)-5-(1-methylpropyl)imidazole
2-tert-butyl-5-(1,1-dimethylpropyl)-4-(1-methylpropyl)imidazole
2-tert-butyl-4-(1,1-dimethylbutyl)-5-(1-methylpropyl)imidazole
2-tert-butyl-5-(1,1-dimethylbutyl)-4-(1-methylpropyl)imidazole
2-tert-butyl-4-(1,1-dimethylpentyl)-5-(1-methylpropyl)imidazole
2-tert-butyl-5-(1,1-dimethylpentyl)-4-(1-methylpropyl)imidazole
2-tert-butyl-4-(1,1-dimethylhexyl)-5-(1-methylpropyl)imidazole 2-tert-butyl-5-(1,1-dimethylhexyl)-4-(1-methylpropyl)imidazole
2-tert-butyl-4-(1-methylpropyl)-5-(1-methylpropyl)imidazole
2-tert-butyl-5-(1-methylpropyl)-4-(1-methylpropyl)imidazole
2-tert-butyl-4-(1,2-dimethylpropyl)-5-(1-methylpropyl)imidazole
2-tert-butyl-5-(1,2-dimethylpropyl)-4-(1-methylpropyl)imidazole
2-(1,1-dimethylpropyl)-4-tert-butyl-5-(1-methylpropyl)imidazole
2-(1,1-dimethylpropyl)-5-tert-butyl-4-(1-methylpropyl)imidazole
2,4-(1,1-dimethylpropyl)-5-(1-methylpropyl)imidazole
2-(1,1-dimethylpropyl)-4-(1,1-dimethyl butyl)-5-(1-methylpropyl)imidazole
2-(1,1-dimethylpropyl)-5-(1,1-dimethyl butyl)-4-(1-methylpropyl)imidazole
2-(1,1-dimethylpropyl)-4-(1,1-dimethyl pentyl)-5-(1-methylpropyl)imidazole
2-(1,1-dimethylpropyl)-5-(1,1-dimethylpentyl)-4-(1-methylpropyl)imidazole
2-(1,1-dimethylpropyl)-4-(1,1-dimethylhexyl)-5-(1-methylpropyl)imidazole
2-(1,1-dimethylpropyl)-5-(1,1-dimethylhexyl)-4-(1-methylpropyl)imidazole
2-(1,1-dimethylpropyl)-4-(1-methylethyl)-5-(1-methylpropyl)imidazole
2-(1,1-dimethylpropyl)-5-(1-methylethyl)-4-(1-methylpropyl)imidazole
2-(1,1-dimethylpropyl)-4-(1,2-dimethylpropyl)-5-(1-methylpropyl)imidazole
2-(1,1-dimethylpropyl)-5-(1,1-dimethylpropyl)-4-(1-methylpropyl)imidazole
2-(1,1-dimethylbutyl)-4-tert-butyl-5-(1-methylpropyl)imidazole
2-(1,1-dimethylbutyl)-5-tert-butyl-4-(1-methylpropyl)imidazole
2-(1,1-dimethylbutyl)-4-(1,1-dimethylpropyl)-5-(1-methylpropyl)imidazole
2-(1,1-dimethylbutyl)-5-(1,1-dimethylpropyl)-4-(1-methylpropyl)imidazole
2,4-di(1,1-dimethylbutyl)-5-(1-methylpropyl)imidazole
2,5-di(1,1-dimethylbutyl)-4-(1-methylpropyl)imidazole
2-(1,1-dimethylbutyl)-4-(1,1-dimethylpentyl)-5-(1-methylpropyl)imidazole
2-(1,1-dimethylbutyl)-5-(1,1-dimethylpentyl)-4-(1-methylpropyl)imidazole
2-(1,1-dimethylbutyl)-4-(1,1-dimethylhexyl)-5-(1-methylpropyl)imidazole
2-(1,1-dimethylbutyl)-5-(1,1-dimethylhexyl)-4-(1-methylpropyl)imidazole
2-(1,1-dimethylbutyl)-4-(1-methylethyl)-5-(1-methylpropyl)imidazole
2-(1,1-dimethylbutyl)-5-(1-methylethyl)-4-(1-methylpropyl)imidazole
2-(1,1-dimethylbutyl)-4-(1,2-dimethylpropyl)-5-(1-methylpropyl)imidazole
2-(1,1-dimethylbutyl)-5-(1,2-dimethylpropyl)-4-(1-methylpropyl)imidazole
2-(1,1-dimethylpentyl)-4-tert-butyl-5-(1-methylpropyl)imidazole
2-(1,1-dimethylpentyl)-5-tert-butyl-4-(1-methylpropyl)imidazole
2-(1,1-dimethylpentyl)-4-(1,1-dimethylpropyl)-5-(1-methylpropyl)imidazole
2-(1,1-dimethylpentyl)-5-(1,1-dimethylpropyl)-4-(1-methylpropyl)imidazole
2-(1,1-dimethylpentyl)-4-(1,1-dimethylbutyl)-5-(1-methylpropyl)imidazole
2-(1,1-dimethylpentyl)-5-(1,1-dimethylbutyl)-4-(1-methylpropyl)imidazole
2-4-di(1,1-dimethylpentyl)-5-(1-methylpropyl)imidazole
2-5-di(1,1-dimethylpentyl)-4-(1-methylpropyl)imidazole
2-(1,1-dimethylpentyl)-4-(1,1-dimethylhexyl)-5-(1-methylpropyl)imidazole
2-(1,1-dimethylpentyl)-5-(1,1-dimethylhexyl)-4-(1-methylpropyl)imidazole
2-(1,1-dimethylpentyl)-4-(1-methylethyl)-5-(1-methylpropyl)imidazole
2-(1,1-dimethylpentyl)-5-(1-methylethyl)-4-(1-methylpropyl)imidazole
2-(1,1-dimethylpentyl)-4-(1,2-dimethylpropyl)-5-(1-methylpropyl)imidazole
2-(1,1-dimethylpentyl)-5-(1,2-dimethylpropyl)-4-(1-methylpropyl)imidazole
2-(1,1-dimethylhexyl)-4-tert-butyl-5-(1-methylpropyl)imidazole
2-(1,1-dimethylhexyl)-5-tert-butyl-4-(1-methylpropyl)imidazole
2-(1,1-dimethylhexyl)-4-(1,1-dimethylpropyl)-5-(1-methylpropyl)imidazole
2-(1,1-dimethylhexyl)-5-(1,1-dimethylpropyl)-4-(1-methylpropyl)imidazole
2-(1,1-dimethylhexyl)-4-(1,1-dimethylbutyl)-5-(1-methylpropyl)imidazole
2-(1,1-dimethylhexyl)-5-(1,1-dimethylbutyl)-4-(1-methylpropyl)imidazole
2-(1,1-dimethylhexyl)-4-(1,1-dimethylpentyl)-5-(1-methylpropyl)imidazole
2-(1,1-dimethylhexyl)-5-(1,1-dimethylpentyl)-4-(1-methylpropyl)imidazole
2,4-(1,1-dimethylhexyl)-5-(1-methylpropyl)imidazole
2,5-(1,1-dimethylhexyl)-4-(1-methylpropyl)imidazole
2-(1,1-dimethylhexyl)-4-(1-methylethyl)-5-(1-methylpropyl)imidazole
2-(1,1-dimethylhexyl)-5-(1-methylethyl)-4-(1-methylpropyl)imidazole
2-(1,1-dimethylhexyl)-4-(1,2-dimethylpropyl)-5-(1-methylpropyl)imidazole
2-(1,1-dimethylhexyl)-5-(1,2-dimethylpropyl)-4-(1-methylpropyl)imidazole
2-(1-methylethyl)-4-tert-butyl-5-(1-methylpropyl)imidazole
2-(1-methylethyl)-5-tert-butyl-4-(1-methylpropyl)imidazole
2-(1-methylethyl)-4-(1,1-dimethylpropyl)-5-(1-methylpropyl)imidazole
2-(1-methylethyl)-5-(1,1-dimethylpropyl)-4-(1-methylpropyl)imidazole
2-(1-methylethyl)-4-(1,1-dimethylbutyl)-5-(1-methylpropyl)imidazole
2-(1-methylethyl)-5-(1,1-dimethylbutyl)-4-(1-methylpropyl)imidazole
2-(1-methylethyl)-4-(1,1-dimethylpentyl)-5-(1-methylpropyl)imidazole
2-(1-methylethyl)-5-(1,1-dimethylpentyl)-4-(1-methylpropyl)imidazole
2-(1-methylethyl)-4-(1,1-dimethylhexyl)-5-(1-methylpropyl)imidazole
2-(1-methylethyl)-5-(1,1-dimethylhexyl)-4-(1-methylpropyl)imidazole
2,4-di(1-methylethyl)-5-(1-methylpropyl)imidazole
2,5-di(1-methylethyl)-4-(1-methylpropyl)imidazole 2-(1-methylethyl)-4-(1,2-dimethylpropyl)-5-(1-methylpropyl)imidazole
2-(1-methylethyl)-5-(1,2-dimethylpropyl)-4-(1-methylpropyl)imidazole
2-(1,2-dimethylpropyl)-4-tert-butyl-5-(1-methylpropyl)imidazole
2-(1,2-dimethylpropyl)-5-tert-butyl-4-(1-methylpropyl)imidazole
2-(1,2-dimethylpropyl)-4-(1,1-dimethylpropyl)-5-(1-methylpropyl)imidazole
2-(1,2-dimethylpropyl)-5-(1,1-dimethylpropyl)-4-(1-methylpropyl)imidazole
2-(1,2-dimethylpropyl)-4-(1,1-dimethylbutyl)-5-(1-methylpropyl)imidazole
2-(1,2-dimethylpropyl)-5-(1,1-dimethylbutyl)-4-(1-methylpropyl)imidazole
2-(1,2-dimethylpropyl)-4-(1,1-dimethylpentyl)-5-(1-methylpropyl)imidazole
2-(1,2-dimethylpropyl)-5-(1,1-dimethylpentyl)-4-(1-methylpropyl)imidazole
2-(1,2-dimethylpropyl)-4-(1,1-dimethylhexyl)-5-(1-methylpropyl)imidazole
2-(1,2-dimethylpropyl)-5-(1,1-dimethylhexyl)-4-(1-methylpropyl)imidazole
2-(1,2-dimethylpropyl)-4-(1-methylethyl)-5-(1-methylpropyl)imidazole
2-(1,2-dimethylpropyl)-5-(1-methylethyl)-4-(1-methylpropyl)imidazole
2,4-(1,2-dimethylpropyl)-5-(1-methylpropyl)imidazole
2,5-(1,2-dimethylpropyl)-4-(1-methylpropyl)imidazole
2-(1-methylpropyl)-4-tert-butyl-5-(1,1-dimethylpropyl)imidazole
2-(1-methylpropyl)-5-tert-butyl-4-(1,1-dimethylpropyl)imidazole
2-(1-methylpropyl)-4-tert-butyl-5-(1,1-dimethylbutyl)imidazole
2-(1-methylpropyl)-5-tert-butyl-4-(1,1-dimethylbutyl)imidazole
2-(1-methylpropyl)-4-tert-butyl-5-(1,1-dimethylpentyl)imidazole
2-(1-methylpropyl)-5-tert-butyl-4-(1,1-dimethylpentyl)imidazole
2-(1-methylpropyl)-4-tert-butyl-5-(1,1-dimethylhexyl)imidazole
2-(1-methylpropyl)-5-tert-butyl-4-(1,1-dimethylhexyl)imidazole
2-(1-methylpropyl)-4-(1,1-dimethylpropyl)-5-(dimethylbutyl)imidazole 2-(1-methylpropyl)-4-(1,1-dimethylpropyl)-5-(dimethylbutyl)imidazole 2-(1-methylpropyl)-4-(1,1-dimethylpropyl)-5-(dimethylpentyl)imidazole 2-(1-methylpropyl)-4-(1,1-dimethylpropyl)-5-(dimethylpentyl)imidazole 2-(1-methylpropyl)-4-(1,1-dimethylpropyl)-5-(dimethylhexyl)imidazole
2-(1-methylpropyl)-4-(1,1-dimethylpropyl)-5-(dimethylhexyl)imidazole 2-(1-methylpropyl)-4-(dimethylpentyl)-5-(1,1-dimethylbutyl)imidazole
2-(1-methylpropyl)-5-(dimethylpentyl)-4-(1,1-dimethylbutyl)imidazole
2-(1-methylpropyl)-4-(dimethylpentyl)-5-(1,1-dimethylhexyl)imidazole
2-(1-methylpropyl)-5-(dimethylpentyl)-4-(1,1-dimethylhexyl)imidazole
2-(1-methylpropyl)-4-tert-butyl-5-(1-methylethyl)imidazole
2-(1-methylpropyl)-5-tert-butyl-4-(1-methylethyl)imidazole
2-(1-methylpropyl)-4-(1,1-dimethylpropyl)-5-(1-methylethyl)imidazole
2-(1-methylpropyl)-5-(1,1-dimethylpropyl)-4-(1-methylethyl)imidazole
2-(1-methylpropyl)-4-(1,1-dimethylbutyl)-5-(1-methylethyl)imidazole
2-(1-methylpropyl)-5-(1,1-dimethylbutyl)-4-(1-methylethyl)imidazole
2-(1-methylpropyl)-4-(1,1-dimethylpentyl)-5-(1-methylethyl)imidazole
2-(1-methylpropyl)-5-(1,1-dimethylpentyl)-4-(1-methylethyl)imidazole
2-(1-methylpropyl)-4-(1,1-dimethylhexyl)-5-(1-methylethyl)imidazole
2-(1-methylpropyl)-5-(1,1-dimethylhexyl)-4-(1-methylethyl)imidazole
2-(1-methylpropyl)-4-tert-butyl-5-(1,2-dimethylpropyl)imidazole
2-(1-methylpropyl)-5-tert-butyl-4-(1,2-dimethylpropyl)imidazole
2-(1-methylpropyl)-4-tert-butyl-5-(1,2-dimethylpropyl)imidazole
2-(1-methylpropyl)-4-(1,1-dimethylpropyl)-5-(1,2-dimethylpropyl)imidazole
2-(1-methylpropyl)-5-(1,1-dimethylpropyl)-4-(1,2-dimethylpropyl)imidazole
2-(1-methylpropyl)-4-(1,1-dimethylbutyl)-5-(1,2-dimethylpropyl)imidazole
2-(1-methylpropyl)-5-(1,1-dimethylbutyl)-4-(1,2-dimethylpropyl)imidazole
2-(1-methylpropyl)-4-(1,1-dimethylpentyl)-5-(1,2-dimethylpropyl)imidazole
2-(1-methylpropyl)-5-(1,1-dimethylpentyl)-4-(1,2-dimethylpropyl)imidazole
2-(1-methylpropyl)-4-(1,1-dimethylhexyl)-5-(1,2-dimethylpropyl)imidazole
2-(1-methylpropyl)-5-(1,1-dimethylhexyl)-4-(1,2-dimethylpropyl)imidazole
2-(1-methylpropyl)-4-(1-methylethyl)-5-(1,2-dimethylpropyl)imidazole
2-(1-methylpropyl)-5-(1-methylethyl)-4-(1,2-dimethylpropyl)imidazole
2,4-di(1-methylpropyl)-5-tert-butylimidazole
2,5-di(1-methylpropyl)-4-tert-butylimidazole
2,4-di(1-methylpropyl)-5-(1,1-dimethylpropyl)imidazole
2,5-di(1-methylpropyl)-4-(1,1-dimethylpropyl)imidazole
2,4-di(1-methylpropyl)-5-(1,1-dimethylbutyl)imidazole
2,5-di(1-methylpropyl)-4-(1,1-dimethylbutyl)imidazole
2,4-di(1-methylpropyl)-5-(1,1-dimethylpentyl)imidazole
2,5-di(1-methylpropyl)-4-(1,1-dimethylpentyl)imidazole
2,4-di(1-methylpropyl)-5-(1,1-dimethylhexyl)imidazole
2,5-di(1-methylpropyl)-4-(1,1-dimethylhexyl)imidazole
2,4-di(1-methylpropyl)-5-(1-methylethyl)imidazole
2,5-di(1-methylpropyl)-4-(1-methylethyl)imidazole
2,4-di(1-methylpropyl)-5-(1,2-dimethylpropyl)imidazole
2,5-di(1-methylpropyl)-4-(1,2-dimethylpropyl)imidazole
2-tertbutyl-4,5-di(1-methylbutyl)imidazole
2-(1,1-dimethylpropyl)-4,5-di(1-methylbutyl)imidazole
2-(1,1-dimethylbutyl)-4,5-di(1-methylbutyl)imidazole
2-(1,1-dimethylpentyl)-4,5-di(1-methylbutyl)imidazole
2-(1,1-dimethylhexyl)-4,5-di(1-methylbutyl)imidazole
2-(1,1-dimethylhexyl)-4,5-di(1-methylbutyl)imidazole
2-(1-methylethyl)-4,5-di(1-methylbutyl)imidazole
2,4,5-tri(1-methylbutyl)imidazole
2,4-di-ter-butyl-5-(1-methylbutyl)imidazole
2,5-di-ter-butyl-4-(1-methylbutyl)imidazole
2-tert-butyl-4-(1,1-dimethylpropyl)-5-(1-methylbutyl)imidazole 2-tert-butyl-5-(1,1-dimethylpropyl)-4-(1-methylbutyl)imidazole
2-tert-butyl-4-(1,1-dimethylbutyl)-5-(1-methylbutyl)imidazole
2-tert-butyl-5-(1,1-dimethylbutyl)-4-(1-methylbutyl)imidazole
2-tert-butyl-4-(1,1-dimethylpentyl)-5-(1-methylbutyl)imidazole
2-tert-butyl-5-(1,1-dimethylpentyl)-4-(1-methylbutyl)imidazole
2-tert-butyl-4-(1,1-dimethylhexyl)-5-(1-methylbutyl)imidazole
2-tert-butyl-5-(1,1-dimethylhexyl)-4-(1-methylbutyl)imidazole
2-tert-butyl-4-(1-methylbutyl)-5-(1-methylbutyl)imidazole
2-tert-butyl-5-(1-methylbutyl)-4-(1-methylbutyl)imidazole
2-tert-butyl-4-(1,2-dimethylpropyl)-5-(1-methylbutyl)imidazole
2-tert-butyl-5-(1,2-dimethylpropyl)-4-(1-methylbutyl)imidazole
2-(1,1-dimethylpropyl)-4-tert-butyl-5-(1-methylbutyl)imidazole
2-(1,1-dimethylpropyl)-5-tert-butyl-4-(1-methylbutyl)imidazole
2,4-(1,1-dimethylpropyl)-5-(1-methylbutyl)imidazole
2-(1,1-dimethylpropyl)-4-(1,1-dimethylbutyl)-5-(1-methylbutyl)imidazole
2-(1,1-dimethylpropyl)-5-(1,1-dimethylbutyl)-4-(1-methylbutyl)imidazole
2-(1,1-dimethylpropyl)-4-(1,1-dimethylpentyl)-5-(1-methylbutyl)imidazole
2-(1,1-dimethylpropyl)-5-(1,1-dimethylpentyl)-4-(1-methylbutyl)imidazole
2-(1,1-dimethylpropyl)-4-(1,1-dimethylhexyl)-5-(1-methylbutyl)imidazole
2-(1,1-dimethylpropyl)-5-(1,1-dimethylhexyl)-4-(1-methylbutyl)imidazole
2-(1,1-dimethylpropyl)-4-(1-methylethyl)-5-(1-methylbutyl)imidazole
2-(1,1-dimethylpropyl)-5-(1-methylethyl)-4-(1-methylbutyl)imidazole
2-(1,1-dimethylpropyl)-4-(1,2-dimethylpropyl)-5-(1-methylbutyl)imidazole
2-(1,1-dimethylpropyl)-5-(1,2-dimethylpropyl)-4-(1-methylbutyl)imidazole
2-(1,1-dimethylbutyl)-4-tert-butyl-5-(1-methylbutyl)imidazole
2-(1,1-dimethylbutyl)-5-tert-butyl-4-(1-methylbutyl)imidazole
2-(1,1-dimethylbutyl)-4-(1,1-dimethylpropyl)-5-(1-methylbutyl)imidazole
2-(1,1-dimethylbutyl)-5-(1,1-dimethylpropyl)-4-(1-methylbutyl)imidazole
2,4-di(1,1-dimethylbutyl)-5-(1-methylbutyl)imidazole
2,5-di(1,1-dimethylbutyl)-4-(1-methylbutyl)imidazole
2-(1,1-dimethyl butyl)-4-(1,1-dimethylpentyl)-5-(1-methylbutyl)imidazole
2-(1,1-dimethyl butyl)-5-(1,1-dimethylpentyl)-4-(1-methylbutyl)imidazole
2-(1,1-dimethylbutyl)-4-(1,1-dimethylhexyl)-5-(1-methylbutyl)imidazole
2-(1,1-dimethylbutyl)-5-(1,1-dimethylhexyl)-4-(1-methylbutyl)imidazole
2-(1,1-dimethylbutyl)-4-(1-methylethyl)-5-(1-methylbutyl)imidazole
2-(1,1-dimethylbutyl)-5-(1-methylethyl)-4-(1-methylbutyl)imidazole
2-(1,1-dimethylbutyl)-4-(1,2-dimethylpropyl)-5-(1-methylbutyl)imidazole
2-(1,1-dimethylbutyl)-5-(1,2-dimethylpropyl)-4-(1-methylbutyl)imidazole
2-(1,1-dimethylpentyl)-4-tert-butyl-5-(1-methylbutyl)imidazole
2-(1,1-dimethylpentyl)-5-tert-butyl-4-(1-methylbutyl)imidazole
2-(1,1-dimethylpentyl)-4-(1,1-dimethylpropyl)-5-(1-methylbutyl)imidazole
2-(1,1-dimethylpentyl)-5-(1,1-dimethylpropyl)-4-(1-methylbutyl)imidazole
2-(1,1-dimethylpentyl)-4-(1,1-dimethylbutyl)-5-(1-methylbutyl)imidazole
2-(1,1-dimethylpentyl)-5-(1,1-dimethylbutyl)-4-(1-methylbutyl)imidazole
2-4-di(1,1-dimethylpentyl)-5-(1-methylbutyl)imidazole
2-5-di(1,1-dimethylpentyl)-4-(1-methylbutyl)imidazole
2-(1,1-dimethylpentyl)-4-(1,1-dimethylhexyl)-5-(1-methylbutyl)imidazole
2-(1,1-dimethylpentyl)-5-(1,1-dimethylhexyl)-4-(1-methylbutyl)imidazole
2-(1,1-dimethylpentyl)-4-(1-methylethyl)-5-(1-methylbutyl)imidazole
2-(1,1-dimethylpentyl)-5-(1-methylethyl)-4-(1-methylbutyl)imidazole
2-(1,1-dimethylpentyl)-4-(1,2-dimethylpropyl)-5-(1-methylbutyl)imidazole
2-(1,1-dimethylpentyl)-5-(1,2-dimethylpropyl)-4-(1-methylbutyl)imidazole
2-(1,1-dimethylhexyl)-4-tert-butyl-5-(1-methylbutyl)imidazole
2-(1,1-dimethylhexyl)-5-tert-butyl-4-(1-methylbutyl)imidazole
2-(1,1-dimethylhexyl)-4-(1,1-dimethylpropyl)-5-(1-methylbutyl)imidazole
2-(1,1-dimethylhexyl)-5-(1,1-dimethylpropyl)-4-(1-methylbutyl)imidazole
2-(1,1-dimethylhexyl)-4-(1,1-dimethylbutyl)-5-(1-methylbutyl)imidazole
2-(1,1-dimethylhexyl)-5-(1,1-dimethylbutyl)-4-(1-methylbutyl)imidazole
2-(1,1-dimethylhexyl)-4-(1,1-dimethylpentyl)-5-(1-methylbutyl)imidazole
2-(1,1-dimethylhexyl)-5-(1,1-dimethylpentyl)-4-(1-methylbutyl)imidazole
2,4-(1,1-dimethylhexyl)-5-(1-methylbutyl)imidazole
2,5-(1,1-dimethylhexyl)-4-(1-methylbutyl)imidazole
2-(1,1-dimethylhexyl)-4-(1-methylethyl)-5-(1-methylbutyl)imidazole
2-(1,1-dimethylhexyl)-5-(1-methylethyl)-4-(1-methylbutyl)imidazole
2-(1,1-dimethylhexyl)-4-(1,2-dimethylpropyl)-5-(1-methylbutyl)imidazole
2-(1,1-dimethylhexyl)-5-(1,2-dimethylpropyl)-4-(1-methylbutyl)imidazole
2-(1-methylethyl)-4-tert-butyl-5-(1-methylbutyl)imidazole
2-(1-methylethyl)-5-tert-butyl-4-(1-methylbutyl)imidazole
2-(1-methylethyl)-4-(1,1-dimethylpropyl)-5-(1-methylbutyl)imidazole
2-(1-methylethyl)-5-(1,1-dimethylpropyl)-4-(1-methylbutyl)imidazole
2-(1-methylethyl)-4-(1,1-dimethylbutyl)-5-(1-methylbutyl)imidazole
2-(1-methylethyl)-5-(1,1-dimethylbutyl)-4-(1-methylbutyl)imidazole 2-(1-methylethyl)-4-(1,1-dimethylpentyl)-5-(1-methylbutyl)imidazole
2-(1-methylethyl)-5-(1,1-dimethylpentyl)-4-(1-methylbutyl)imidazole
2-(1-methylethyl)-4-(1,1-dimethylhexyl)-5-(1-methylbutyl)imidazole
2-(1-methylethyl)-5-(1,1-dimethylhexyl)-4-(1-methylbutyl)imidazole
2,4-di(1-methylethyl)-5-(1-methylbutyl)imidazole
2,5-di(1-methylethyl)-4-(1-methylbutyl)imidazole
2-(1-methylethyl)-4-(1,2-dimethylpropyl)-5-(1-methylbutyl)imidazole
2-(1-methylethyl)-5-(1,2-dimethylpropyl)-4-(1-methylbutyl)imidazole
2-(1,2-dimethylpropyl)-4-tert-butyl-5-(1-methylbutyl)imidazole
2-(1,2-dimethylpropyl)-5-tert-butyl-4-(1-methylbutyl)imidazole
2-(1,2-dimethylpropyl)-4-(1,1-dimethylpropyl)-5-(1-methylbutyl)imidazole
2-(1,2-dimethylpropyl)-5-(1,1-dimethylpropyl)-4-(1-methylbutyl)imidazole
2-(1,2-dimethylpropyl)-4-(1,1-dimethylbutyl)-5-(1-methylbutyl)imidazole
2-(1,2-dimethylpropyl)-5-(1,1-dimethylbutyl)-4-(1-methylbutyl)imidazole
2-(1,2-dimethylpropyl)-4-(1,1-dimethylpentyl)-5-(1-methylbutyl)imidazole
2-(1,2-dimethylpropyl)-5-(1,1-dimethylpentyl)-4-(1-methylbutyl)imidazole
2-(1,2-dimethylpropyl)-4-(1,1-dimethylhexyl)-5-(1-methylbutyl)imidazole
2-(1,2-dimethylpropyl)-5-(1,1-dimethylhexyl)-4-(1-methylbutyl)imidazole
2-(1,2-dimethylpropyl)-4-(1-methylethyl)-5-(1-methylbutyl)imidazole
2-(1,2-dimethylpropyl)-5-(1-methylethyl)-4-(1-methylbutyl)imidazole
2,4-(1,2-dimethylpropyl)-5-(1-methylbutyl)imidazole
2,5-(1,2-dimethylpropyl)-4-(1-methylbutyl)imidazole
2-(1-methylbutyl)-4-tert-butyl-5-(1,1-dimethylpropyl)imidazole
2-(1-methylbutyl)-5-tert-butyl-4-(1,1-dimethylpropyl)imidazole
2-(1-methylbutyl)-4-tert-butyl-5-(1,1-dimethylbutyl)imidazole
2-(1-methylbutyl)-5-tert-butyl-4-(1,1-dimethylbutyl)imidazole
2-(1-methylbutyl)-4-tert-butyl-5-(1,1-dimethylpentyl)imidazole
2-(1-methylbutyl)-5-tert-butyl-4-(1,1-dimethylpentyl)imidazole
2-(1-methylbutyl)-4-tert-butyl-5-(1,1-dimethylhexyl)imidazole
2-(1-methylbutyl)-5-tert-butyl-4-(1,1-dimethylhexyl)imidazole
2-(1-methylbutyl)-4-(1,1-dimethylpropyl)-5-(dimethylbutyl)imidazole
2-(1-methylbutyl)-4-(1,1-dimethylpropyl)-5-(dimethylbutyl)imidazole
2-(1-methylbutyl)-4-(1,1-dimethylpropyl)-5-(dimethylpentyl)imidazole
2-(1-methylbutyl)-4-(1,1-dimethylpropyl)-5-(dimethylpentyl)imidazole
2-(1-methylbutyl)-4-(1,1-dimethylpropyl)-5-(dimethylhexyl)imidazole
2-(1-methylbutyl)-4-(1,1-dimethylpropyl)-5-(dimethylhexyl)imidazole
2-(1-methylbutyl)-4-(dimethylpentyl)-5-(1,1-dimethylbutyl)imidazole
2-(1-methylbutyl)-5-(dimethylpentyl)-4-(1,1-dimethylbutyl)imidazole
2-(1-methylbutyl)-4-(dimethylpentyl)-5-(1,1-dimethylhexyl)imidazole
2-(1-methylbutyl)-5-(dimethylpentyl)-4-(1,1-dimethylhexyl)imidazole
2-(1-methylbutyl)-4-tert-butyl-5-(1-methylethyl)imidazole
2-(1-methylbutyl)-5-tert-butyl-4-(1-methylethyl)imidazole
2-(1-methylbutyl)-4-(1,1-dimethylpropyl)-5-(1-methylethyl)imidazole
2-(1-methylbutyl)-5-(1,1-dimethylpropyl)-4-(1-methylethyl)imidazole
2-(1-methylbutyl)-4-(1,1-dimethylbutyl)-5-(1-methylethyl)imidazole
2-(1-methylbutyl)-5-(1,1-dimethylbutyl)-4-(1-methylethyl)imidazole
2-(1-methylbutyl)-4-(1,1-dimethylpentyl)-5-(1-methylethyl)imidazole
2-(1-methylbutyl)-5-(1,1-dimethylpentyl)-4-(1-methylethyl)imidazole
2-(1-methylbutyl)-4-(1,1-dimethylhexyl)-5-(1-methylethyl)imidazole
2-(1-methylbutyl)-5-(1,1-dimethylhexyl)-4-(1-methylethyl)imidazole
2-(1-methylbutyl)-4-tert-butyl-5-(1,2-dimethylpropyl)imidazole
2-(1-methylbutyl)-5-tert-butyl-4-(1,2-dimethylpropyl)imidazole
2-(1-methylbutyl)-4-tert-butyl-5-(1,2-dimethylpropyl)imidazole
2-(1-methylbutyl)-4-(1,1-dimethylpropyl)-5-(1,2-dimethylpropyl)imidazole
2-(1-methylbutyl)-5-(1,1-dimethylpropyl)-4-(1,2-dimethylpropyl)imidazole
2-(1-methylbutyl)-4-(1,1-dimethylbutyl)-5-(1,2-dimethylpropyl)imidazole
2-(1-methylbutyl)-5-(1,1-dimethylbutyl)-4-(1,2-dimethylpropyl)imidazole
2-(1-methylbutyl)-4-(1,1-dimethylpentyl)-5-(1,2-dimethylpropyl)imidazole
2-(1-methylbutyl)-5-(1,1-dimethylpentyl)-4-(1,2-dimethylpropyl)imidazole
2-(1-methylbutyl)-4-(1,1-dimethylhexyl)-5-(1,2-dimethylpropyl)imidazole
2-(1-methylbutyl)-5-(1,1-dimethylhexyl)-4-(1,2-dimethylpropyl)imidazole
2-(1-methylbutyl)-4-(1-methylethyl)-5-(1,2-dimethylpropyl)imidazole
2-(1-methylbutyl)-5-(1-methylethyl)-4-(1,2-dimethylpropyl)imidazole
2,4-di(1-methylbutyl)-5-tert-butylimidazole
2,5-di(1-methylbutyl)-4-tert-butylimidazole
2,4-di(1-methylbutyl)-5-(1,1-dimethylpropyl)imidazole
2,5-di(1-methylbutyl)-4-(1,1-dimethylpropyl)imidazole
2,4-di(1-methylbutyl)-5-(1,1-dimethylbutyl)imidazole
2,5-di(1-methylbutyl)-4-(1,1-dimethylbutyl)imidazole
2,4-di(1-methylbutyl)-5-(1,1-dimethylpentyl)imidazole
2,5-di(1-methylbutyl)-4-(1,1-dimethylpentyl)imidazole
2,4-di(1-methylbutyl)-5-(1,1-dimethylhexyl)imidazole
2,5-di(1-methylbutyl)-4-(1,1-dimethylhexyl)imidazole
2,4-di(1-methylbutyl)-5-(1-methylethyl)imidazole
2,5-di(1-methylbutyl)-4-(1-methylethyl)imidazole
2,4-di(1-methylbutyl)-5-(1,2-dimethylpropyl)imidazole
2,5-di(1-methylbutyl)-4-(1,2-dimethylpropyl)imidazole
More preferably, the imidazole is one of:
2-tertbutyl-4,5-di(1-methyl-1-ethylpropyl)imidazole 2-(1,1-dimethylpropyl)-4,5-di(1-methyl-1-ethylpropyl)imidazole
2-(1,1-dimethylbutyl)-4,5-di(1-methyl-1-ethylpropyl)imidazole
2-(1,1-dimethylpentyl)-4,5-di(1-methyl-1-ethylpropyl)imidazole
2-(1,1-dimethylhexyl)-4,5-di(1-methyl-1-ethylpropyl)imidazole
2-(1,1-dimethylhexyl)-4,5-di(1-methyl-1-ethylpropyl)imidazole
2-(1-methylethyl)-4,5-di(1-methyl-1-ethylpropyl)imidazole
2,4,5-tri(1-methyl-1-ethylpropyl)imidazole
2,4-di-ter-butyl-5-(1-methyl-1-ethylpropyl)imidazole
2,5-di-ter-butyl-4-(1-methyl-1-ethylpropyl)imidazole
2-tert-butyl-4-(1,1-dimethylpropyl)-5-(1-methyl-1-ethylpropyl)imidazole
2-tert-butyl-5-(1,1-dimethylpropyl)-4-(1-methyl-1-ethylpropyl)imidazole
2-tert-butyl-4-(1,1-dimethylbutyl)-5-(1-methyl-1-ethylpropyl)imidazole
2-tert-butyl-5-(1,1-dimethylbutyl)-4-(1-methyl-1-ethylpropyl)imidazole
2-tert-butyl-4-(1,1-dimethylpentyl)-5-(1-methyl-1-ethylpropyl)imidazole
2-tert-butyl-5-(1,1-dimethylpentyl)-4-(1-methyl-1-ethylpropyl)imidazole
2-tert-butyl-4-(1,1-dimethylhexyl)-5-(1-methyl-1-ethylpropyl)imidazole
2-tert-butyl-5-(1,1-dimethylhexyl)-4-(1-methyl-1-ethylpropyl)imidazole
2-(1,1-dimethylpropyl)-4-tert-butyl-5-(1-methyl-1-ethylpropyl)imidazole
2-(1,1-dimethylpropyl)-5-tert-butyl-4-(1-methyl-1-ethylpropyl)imidazole
2,4-(1,1-dimethylpropyl)-5-(1-methyl-1-ethylpropyl)imidazole
2-(1,1-dimethylpropyl)-4-(1,1-dimethylbutyl)-5-(1-methyl-1-ethylpropyl)imidazole
2-(1,1-dimethylpropyl)-5-(1,1-dimethylbutyl)-4-(1-methyl-1-ethylpropyl)imidazole
2-(1,1-dimethylpropyl)-4-(1,1-dimethylpentyl)-5-(1-methyl-1-ethylpropyl)imidazole
2-(1,1-dimethylpropyl)-5-(1,1-dimethylpentyl)-4-(1-methyl-1-ethylpropyl)imidazole
2-(1,1-dimethylpropyl)-4-(1,1-dimethylhexyl)-5-(1-methyl-1-ethylpropyl)imidazole
2-(1,1-dimethylpropyl)-5-(1,1-dimethylhexyl)-4-(1-methyl-1-ethylpropyl)imidazole
2-(1,1-dimethylpropyl)-4-(1-methylethyl)-5-(1-methyl-1-ethylpropyl)imidazole
2-(1,1-dimethylpropyl)-5-(1-methylethyl)-4-(1-methyl-1-ethylpropyl)imidazole
2-(1,1-dimethylpropyl)-4-(1,2-dimethylpropyl)-5-(1-methyl-1-ethylpropyl)imidazole
2-(1,1-dimethylpropyl)-5-(1,1-dimethylpropyl)-4-(1-methyl-1-ethylpropyl)imidazole
2-(1,1-dimethylbutyl)-4-tert-butyl-5-(1-methyl-1-ethylpropyl)imidazole
2-(1,1-dimethylbutyl)-5-tert-butyl-4-(1-methyl-1-ethylpropyl)imidazole
2-(1,1-dimethylbutyl)-4-(1,1-dimethylpropyl)-5-(1-methyl-1-ethylpropyl)imidazole
2-(1,1-dimethylbutyl)-5-(1,1-dimethylpropyl)-4-(1-methyl-1-ethylpropyl)imidazole
2,4-di(1,1-dimethylbutyl)-5-(1-methyl-1-ethylpropyl)imidazole
2,5-di(1,1-dimethylbutyl)-4-(1-methyl-1-ethylpropyl)imidazole
2-(1,1-dimethylbutyl)-4-(1,1-dimethylpentyl)-5-(1-methyl-1-ethylpropyl)imidazole
2-(1,1-dimethylbutyl)-5-(1,1-dimethylpentyl)-4-(1-methyl-1-ethylpropyl)imidazole
2-(1,1-dimethylbutyl)-4-(1,1-dimethylhexyl)-5-(1-methyl-1-ethylpropyl)imidazole
2-(1,1-dimethylbutyl)-5-(1,1-dimethylhexyl)-4-(1-methyl-1-ethylpropyl)imidazole
2-(1,1-dimethylpentyl)-4-tert-butyl-5-(1-methyl-1-ethylpropyl)imidazole
2-(1,1-dimethylpentyl)-5-tert-butyl-4-(1-methyl-1-ethylpropyl)imidazole
2-(1,1-dimethylpentyl)-4-(1,1-dimethylpropyl)-5-(1-methyl-1-ethylpropyl)imidazole
2-(1,1-dimethylpentyl)-5-(1,1-dimethylpropyl)-4-(1-methyl-1-ethylpropyl)imidazole
2-(1,1-dimethylpentyl)-4-(1,1-dimethylbutyl)-5-(1-methyl-1-ethylpropyl)imidazole
2-(1,1-dimethylpentyl)-5-(1,1-dimethylbutyl)-4-(1-methyl-1-ethylpropyl)imidazole
2-4-di(1,1-dimethylpentyl)-5-(1-methyl-1-ethylpropyl)imidazole
2-5-di(1,1-dimethylpentyl)-4-(1-methyl-1-ethylpropyl)imidazole
2-(1,1-dimethylpentyl)-4-(1,1-dimethylhexyl)-5-(1-methyl-1-ethylpropyl)imidazole
2-(1,1-dimethylpentyl)-5-(1,1-dimethylhexyl)-4-(1-methyl-1-ethylpropyl)imidazole
2-(1,1-dimethylhexyl)-4-tert-butyl-5-(1-methyl-1-ethylpropyl)imidazole
2-(1,1-dimethylhexyl)-5-tert-butyl-4-(1-methyl-1-ethylpropyl)imidazole
2-(1,1-dimethylhexyl)-4-(1,1-dimethylpropyl)-5-(1-methyl-1-ethylpropyl)imidazole
2-(1,1-dimethylhexyl)-5-(1,1-dimethylpropyl)-4-(1-methyl-1-ethylpropyl)imidazole
2-(1,1-dimethylhexyl)-4-(1,1-dimethylbutyl)-5-(1-methyl-1-ethylpropyl)imidazole
2-(1,1-dimethylhexyl)-5-(1,1-dimethylbutyl)-4-(1-methyl-1-ethylpropyl)imidazole
2-(1,1-dimethylhexyl)-4-(1,1-dimethylpentyl)-5-(1-methyl-1-ethylpropyl)imidazole
2-(1,1-dimethylhexyl)-5-(1,1-dimethylpentyl)-4-(1-methyl-1-ethylpropyl)imidazole
2,4-(1,1-dimethylhexyl)-5-(1-methyl-1-ethylpropyl)imidazole
2,5-(1,1-dimethylhexyl)-4-(1-methyl-1-ethylpropyl)imidazole
2-(1-methyl-1-ethylpropyl)-4-tert-butyl-5-(1,1-dimethylpropyl)imidazole
2-(1-methyl-1-ethylpropyl)-5-tert-butyl-4-(1,1-dimethylpropyl)imidazole
2-(1-methyl-1-ethylpropyl)-4-tert-butyl-5-(1,1-dimethylbutyl)imidazole
2-(1-methyl-1-ethylpropyl)-5-tert-butyl-4-(1,1-dimethylbutyl)imidazole
2-(1-methyl-1-ethylpropyl)-4-tert-butyl-5-(1,1-dimethylpentyl)imidazole
2-(1-methyl-1-ethylpropyl)-5-tert-butyl-4-(1,1-dimethylpentyl)imidazole
2-(1-methyl-1-ethylpropyl)-4-tert-butyl-5-(1,1-dimethylhexyl)imidazole
2-(1-methyl-1-ethylpropyl)-5-tert-butyl-4-(1,1-dimethylhexyl)imidazole 2-(1-methyl-1-ethylpropyl)-4-(1,1-dimethylpropyl)-5-(dimethylbutyl)imidazole
2-(1-methyl-1-ethylpropyl)-4-(1,1-dimethylpropyl)-5-(dimethylbutyl)imidazole
2-(1-methyl-1-ethylpropyl)-4-(1,1-dimethylpropyl)-5-(dimethylpentyl)imidazole
2-(1-methyl-1-ethylpropyl)-4-(1,1-dimethylpropyl)-5-(dimethylpentyl)imidazole
2-(1-methyl-1-ethylpropyl)-4-(1,1-dimethylpropyl)-5-(dimethylhexyl)imidazole
2-(1-methyl-1-ethylpropyl)-4-(1,1-dimethylpropyl)-5-(dimethylhexyl)imidazole
2-(1-methyl-1-ethylpropyl)-4-(dimethylpentyl)-5-(1,1-dimethylbutyl)imidazole
2-(1-methyl-1-ethylpropyl)-5-(dimethylpentyl)-4-(1,1-dimethylbutyl)imidazole
2-(1-methyl-1-ethylpropyl)-4-(dimethylpentyl)-5-(1,1-dimethylhexyl)imidazole
2-(1-methyl-1-ethylpropyl)-5-(dimethylpentyl)-4-(1,1-dimethylhexyl)imidazole
2,4-di(1-methyl-1-ethylpropyl)-5-tert-butylimidazole
2,5-di(1-methyl-1-ethylpropyl)-4-tert-butylimidazole
2,4-di(1-methyl-1-ethylpropyl)-5-(1,1-dimethylpropyl)imidazole
2,5-di(1-methyl-1-ethylpropyl)-4-(1,1-dimethylpropyl)imidazole
2,4-di(1-methyl-1-ethylpropyl)-5-(1,1-dimethylbutyl)imidazole
2,5-di(1-methyl-1-ethylpropyl)-4-(1,1-dimethylbutyl)imidazole
2,4-di(1-methyl-1-ethylpropyl)-5-(1,1-dimethylpentyl)imidazole
2,5-di(1-methyl-1-ethylpropyl)-4-(1,1-dimethylpentyl)imidazole
2,4-di(1-methyl-1-ethylpropyl)-5-(1,1-dimethylhexyl)imidazole
2,5-di(1-methyl-1-ethylpropyl)-4-(1,1-dimethylhexyl)imidazole These imidazoles can then be deprotonated to yield their respective imidazolate anions, which can then coordinate to barium, strontium, calcium or radium ions to, in turn, yield their respective complexes.

Preferably, the imidazolate's $R_1$ and $R_3$ are individually selected from the group consisting of tert-butyl, isopropyl, tert-amyl, neopentyl, adamantly, hexyl, cyclohexyl, propyl, butyl, isobutyl, pentyl, cyclopentyl, isopentyl, neopenty, norbornyl, bicyclo[2.2.1]heptyl, propyl, butyl, isobutyl, pentyl, isopentyl, dimethylbutyl, dimethylpentyl, dimethylhexyl, sec butyl, ethylmethylpropyl, isohexyl, isopentyl.

Preferably, the imidazolate's $R_2$ is a bulky group selected from the group consisting of tert-butyl, isopropyl, tert-amyl, neopentyl, adamantly, hexyl, hexyl, cyclohexyl, propyl, butyl, isobutyl, pentyl, cyclopentyl, isopentyl, neopenty, norbornyl, bicyclo[2.2.1]heptyl, propyl, butyl, isobutyl, pentyl, isopentyl, dimethylbutyl, dimethylpentyl, dimethylhexyl, sec butyl, ethylmethylpropyl, isohexyl, isopentyl.

Most preferably, the imidazolate is
2,4,5-tri-tert-butylimidazolate
2-tert-butyl-4,5-di-(1,1-dimethylpropyl)imidazolate
2-(1,1-dimethylbutyl)-4,5-di-tert-butylimidazolate
2-(1,1-dimethylbutyl)-4,5-di-(1,1-dimethylpropyl)imidazolate; and their barium, strontium, magnesium and calcium salts.

In another aspect, the present invention teaches compounds comprising one or more polysubstituted imidazolate anions coordinated to a metal selected from the group consisting of barium, strontium, magnesium, calcium or radium or mixtures thereof.

Alternatively, one imidazolate anion can be substituted with a second non-imidazolate anion. In addition, the imidazolate anion may also bear a substituent, which is also deprotonated to yield a dianionic species, and this dianion is coordinated to a metal, such as barium, strontium, magnesium, calcium or radium or mixtures thereof.

Synthesis of the novel compounds and their use to form BST films is also contemplated.

To understand the unique character of these ligands, it is instructive to consider the structure and substitutional numbering system of unsubstituted imidazole, as shown in Formula A. Note that the ring numbering system indicates that when all three carbon atoms of the imidazole ring are substituted with alkyl groups, then the resulting molecule would be called a 2,4,5-trialkylimidazole.

Formula A

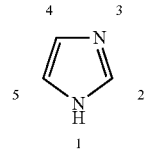

When the N—H group of imidazole is deprotonated at position 1, the resulting formal negative charge of the anion thus created is delocalized throughout the five membered ring. However, if such an anion coordinates to metal cations it will typically do so through both of the nitrogen atoms, not involving the three carbon atoms of the ring. In this way, the imidazole anion most typically behaves as a linear 'bridging anion' between metal centers.

This very strong tendency for imidazolates to linearly bridge metal cations is frequently utilized as a technique to build framework complexes, where the imidazole act as a molecular scaffold to link metals cations together, as illustrated in Formula B. Being highly associated, such structures are involatile.

Formula B

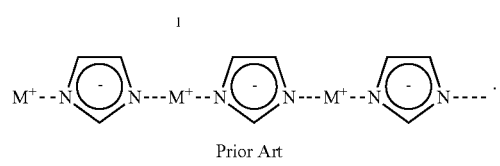

Prior Art

The novel imidazole ligands of the present invention are unique in that they are substituted in at least the 2 and 5 positions, more preferably the 2,4 and 5 positions on the imidazole ring using sufficiently bulky groups such as tert-butyl, that when the imidazole is deprotonated to give an imidazolate anion, it does not coordinate to a metal to form a highly associated structure as in Formula B, but rather other modes of coordination to the metal become possible. One possible mode of coordination then becomes an 'eta-5' mode, where the plane of the five membered ring is positioned sideways to the metal ion. This then permits the metal to bond to all five atoms of the imidazolate ring, as shown in Formula C, where R represents bulky alkyl type groups.

Bulky groups for the purpose of the present invention are groups which have sufficient 3-dimensional spacial form to create the steric hindrance needed so that metals bonding with the imidazolates of the present invention are enabled to be preferably bonded in the 'eta-5' bonding or 'end on' 'eta-1' bonding of Formulae C and D respectively. Additionally, the bonding modes between these two extremes are also possible, such as: eta-2, eta-3 and eta-4.

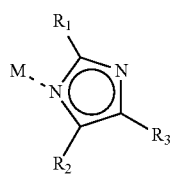

Formula C

More preferably, bulky groups for the purpose of the present invention are groups which have sufficient 3-dimensional spacial form to create sufficient steric hindrance so that metals bonding with the imidazolates of the present invention are enabled to be bonded in the 'eta-5' bonding of Formula D.

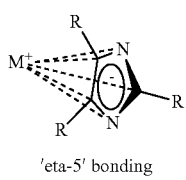

Formula D

'eta-5' bonding

The structure depicted in Formula D represents an unexpected result in that the vast preponderance of imidazole anions (ie imidazolates) do not bind in an 'eta-5' or sideways manner, but rather linearly only though the nitrogen atoms, as in Formula B.

In the Cambridge crystallographic data base there is only one example of an eta-5 metal-to-imidazolate ion coordination (M. Tadokoro, T. Shiomi, K. Isob, K. Nakasuji, *Inorganic Chem.* 40 5476-5478 (2001)), and it occurs in an involatile mixed metal polymeric coordination compound, rather than in the dicreet and volatile metal complexes of the present invention, further underscoring the unique character of the present invention's novel imidazole ligands.

Additionally, the imidazolate anions of this disclosure can also bond in a novel 'end on' manner as shown in Formula C where the bulky substituents permit the metal to bond only to one of the imidazolate nitrogens. This is illustrated in FIG. 8 where the two terminal imidazolate anions of di-strontium tetra(2-tert-butyl-4,5-di(1,1-dimethylpropyl)imidazolate) are seen to bind to strontium by only one nitrogen. While not wishing to be bound by theory, it is also anticipated that other novel bonding modes exist between the two extremes of eta-5 and eta-1, where only two, three or four of the imidazolate ring atoms participate in bonding to the metal.

Bulky groups can comprise $C_{3-12}$ groups, preferably branched alkyl, cyclic or aromatic, and optionally further derivatized with other functional groups such as amine, alkoxy, hydroxyl, carboxylic, substituted amine and similar derivatives. Alkanes, alkenes, alkynes, cyclic forms of the same, aromatics, and their derivatives are all contemplated as bulky groups, as long as they meet the requirement of having sufficient bulk in the form of 3-dimensional spacial form to induce eta-4, eta-3, to 2 or eta-1, and more preferably 'eta-5' bonding of the imidazole with metals. Other suitable bulky alkyl groups include, but are not limited to, isopropyl, tert-amyl, neopentyl, adamantly, hexyl, cyclohexyl, propyl, butyl, isobutyl, tertbutyl, pentyl, isopentyl, neopenty, norbornyl, bicyclo[2.2.1]heptyl, $C_9$-$C_{20}$ alkylphenyl, $C_1$-$C_{10}$ alkoxy; $C_1$-$C_{10}$ alkylamine; $C_1$-$C_{10}$ alkyl functionalized with a heteroatom substituted ring structure selected from the group consisting of imidazole, pyrrole, pyridine, furan, pyrimidine, pyrazole; $C_1$-$C_{10}$ alkyl functionalized with an amide group; $C_1$-$C_{10}$ alkyl functionalized with an ester group and mixtures thereof.

As can be seen in FIGS. 4, 6, 10, 13 and 15, the bulky groups can induce 'eta-5' bonding, as exemplified by the terminal imidazolate anions present in these structures. However, the central imidazolates act as 'bridging' anions connecting the two metal centers together, where the axis of the metal-nitrogen bonds are not in the plane of the imidazolate ring, but rather both pointed to one side of the plane. Not wishing to be bound by any theory, it is believed that the bulky groups induce a preference for, eta-4, eta-3, eta-2 or eta-1, and more preferably eta-5 bonding, and when such bonding is satisfied, additional linear non-planar bonding is also permitted by the bulky groups, possibly due to steric hindrance effects after two bulky group substituted imidazoles are bound to the metal. Thus, in the present invention, when the bulky groups are characterized by stating they impart a property to the imidazolate to bond with metals in an, eta-4, eta-3, eta-2 or eta-1, and more preferably 'eta-5 bond', this does not preclude additional bonding in linear fashion in addition to 'eta-5' etc, but merely describes a favored or preferred bonding form. Without the bulky groups, these imidazolates would not exhibit the property to favor eta-4, eta-3, eta-2, eta-1, and more preferably eta-5 i.e., non-planar bridging bonding.

Unsubstituted phenyl does not display sufficient bulkiness to be included in the definition of bulky groups, due to its largely planar 3-dimensional shape, whereas, cyclohexane has sufficient bond angles to constitute a bulky group.

In addition, these alkyl substituents can also be functionalized with coordinating groups such as ether, crown ether, amine, amide, cyano, isonitrile, imine, amidinine, ester, pyridine, imidazole, pyrrole, pyrazole, oxazole, isooxazole, furan, pyrimidine, furfuryl, oxirane, aziridine, oxolane, 1,3-dioxolane, 1,4-doxane, 1,3,5-trioxane, pyrrolidine, piperidine, quinuclidine. They can also be functionalized with groups capable of being deprotonated, so that with the imidazole also being deprotonated, they form di-anions, which then can be coordinated to metal centers. Such groups include, but are not limited to; cyclopentadiene, pyrrole, beta-diketone, beta-ketoimine, beta-diimine, alcohol, amine, amide, pyrrole, phenol, carboxylate, amidinate, guanidinate.

Figure 5:
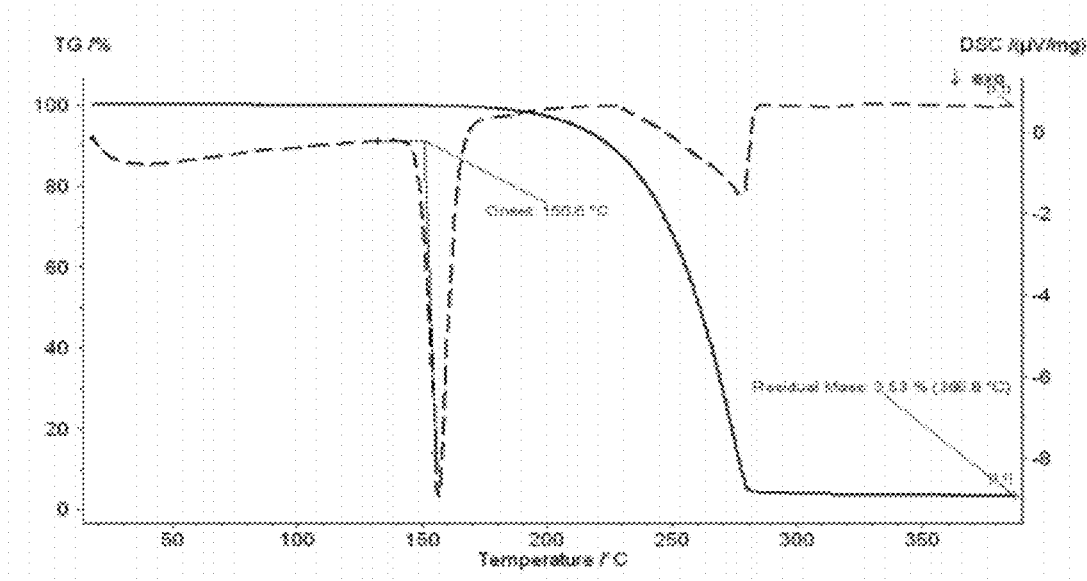
FIG. 5 is the thermogravimetric analysis (TGA)/differential scanning calorimetry (DSC) result for di-barium tetra(2,4,5-tri-tert-butylimidazolate), wherein the TGA is a solid line and the DSC is a dashed line.
Figure 16:
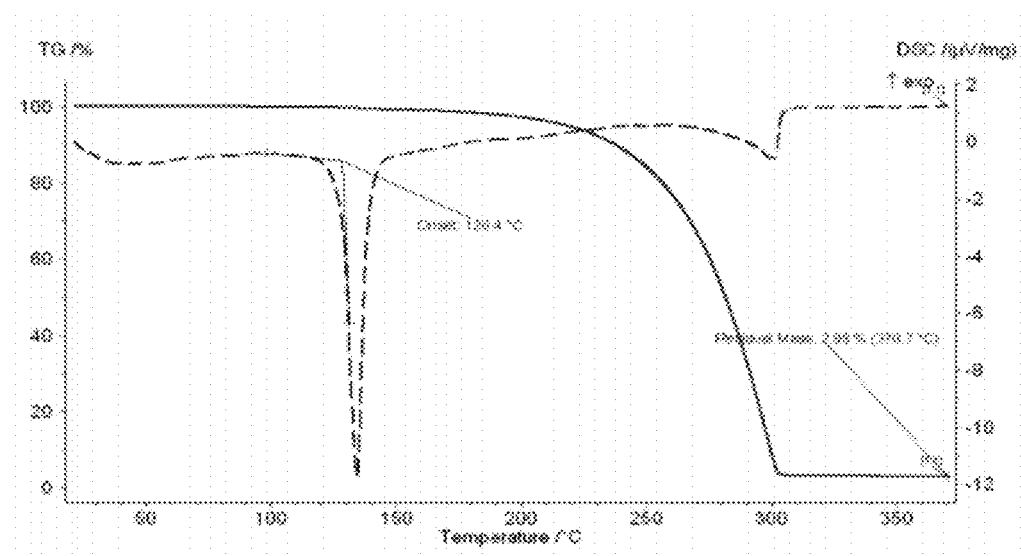
FIG. 16 is the TGA/DSC result for di-barium tetra(2-(1,1-dimethylbutyl)-4,5-di-tert-butyl)imidazolate), wherein the TGA is a solid line and the DSC is a dashed line.
Figure 17:
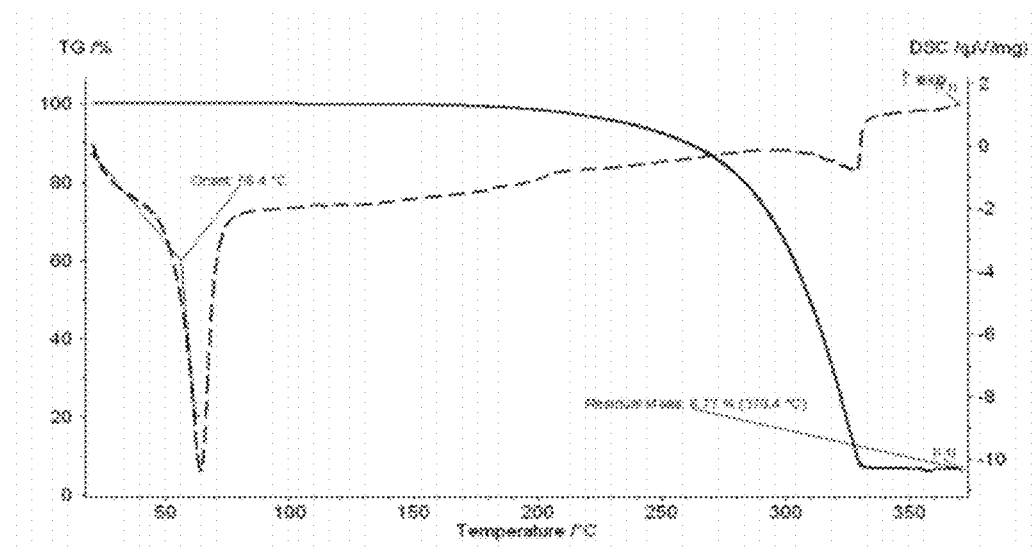
FIG. 17 is the TGA/DSC result for di-barium-tetra(2-(1,1-dimethylbutyl)-4,5-di(1,1-dimethylpropyl)imidazolate), wherein the TGA is a solid line and the DSC is a dashed line.

The effectiveness of tert-butyl and similar three dimensional bulky groups versus planar groups, such as phenyl, in creating volatile alkaline earth compounds is illustrated by the preparation of the barium complex of 2,4,5-triphenylimidazole, i.e., where $R^1$=$R^2$=$R^3$=phenyl, described in Example 20, where no volatile barium species could be isolated from the reaction mixture. This is in sharp contrast to the barium complexes of 2,4,5-tri-tert-butylimidazole and 2-(1,1-dimethylbutyl)-4,5-di-tert-butylimidazole, described in Examples, 8 and, 16 respectively, which shows exceptional volatility as illustrated by FIGS. 5 and 16, respectively.

One of the most well known family of barium compounds for ALD and CVD applications are the 'barocene' compounds, where the barium ion is coordinated to two multi alkyl functionalized cyclopentadienyl anions, such as tri-tert-butylcyclopentadienyl (t-$Bu_3$Cp). TGA was used to screen the volatility/thermal stability of these compounds. In this technique, a sample of the barium compound is placed in a microbalance pan, which is heated at a steadily increasing rate under a steady stream of dry inert gas, such as nitrogen. As the temperature of the sample increases, the barium compound evaporates at an ever increasing rate, and this weight loss is detected by the microbalance. Eventually, the evaporation ceases, and, for barium, there is typically a residue of involatile material.

A low level of residue is highly desirable, as this translates to a controlled evaporation of the barium being possible, if it is used as a source precursor compound for ALD or CVD processes. In addition, for CVD or ALD processes, many metal precursors, such as barium precursors, are dissolved in a solvent, and this solution is vaporized in a direct liquid injection (DLI) system. Basically, this comprises delivering a precisely controlled flow of solution into a vaporizer, where the solution and its dissolved solute are rapidly heated and vaporized under reduced pressure. The resulting vapor is then transported into the CVD or ALD reactor. Typically, there are miniaturized nozzles and narrow bore tubes used inside the vaporizer at the point where the solution is nebulized or simply introduced into the vaporization temperature. If the solute does not fully evaporate and an involatile residue is formed, these fine bore tubes can become obstructed, thereby preventing any further flow of solution.

For these reasons, it is highly desirable for the involatile residue observed in the TGA experiment to be as low as possible to avoid the accumulation of obstructing residues, for the best possible DLI performance. This is especially important in a commercial manufacturing environment, where such an equipment failure is prohibitively expensive. It is noted that the TGA results in FIGS. 5 and 16 for the molecules di-barium tetra(2,4,5-tri-tert-butylimidazolate) and di-barium tetra(2-(1,1-dimethylbutyl)-4,5-di-tert-butylimidazolate) respectively show involatile residues of only 3.53 and 2.99 wt %, respectively, which are exceedingly low values, indicating the excellent vaporization characteristics and superior volatility of the metal imidazolate complexes of this disclosure, compared to their barocene homologues, such as; $Ba(tBu_3C_5H_2)_2$(tetrahydrofuran). The latter is reported to have a TGA involatile residue of 4.2 wt % (Timo Hatanpaa, Marko Vehkamaki, Ilpo Mutikainen, Jarno Kansikas and Mikko Ritala "Synthesis and characterization of cyclopentadienyl complexes of barium: precursors for atomic layer deposition of $BaTiO_3$" Dalton Trans., 2004, p. 1181-1188). However, since this TGA result is of the tetrahydrofuran adduct of the barocene, rather than pure barocene, it appears artificially low, since some of the weight loss is incurred simply from loss of tetrahydrofuran. Accounting for this discrepancy yields a corrected value of 675/603×4.2=4.7 wt %, where 675 and 603 represent the molecular weights of the barocene tetrahydrofuran adduct and pure barocene, respectively.

Figure 22:
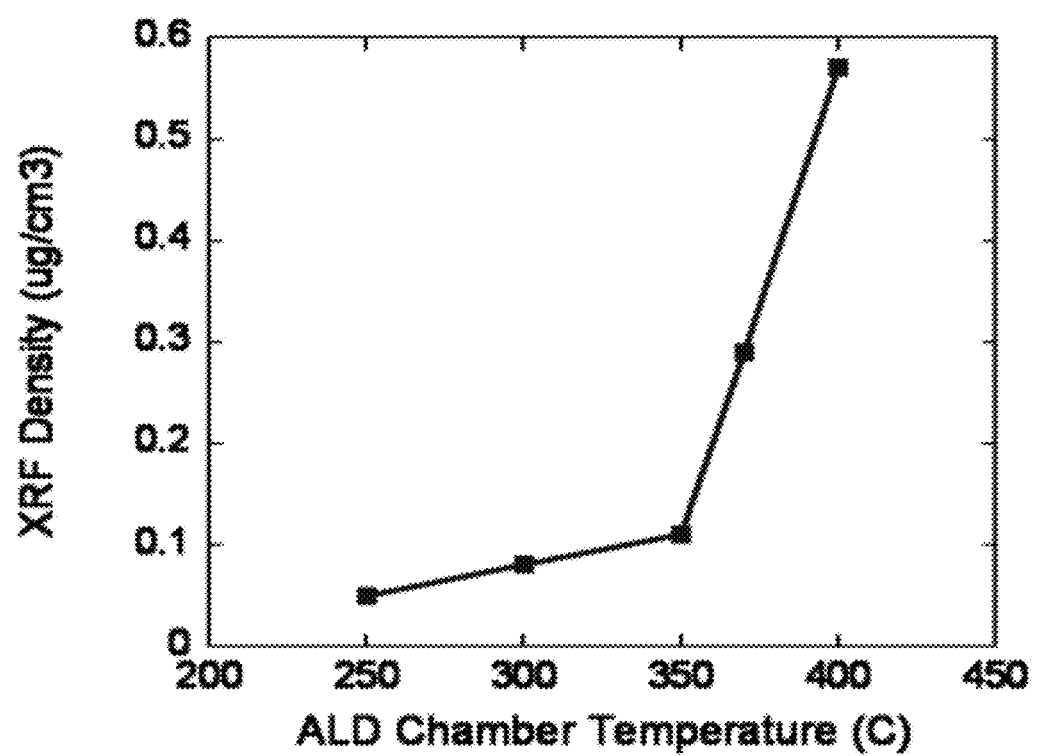
FIG. 22 illustrates the thermal stability of di-strontium tetra(2-tert-butyl-4,5-di-(1,1-dimethylpropyl)midazolate).

The excellent thermal stability of di-strontium tetra(2-tert-butyl-4,5-di(1,1-dimethylpropylimidazolate) is illustrated in Example 22 and FIG. 22 where, under ALD conditions, pulses of di-strontium tetra(2-tert-butyl-4,5-di(1,1-dimethylpropylimidazolate) are shown to not thermally degrade on a substrate surface until >350° C.

Preferred metal imidazolates include; Di-barium tetra(2,4,5-tris-t-butylimidazolate); Di-barium tetra(2-tert-butyl-4,5-di-(1,1-dimethylpropyl)imidazolate); Di-barium tetra(2-(1,1-dimethylbutyl)-4,5-di-tert-butylimidazolate); and, Di-barium tetra(2-(1,1-dimethylbutyl)-4,5-di-(1,1-dimethylpropyl)imidazolate); Di-strontium tetra(2,4,5-tris-t-butylimidazolate); Di-strontium tetra(2-tert-butyl-4,5-di-(1,1-dimethylpropyl)imidazolate); Di-strontium tetra(2-(1,1-dimethylbutyl)-4,5-di-tert-butylimidazolate); and, Di-strontium tetra(2-(1,1-dimethylbutyl)-4,5-di-(1,1-dimethylpropyl)imidazolate).

The present invention is also directed to the synthesis and use of new and novel barium, strontium, magnesium, radium and calcium substituted imidazolate-based compounds and their solutions for vapor delivery upon direct liquid injection, wherein the substituted, preferably alkyl groups, of the imidazolate ligand anion are bulky hydrocarbons, such as: tert-butyl, tert-amyl, adamantly, cyclohexyl, neopentyl, etc.; and can be nitrogen or oxygen containing alkyl, such as: tertiary amine or ether groups. Additionally, these new compounds can also coordinate other neutral ligands, such as ethers or amines or alkoxyamines. Electron withdrawing groups, such as nitro or acyl, can also be present as a imidazolate ring substituent.

While not wishing to be bound by theory, groups, such as nitro, enhance the coordination of added neutral ligands, such as: tetrahydrofuran (THF), diglyme, 18-crown-6 crown ether, by rendering the imidazolate anion less electron donating to barium or strontium or other alkaline earth metal, and hence, increase the Lewis acidity of the metal towards added ligands, and hence, increase their affinity to the metal. Achieving this enhanced coordination permits the entire barium or strontium compound, with coordinated ligands, such as THF, to vaporize intact as one complete compound, rather than releasing this coordinated ligand first.

The present invention also includes a novel method of synthesizing the barium, strontium, magnesium, radium or calcium compounds by direct metallization of the imidazolate ligands using a metal reagent, such as barium or strontium hexamethyldisilazane or barium or strontium hydride, thereby providing an efficient alternative to using the standard metathesis type of reaction, where the imidazole is first treated with a metal hydride, such as sodium hydride, to form a sodium imidazolate, which is then in turn reacted with a barium or strontium halide, such as barium or strontium iodide, etc.

Other novel techniques for synthesizing these new compounds include, but are not limited to: direct reaction of the imidazole ligands with barium, strontium, magnesium or calcium metal as a vapor or as a finely dispersed powder; or by reaction with barium or strontium metal, etc., in the presence of ammonia; or by reacting the imidazole ligands with barium metal in the presence of an amine, such as hexamethyldisilazane, with ammonia. The novel compounds may also be prepared by electrochemical syntheses.

Additionally, a wide variety of metals and metalizing agents can be used to effectively deprotonate the imidazole ligands prior to reacting with a barium, strontium, magnesium, radium or calcium source. Such reagents include, but are not limited to: lithium metal, n-butyl lithium, n-hexyl lithium, sec-butyl lithium, tert-butyl lithium, lithium diisopropylamide, potassium hydride, potassium hexamethyldisilazane, sodium hydride, sodium metal, sodium hexamethyldisilazane, potassium metal, barium metal, sodium t-butoxide, potassium t-butoxide. Barium sources include, but are not limited to: barium iodide, barium bromide, barium trifluoroacetate, barium hexafluoroacetylacetone, barium trifluoroacetylacetonate, barium acetyacetonate, barium diimine, barium ketoimine, barium amidinate, barium guanidinate, barium amide, barium alkoxide, barium amide, barium carbonate, barium acetate, barium carbonate, barium formate, barium propionate, barium phenoxide, barium hydroxide, barium fluoride, barium amidinate, barium amidinine and the strontium, magnesium, radium and calcium analogs to the barium sources.

The novel polysubstituted imidazole barium, magnesium, calcium, radium or strontium compounds of the present invention are selected from the following structures in Formulae E, F G and H, where $R^1$, $R^2$, $R^3$ and are each individually selected to be acyl, formyl, nitro, amido, H, $C_1$-$C_{10}$, primary, secondary or tertiary alkyl, primary, secondary or tertiary alkene or alkyne $C_1$-$C_{10}$alkoxy, $C_9$-$C_{20}$ alkylphenyl, alkylamine, $C_1$-$C_{10}$ alkyl functionalized with a heteroatom substituted ring structure, such as: imidazole, pyrrole, pyridine, furan, pyrimidine, pyrazole, pyrrole, $C_1$-$C_{10}$ alkyl functionalized with an amide group, and $C_1$-$C_{10}$ alkyl functionalized with an ester group; and each n independently=0-4, preferably each n independently=0, 1 or 2. Note that neutral ligand-free molecules, where n=zero in $(L)_n$ to indicate that there is no (L) ligand coordinated, are also described.

Mixed complexes can also be created where $R^{1-3}$ are varied differently among imidazolate anions, and then this mixture is complexed to barium, or other alkaline earth metal, so that the resulting barium other alkaline earth metal complex represents a mixture. For example, if two different imidazolate anions $I^1$ and $I^2$ are mixed together, and then complexed to barium, three unique barium complexes can be made; i.e., $Ba((I^1)_2$, $Ba(I^1I^2)$ and $Ba(I^2)_2$. If three different imidazolate anions $I^1$, $I^2$ and $I^3$ are mixed, and then complexed to barium, six barium complexes are formed; i.e., $Ba((I^1)_2$, $Ba(I^1I^2)$, $Ba(I^1I^3)$, $Ba(I^2)_2$, $Ba(I^2I^3)$ and $Ba(I^3)_2$. These mixtures will be either liquids or highly soluble formulations for DLI. Also, the groups $R^{1-3}$ of one imidazolate anion can be joined together or can be joined to the $R^{1-3}$ groups of another imidazolate anion to connect the two anions together. The neutral ligand (L) is selected from aliphatic $C_1$-$C_{20}$ ether or polyether, crownethers, such as 18-crown-6, amine or polyamine, alkoxyamine or polyalkoxyamine, amide or polyamide, ester or polyester, aromatic ether, aromatic ester, aromatic amide, aromatic amine, pyridine, imidazole, pyridine, pyrazine, furan, alkylcarbonate or pyrrole. Additionally, groups $R^1$, $R^2$, $R^3$ and can be linked together to form ring structures, These ring structures can also be aromatic.

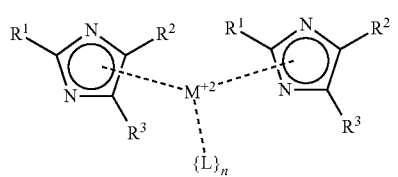

Formula E

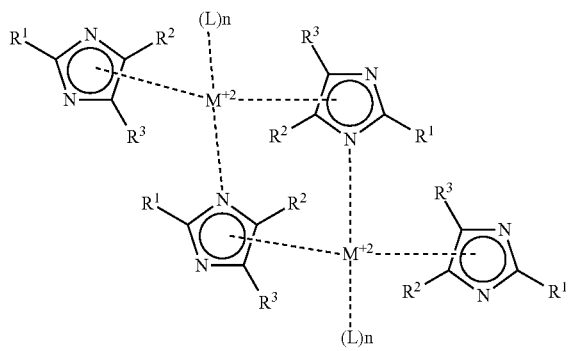

Formula F

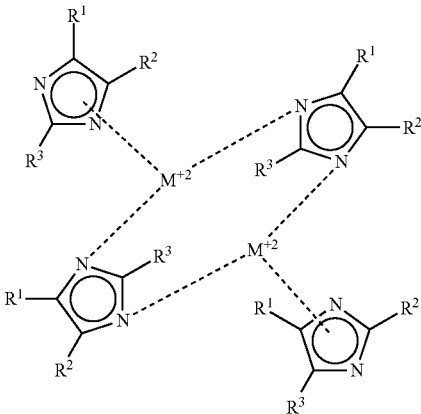

Formula G

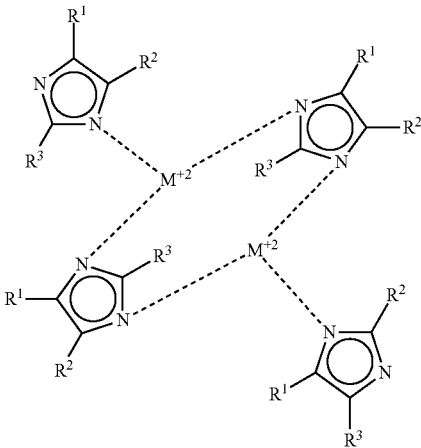

Formula H

It is noteworthy that the dimeric compounds in Formulas F G and H constitute starting materials from which neutral ligands, such as diglyme, can be added to create adduct complexes.

In Formulae E, F, G and H, M is a Group 2 metal selected from: magnesium, calcium, strontium, barium, radium, preferably strontium and barium, more preferably barium.

In addition to the above complexes, while not wishing to be bound by theory, mixed barium complexes can also be made, where one polyalkylated imidazolate anion and one other organic or inorganic anion coordinate to barium to make a complete complex. Examples of such alternative anions include, but are not limited to: beta-diketonates, acetates, ketoiminates, diimines, alkoxides, amides, hydrides, beta-ketoesters, amidinates, guanidinates, cyclopentadienyl, cyanide, isocyanide, formate, oxalate, malonate, phenoxide, thiolate, sulfide, nitrate, alkyl, silylalkyl, fluoroalkyl, aryl, imidazolate. Other alkaline earth metal complexes, as described above, are also contemplated.

Several advantages can be achieved through these metal-containing polyalkylated imidazoles as precursors for chemical vapor deposition or atomic layer deposition, and these include:

An ability to grow ALD and CVD metal oxides and mixed metal oxides, such as; STO or BST, at high growth rates up to and beyond one monolayer per cycle;

An ability to grow crystalline metal oxide and mixed metal oxides films, such as; STO and BST, directly under ALD or CVD process conditions;

An ability to form metal imidazole complexes of asymmetrically alkylated imidazolates to give low melting or liquid precursors;

An ability to form reactive complexes in good yield;

An ability to form monomeric thermally stable complexes, particularly strontium and barium complexes, coordinated with one kind or mixed kind of ligand, thus achieving higher vapor pressure than that of the known strontium and barium precursors. The known strontium and barium precursors are either polymeric complexes with lower vapor pressure or monomeric compounds with low thermal stability or with relatively high levels of involatile residues;

An ability to form highly conformal metal oxide thin films suited for use in microelectronic devices;

An ability to enhance the surface reaction between the metal-containing alkylated imidazolate anion and the surface of a substrate due to the high chemical reactivity of the complexes; and, An ability to tune the physical properties of these metal-containing polysubstituted imidazolate anions via a change in the $R^{1-3}$ groups.

Additionally, metal complexes can also be made by coordinating two different polysubstituted imidazolate anions to a metal center, such as barium, such that the two ligands experience an optimal 'fit' or 'interlock' with each other and around the metal, in such a way as to provide an adequate coordination sphere to create a stable monomeric complex.

While not wishing to be bound by theory, the molecules of this disclosure are excellent precursors for use in CVD or ALD processes for depositing alkaline earth metal oxide containing films, by reacting them together either sequentially or simultaneously with an oxidizer, such as: water, alcohol, oxygen, ozone, nitrous oxide, nitrogen dioxide, hydrogen peroxide or combinations thereof either in the presence or absence of an applied plasma discharge. Additionally, barium and strontium molecules of this disclosure can be reacted with a titanium precursor, such as: a titanium alkoxy/diketonate, titanium alkoxy/ketoester, titanium alkoxide, titanium cyclopentdienyl, titanium amide titanium imidazolate containing precursor, titanium pyrrolyl containing precursor or combinations thereof, in a CVD, pulsed CVD or ALD mode or hydrid pulsed CVD/ALD process to deposit BST (barium strontium titanate) films, which are highly prized, due to their high dielectric constant. Additionally, the barium complexes of this disclosure can be reacted with strontium ketoiminates and titanium precursors, such as: a titanium alkoxy/diketonate, titanium alkoxy/ketoester, titanium alkoxide, titanium cyclopentdienyl, titanium amide titanium imidazolate containing precursor, titanium pyrrolyl containing precursor or combinations thereof, in a CVD, pulsed CVD or ALD or hydrid pulsed CVD/ALD mode to deposit a BST film.

These new precursor molecules are able to deliver exceptionally high deposition rates, due to their ability to engage in highly novel modes of surface adsorption and reaction. Thus, when using the novel precursor, a deposition rate of >2.5 Angstroms of strontium oxide per cycle at 350° C. is achieved representing ~5 times a typical growth rate. Such an enhancement in growth per cycle is critically important, because it permits a greater throughput of wafers per unit time in commercial production, thus representing a substantial saving. Further, it is believed that the novel imidazolate ligands of this disclosure will similarly permit enhanced growth rates of other metals and metal containing films.

The precursors of this disclosure are highly suitable for use as volatile precursors for ALD, CVD, pulsed CVD, plasma enhanced ALD (PEALD) or plasma enhanced CVD (PECVD) for the manufacture of semiconductor type microelectronic devices, such as microcapacitor cells for memory applications such as DRAM devices. They are also highly useful for the manufacture of pyrodetector devices.

The precursors of this application can also readily be dissolved into a wide range of solvents, and the resulting solutions used in DLI mode to provide a vapor stream of these precursors into an ALD or CVD reactor. Being of low melting point, they are exceptionally soluble, including solubility in: alkylethers, alkylamines, alkoxyamines, aromatic ethers, aromatic amines, amides, esters and hydrocarbon solvents. The latter two species are particularly attractive, due to their ability to be dried to sub-ppm levels of water. Solvents that are exemplary of the solvents that can be used in the present invention are amino ethers, such as BL-19, glymes such as dipropyleneglycoldimethylether, e.g., DPGDME, pentamethyl-diethylene triamine, N,N-dimethylcyclohexylamine, N-methyldicyclohexylamine, Dimethyl-4-morpholine ethamine, Anisole(methoxybenzene), Phenetole (ethoxybenzene), toluene, mesitylene, cumene (isopropylbenzene), p-cymene (4-isopropyl toluene), 1,3-diisopropylbenzene, octane, dodecane, 1,2,4-trimethylcyclohexane, n-butylcyclohexane, and decahydronaphthalene (decalin). The precursors of this application can also be stored and used in stainless steel containers.

The precursors of this application can also be mixed with other suitable metal precursors, and the mixture used to deliver both metals simultaneously for the growth of a binary metal oxide or nitride films. For example, strontium precursors of this disclosure can be mixed with suitable titanium precursors, including imidazolate based titanium precursors, for the growth of strontium titanate (STO) films. Similarly, barium precursors of this disclosure can be mixed with suitable strontium precursors, including imidazolate based strontium precursors, with suitable titanium precursors, including imidazolate precursors, for the growth of barium strontium titanate (BST) films. Similarly, barium precursors of this disclosure can be mixed with suitable titanium precursors, including imidazolate based titanium precursors, for the growth of barium titanate (BTO) films.

The present invention is also a method of depositing a metal containing film by ALD or CVD comprising the use of the metal imidazolate structures of the present invention described above.

Preferably, the present invention includes a method of depositing a metal containing film by reacting a metal imidazolate structure of the present invention with an oxidant selected from the group consisting of water, alcohol, oxygen, ozone, nitrous oxide, nitrogen dioxide, hydrogen peroxide or combinations thereof to grow a metal containing film selected from the group consisting of barium oxide, strontium oxide, magnesium oxide, calcium oxide or radium oxide and mixtures thereof, using a reactor pressure between 0.001-1000 Torr and a temperature from 0-1000° C.

More preferably, this method results in a deposition of barium oxide of >1 Angstrom per cycle. Even more preferably, the deposition of barium oxide is >1.5 Angstrom per cycle. Still more preferably, the deposition of barium oxide is >2 Angstrom per cycle.

Alternately, the method results in the deposition of strontium oxide of >1 Angstrom per cycle. Preferably, the deposition of strontium oxide is >1.5 Angstrom per cycle. More preferably, the deposition of strontium oxide is >2 Angstrom per cycle.

In one embodiment, the method of the present invention includes reacting a Ba and Sr imidazolate structure of the present invention with alternating pulses of titanium precursors selected from the group consisting of titanium alkoxide, titanium alkoxide/diketonate, titanium cyclopentadienyl, titanium amide, titanium imidazolate and mixtures thereof in an ALD or pulsed CVD mode to grow BST films.

In another embodiment, the present invention is a method of reacting a Sr imidazolate structure of the present invention with alternating pulses of titanium precursors selected from the group consisting of titanium alkoxide, titanium alkoxide/diketonate, titanium cyclopentadienyl, titanium amide titanium imidazolate and mixtures thereof in an ALD or pulsed CVD mode to grow STO films.

A further embodiment is a method of reacting a Ba imidazolate structure of the present invention with alternating pulses of titanium precursors selected from the group consisting of titanium alkoxide, titanium alkoxide/diketonate, titanium alkoxy/ketoester, titanium cyclopentadienyl, titanium amide titanium imidazolate and mixtures thereof in an ALD or pulsed CVD mode to grow BTO films.

A still further embodiment is a method of reacting a barium imidazolate structure of the present invention with a strontium compound selected from the group consisting of strontium ketoiminate, strontium diketonate and mixtures thereof and a titanium compound selected from the group consisting of titanium alkoxide, titanium alkoxide/diketonate, titanium alkoxy/ketoester, titanium cyclopentadienyl, titanium amide and mixtures thereof, in an ALD, CVD or pulsed CVD to grow films of BST.

Yet another embodiment is a method of reacting an imidazolate structure of claim 13 with halide gases selected from the group consisting of HCl, HF, $SiCl_4$, HBr and mixtures thereof to grow $MX_2$ where X=halide and M is selected from the group consisting of Ba, Sr, Mg, Ca, Ra and mixtures thereof, in an ALD, CVD or pulsed CVD mode.

A method of synthesizing an imidazolate structure of the present invention by direct metallization of an imidazole with a metal reagent selected from the group consisting of n-butyl lithium, n-hexyl lithium, sec-butyl lithium, tert-butyl lithium, lithium diisopropylamide, potassium hydride, sodium hydride, sodium metal, potassium metal, sodium t-butoxide, potassium t-butoxide, potassium hexamethyldisilazane, sodium hexamethyldisilazane and then reacting the resulting product with a reactant selected from the group consisting of: alkaline earth metal iodide, alkaline earth metal acetate, alkaline earth metal carboxylate, alkaline earth metal carbonate, alkaline earth metal formate, alkaline earth metal bromide, alkaline earth metal trifluoroacetate, alkaline earth metal hexafluoroacetylacetone, alkaline earth metal trifluoroacetylacetone, alkaline earth metal acetyacetonate, alkaline earth metal diimine, alkaline earth metal ketoimine, alkaline earth metal amidinate, alkaline earth metal guanidinate and mixtures thereof.

A method of directly synthesizing an imidazolate structure of the present invention by reacting a polylalkylated imidazole using a reagent selected from the group consisting of: an alkaline earth metal amide, alkaline earth metal phenoxide, alkaline earth metal hydroxide, alkaline earth metal alkyl, alkaline earth metal aryl and mixtures thereof.

In an alternate embodiment, the present invention is a method of synthesizing an imidazolate structure of the present invention by reaction of an imidazole with an alkaline earth metal in the presence of ammonia.

A further alternate is a method of synthesizing an imidazolate structure of the present invention by reacting an imidazole with an alkaline earth metal in the presence of an amine with ammonia.

The present invention is also a method to grow dielectric films selected from the group consisting of: STO and BST using the mixture of metal imidazolates of the present invention to form micro-electronic devices selected form the group consisting of: dynamic random access memory (DRAM) memory cells and pyrometric devices.

Alternately, the present invention is a method of manufacturing microelectronic devices selected from the group consisting of: non-volatile ferroelectric microelectronic memory devices, display phosphors for electroluminescent displays, high Tc superconducting devices using the imidazolate structures of the present invention.

In yet another embodiment, the present invention is a method of growing a metal oxide or nitride film by ALD or CVD comprising; providing a barium or strontium imidazolate structure of the present invention in conjunction with titanium sources dissolved in a solvent selected from the group consisting of: an ether, aminoether, amide, ester, aromatic or hydrocarbon solvent and delivering the resulting solution by a DLI system to provide a vapor stream of the resulting solution to grow the metal oxide or nitride film by ALD or CVD.

EXAMPLES

Example 1

Synthesis of 2,5-di-tertbutylimidazole 5.44 g (0.04 moles) of 2,2-dimethylpropanimideamide hydrochloride were mixed with 7.2 g (0.04 moles) of 1-bromopinacolone and 11.2 g of triethylamine in 16.0 g of diethylformamide (DEF) and stirred at room temperature for 7 days. The reaction mixture was then poured into water and extracted three times with 50 ml units of hexane. The hexane fractions were combined and washed three times with 50 ml aliquots of water. The hexane layer was then stirred with 5 g of anhydrous magnesium sulfate over night. The hexane was then removed by vacuum down to a volume of 5 ml to yield a fine suspension. This was filtered and the resulting solid washed with fresh hexane to yield 4.22 g (59% theoretical) of colorless fine crystalline product, 99% pure by Gas Chromatography Mass Spectrometry gave a parent ion at 180 amu. Structure confirmed by X-ray crystallography (see FIG. 1) GCMS.

$^1$H NMR: (500 MHz, $D_8$THF): δ=1.23 (s, 9H), δ=1.3 (s, 9H), δ=6.48 (s, 1H), δ=10 (bs, 1H).

$^1$H NMR: (500 MHz, $D_8$THF): δ=30.3 (s, 3C), δ=30.8 (s, 3C), δ=32.1 (s, 1C), δ=33.6 (s, 1C), δ=111 (bs, 1C), δ=148 (bs, 1C), δ=155 (s, 1C).

X-ray

Example 2

Synthesis of 2,2,5,5-Tetramethyl-3-hexanone 2-chloro-2-methylpropane (75 g, 0.8 mol) was slowly added to magnesium pellets (19.5 g, 0.8 mol) in 800 mL of THF to make the Grignard reagent, tBuMgCl. This was added slowly to a mixture of cuprous chloride (49.5 g, 0.50 mol) and tertbutylacetylchloride (67.25 g, 0.50 mol), cooled to −50° C. in dry ice. After addition, the mixture was allowed to warm up to room temperature overnight. Most of the THF was removed by decreased pressure, followed by the addition of 500 mL of hexanes and 200 mL of 2M HCl. This mixture was filtered to remove the solid byproducts. The aqueous layer was washed 3× with 100 mL of hexanes, the hexanes layer washed 3× with 200 mL of 2M HCl, 2× with 200 mL of $NaHCO_3$/water, 1× with 200 mL of water, and finally 1× with 200 mL of NaCl/water. The product mixture was then dried for an hour in MgSO$_4$, which was subsequently removed by filtration. The hexane was then removed by atmospheric distillation.

Yield=61 g (78% of theoretical).
Product identified by Mass Spectrum parent ion of 156 mu, NMR consistent with literature: D. P Bauer, J. Org. Chem., Vol. 40, No. 13, 1975, 1990-1992.

Example 3

Synthesis of 4-Bromo-2,2,5,5-tetramethyl-3-hexanone 24 g of N-bromosuccinimide (0.1344 mol) was added to 10 g of 2,2,5,5-Tetramethyl-3-hexanone (0.064 mol) in 50 mL of trimethylacetonitrile. To this mixture, 10 g of ammonium acetate (0.1344 mol) was added within 5 minutes. This mixture was refluxed overnight then filtered. To the filtrate, 24 g of N-bromosuccinimide (0.1344 mol) and 10 g of ammonium acetate (0.1344 mol) was added, then refluxed for 5 hours. The reaction mixture was then cooled, 600 mL of water added, and the resulting mixture then filtered. The aqueous layer was washed three times with 50 ml of hexanes. The hexane fractions were then combined, washed three times with 50 ml of with water, then dried with anhydrous magnesium sulfate. Product was collected by distilling off the hexane at atmospheric pressure.

Yield 11.6 g, (77% of theoretical)
Product identified by Mass Spectrum parent ion of 236 mu, NMR consistent with literature: D. P Bauer, J. Org. Chem., Vol. 40, No. 13, 1975, 1990-1992; Procedure Reference: K. Tanemura, Chem. Commun. 2004, 470-471.

Example 4

Synthesis of 4-hydroxy-2,2,5,5-tetramethyl-3-hexanone 5 g (0.125 mol) of sodium hydroxide powder was added to 11.6 g (0.05 mol) of 4-Bromo-2,2,5,5-tetramethyl-3-hexanone in 10 g of dry diethylformamide. This reaction mixture was heated to 110° C. for 2 hours, cooled to room temperature and 600 mL of water and 200 mL of hexanes added. The hexane layer was collected and the aqueous layer was washed three times with 50 ml of additional hexanes. The hexanes fractions were then combined, washed three times with 50 ml water, then dried with MgSO$_4$. The product was collected as a crystalline solid after hexanes removal by atmospheric distillation.

Yield=5.2 g, (60% of theoretical).
Product identified by Mass Spectrum Parent ion of 172 mu.

Example 5

Synthesis of 2,2,5,5-tetramethyl-3,4-hexandione 7.8 g (0.045 moles) of 2,2,5,5-tetramethyl-4-hydroxy-3-hexanone were dissolved in 90 ml of hexane and stirred vigorously with 157 ml of 1M aqueous potassium permanganate solution containing 1.8 g (0.045 moles) of sodium hydroxide. This mixture was then refluxed overnight. The mixture was then cooled to room temperature and the hexane layer separated. The aqueous layer was then extracted three times with 50 ml of hexane. The hexane solutions were then combined and washed three times with 50 ml of pure water before drying over anhydrous magnesium sulfate. The mixture was then filtered and the hexane distilled off at atmospheric pressure to yield 6.3 g of 2,2,5,5-tetramethyl-3,4-hexanedione (82% of theoretical).

Product identified by GCMS parent ion 170 mu, consistent with literature results G. A. Olah and A. Wu, J. Org. Chem., 56, 904-906 (1991).

Example 6

Synthesis of 2,4,5-tri-tert-butylimidazole 1.6 g (0.0094 moles) of 2,2,5,5-tetramethyl-3,4-hexanedione were mixed with 2.9 g (0.037 moles) of ammonium acetate, 3.4 g (0.057 moles) of acetic acid and 1.6 g (0.019 moles) of pivaldehyde and heated to 13° C. for 72 hrs in a sealed container. This mixture was then cooled and slowly added to an excess of aqueous saturated sodium bicarbonate solution. The resulting mixture was extracted with 3×50 ml of hexane. The hexane fractions were combined, washed three time with 20 ml aliquots of pure water, then dried over anhydrous sodium sulfate. Evaporation of hexane yielded crude 2,4,5-tri-tert-butylimidazole as its hydrate (two molecules of imidazole per water molecule). This product was then dried by refluxing it in 50 ml of hexamethyldisilazane for 48 hrs.

The hexamethyldisilazane and hexamethyldisiloxane (formed from the drying process) was then evaporated, and the resulting solid sublimed at 60 C to give colorless crystals, yield 1.3 g (58% of theoretical).

$^1$H NMR: (500 MHz, C$_6$D$_6$): δ=1.24(s, 9H), δ=1.26(s, 9H), δ=1.65(s, 9H), δ=8.07(bs, 1H).
$^{13}$C NMR: (500 MHz, C$_6$D$_6$): δ=30.0 (s, 3C), δ=31.70 (s, 1C), δ=32.26 (s, 3C), δ=32.87 (s, 1C), δ=33.18 (s, 3C), δ=34.07 (s, 1C), δ=130.16(s, 1C), δ=143.84 (s, 1C), δ=149.21(s, 1C).

Figure 2:
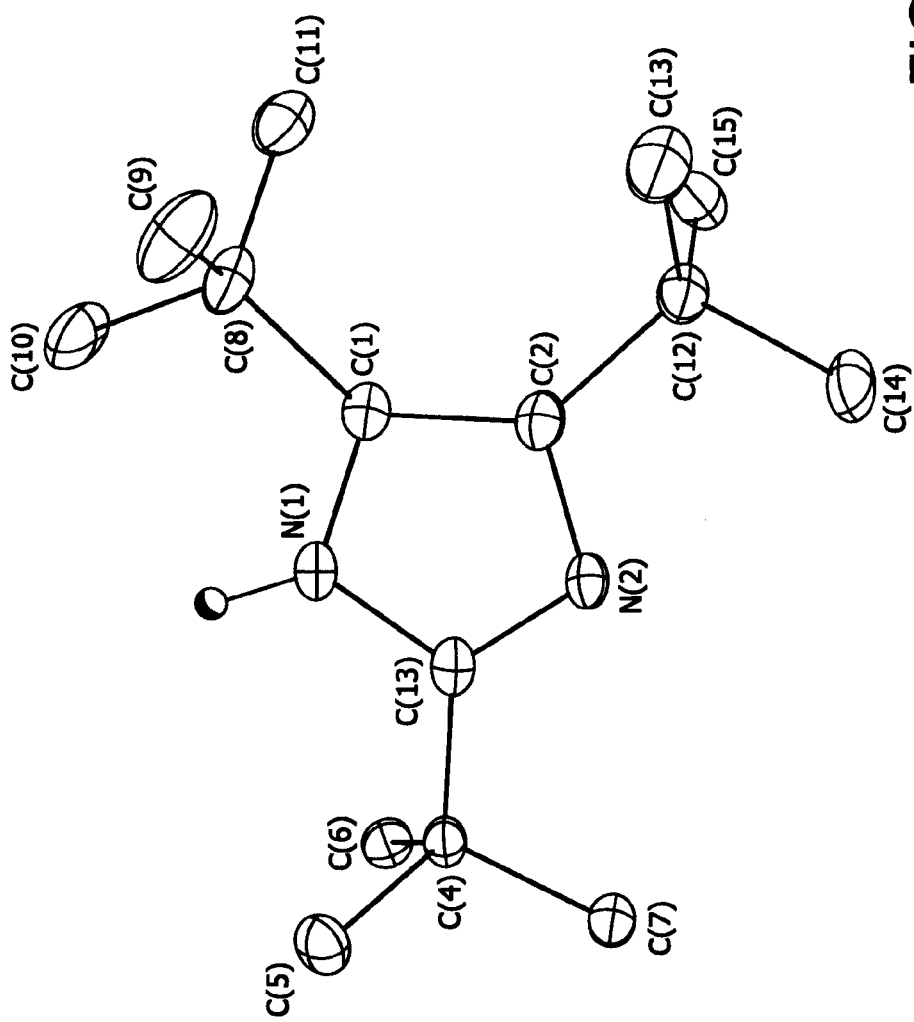
FIG. 2 is an illustration of the X-ray structure of 2,4,5-tri-tert-butylimidazole (hydrogen atoms are not illustrated for purposes of clarity except on N(1)).

Mass spectrum: 236 mu (parent ion).
Structure of the of 2,4,5-tri-tert-butylimidazole was also confirmed by X-ray crystallography, see FIG. 2.

In addition to the synthesis routes of this disclosure that are used to prepare sterically hindered imidazoles, a plurality of other routes are anticipated. These include conceptually deconstructing the five membered imidazole ring by breaking specific ring bonds to yield fragments bearing the required bulky groups. A synthesis of these fragments is then developed followed by a means of coupling them together to form the final imidazole product.

Example 7

Synthesis of barium bis(2,4,5-tri-tert-butylimidazolate)(tetrahydrofuran)

Figure 3:
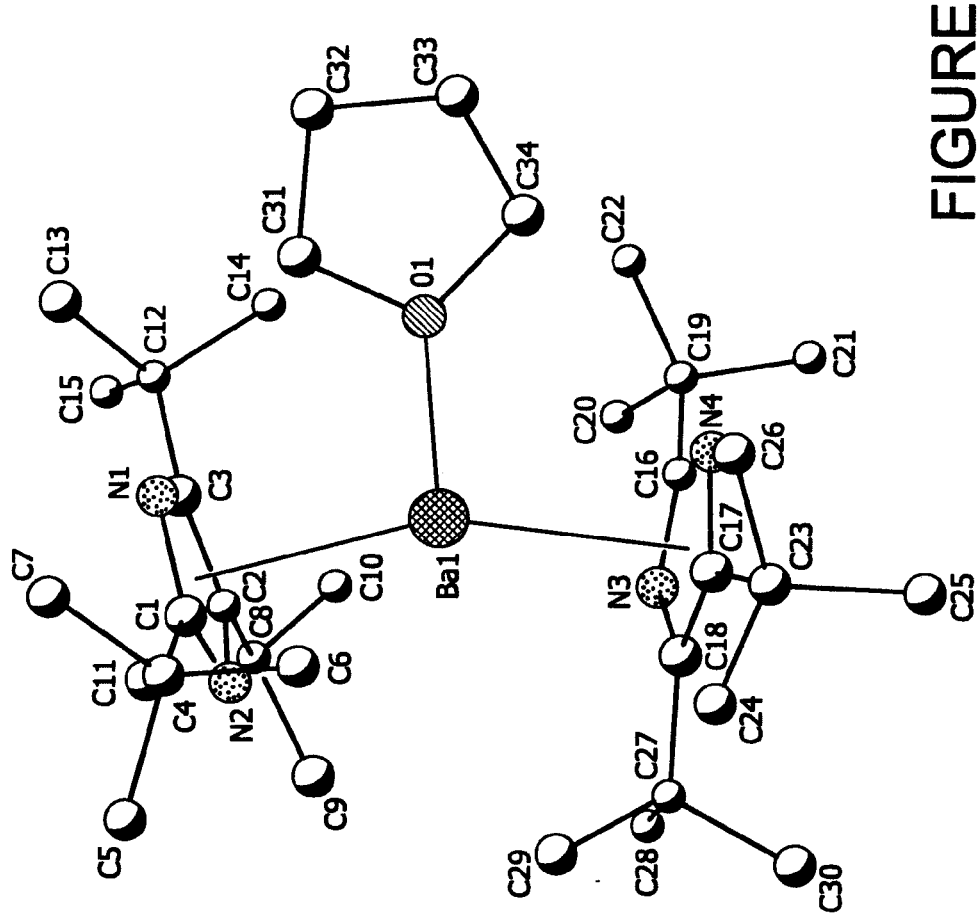
FIG. 3 is an illustration of the structure of barium bis(2,4,5-tri-tert-butylimidazolate)(tetrahydrofuran) (hydrogen atoms are not illustrated for purposes of clarity).

Under an atmosphere of nitrogen, 0.292 g (0.00124 moles) of dry 2,4,5-tri-tert-butylimidazole were dissolved into 5 ml of dry tetrahydrofuran with stirring. To this was added a solution of 0.37 g (0.00062 moles) of barium bis(hexamethyldisilazane)bis (tetrahydrofuran) dissolved in 5 ml of tetrahydrofuran. This mixture was stirred for 3 hours at room temperature. The tetrahydrofuran and by product hexamethyldisilazane were then evaporated by application of vacuum and the resulting white solid dissolved into 1 ml of dry hexane. The resulting solution was then concentrated by boiling to 0.5 ml and allowed to stand at room temperature. This yielded 0.3 g (83% of theoretical) of barium bis(2,4,5-tri-tert-butylimidazolate)(tetrahydrofuran) as colorless prisms. Structure confirmed by single crystal X-ray diffraction, see FIG. 3.

$^1$H NMR: (500 MHz, C$_6$D$_6$): δ=1.29 (m, 4H), δ=1.49 (s, 18H), δ=1.59 (m, 36H), δ=3.82 (m, 4H).
$^{13}$C NMR: (500 MHz, C$_6$D$_6$): δ=25.72 (s, 2C), δ=30.1 (s, 1C), δ=31.5 (s, 3C), δ=33.7 (s, 6C), δ=34.26 (s, 2C), δ=69.95 (s, 2C), δ=147.75 (s, 1C), δ=159.77 (s, 1C).

Example 8

Synthesis of di-barium tetra(2,4,5-tri-tert-butylimidazolate)

Under an atmosphere of nitrogen, 1.18 g (0.005 moles) of 2,4,5-tri-tert-butylimidazole were dissolved in 10 ml of dry hexane and 0.4 g (0.0025 moles) of bis[2-(N,N-dimethylamino)ethyl]ether. To this mixture, a solution of 1.5 g (0.0025 moles) of barium bis(hexamethyldisilazane)bis(tetrahydrofuran) dissolved in 10 ml of dry hexane was added dropwise and the mixture stirred overnight. The solvents were then removed under vacuum and the resulting solid sublimed twice at 160° C. to yield 0.6 g (47% of theoretical) of snow white solid, melting point (MPt) 150° C., characterized by X-ray crystallography, see FIG. 4.

The evaporation characteristics of di-barium tetra(2,4,5-tri-tert-butylimidazolate) was determined by TGA resulting in only 3.5 weight % residue, as shown in FIG. 5.

$^1$H NMR: (500 MHz, C$_6$D$_6$): δ=1.46 (6, 36H), δ=1.50 (s, 18H)

Example 9

Synthesis of di-strontium tetra(2,4,5-tri-tert-butlyimidazolate)

Under an atmosphere of nitrogen, 1.18 g (0.005 moles) of 2,4,5-tri-tert-butylimidazole were dissolved in 10 ml of dry tetrahydrofuran. 1.38 g (0.0025 moles) of strontium bis(hexamethyldisilazane)bis(tetrahydrofuran) were then dissolved in 10 ml of dry tetrahydrofuran and this solution was added dropwise, with stirring, to the 2,4,5-tri-tert-butylimidazole solution and the resulting mixture stirred overnight. The solvents were then removed under vacuum and the resulting solid sublimed twice at 150 C to yield 0.5 g (36% of theoretical) of snow white solid, MPt 149° C., characterized by X-ray crystallography, see FIG. 6.

Example 10

Synthesis of 3,3,6,6-tetramethyl-4,5-octanedione

Under a blanket of nitrogen, 18.72 g, (0.78 moles) of magnesium turnings in 780 ml of tetrahydrofuran were activated by the addition of 0.5 ml of 1,2-dibromoethane.

2-chloro-2-methyl butane (96 mL, 0.78 mol) were then slowly added resulting in the gradual formation of Grignard reagent, accompanied by a reaction exotherm. This Grignard reagent was then slowly added to a mixture of 112 g (0.78 mol) of copper bromide and 67 g (0.78 mol) of lithium bromide dissolved in 340 mL of terahydrofuran, cooled to −65° C. After all the Grignard was added and the temperature stabilized at −65° C., 26 mL (0.30 mol) of oxalyl chloride in 100 mL of tetrahydrofuran was added slowly, maintaining mixture temperature at −65° C. The resulting mixture was stirred for an hour at −65° C., then warmed up to room temperature overnight. 90% of the tetrahydrofuran THF was then removed by vacuum. 500 ml of hexane and 300 mL of saturated aqueous ammonium chloride were then added to the resultant slurry, and the hexane layer separated. The aqueous layer was then further extracted with three 200 ml lots of hexane. The combined hexane layers were then washed with 200 mL of water, then dried over 10 g of anhydrous magnesium sulfate for one hour. The magnesium sulfate was then filtered off and the hexane distilled off at atmospheric pressure to yield the crude product diketone as an orange red liquid. Yield=32.2 g (54% of theoretical)

Mass spectrum: 198 mu (parent ion).

Example 11

Synthesis of 2-tert-butyl-4,5-di-(1,1-dimethylpropyl)imidazole

A mixture of 32.3 g (0.163 mol) of 3,6,6-tetramethyl-4,5-octanedione, 50 g (0.652 mol) of ammonium acetate, 36 mL(0.326 mol) of pivaldehyde and 56 mL (0.978 mol) of acetic acid was heated to 200° C. in a sealed stainless steel vessel for 3 days. The resulting product mixture was neutralized with sodium bicarbonate solution, then extracted with four 200 ml lots of hexane. The combined hexane layers were washed 3× with 100 mL of water then 100 ml of saturated sodium chloride solution. 10 g of anhydrous magnesium sulfate was added and stirred overnight. Filtration followed by removal of hexane by vacuum yielded the crude product as a yellow oil. Yield 31.5 g (73% of theoretical).

Mass spectrum: 264 mu (parent ion).

Example 12

Synthesis of di-strontium tetra(2-tert-butyl-4,5-di-(1,1-dimethylpropyl)imidazolate)

Under a blanket of nitrogen, 1.13 g ((0.002 moles) of strontium bis(hexamethyldisiylamide)bis(tetrahydrofuran) dissolved in 20 ml of dry tetrahydrofuran were added dropwise over a five minute period at room temperature to 1.08 g (0.004 moles) of 2-tert-butyl-4,5-di-(1,1-dimethylpropyl) imidazole dissolved in 20 ml of dry tetrahydrofuran and the resulting mixture stirred for two hours. The THF and by-product hexamethyldisilazane were then removed under vacuum. The resulting crude product was then distilled under vacuum at 20° C. to yield 0.5 g of a colorless glassy solid. This was recrystallized in hexane to yield colorless prisms, MPt 103C.

Yield=40% of theoretical.

$^1$H NMR: (500 MHz, C$_6$D$_6$): δ=0.82(t, 12H), δ=1.41(s, 24H), δ=1.54(s, 18H), δ=1.74 (q, 8H). Structure confirmed by single crystal X-ray analysis, see FIG. 8.

Example 13

Synthesis of di-barium tetra(2-tert-butyl-4,5-di-(1,1-dimethylpropyl)imidazolate)

Under an atmosphere of dry nitrogen, a solution of 6.0 g (0.01 moles) of barium bis(hexamethyldisilazane)bis(tetrahydrofuran) dissolved in 15 ml of dry tetrahydrofuran were added dropwise to 5.28 g (0.02 moles) of 2-tert-butyl-4,5-di-(1,1-dimethylpropyl)imidazole dissolved in 30 ml of dry tetrahydrofuran. The resulting mixture was stirred overnight, after which the solvent and hexamethyldisilazane were removed by vacuum. The resulting waxy solid was then vacuum distilled at to 195° C. to give a clear colorless liquid distillate of di-barium tetra(2-tert-butyl-4,5-di(1,1-dimethylpropyl) imidazolate), which solidified after standing overnight. Yield 4.8 g (78%). Structure proven by X-ray, FIG. 10. MPt 65.3° C.

$^1$H NMR: (500 MHz, $C_6D_6$): δ=0.85 (t, 12H), δ=1.39 (s, 24H), δ=1.53 (s, 18H), δ=1.76-1.81(q, 8H).

Example 14

2-(1,1-dimethylbutyl)-4,5-di-tert-butylimidazole 15 g (0.09 moles) of 2,2,5,5-tetramethyl-3,4-hexanedione were mixed with 42 g (0.55 moles) of ammonium acetate, 32 g (0.53 moles) of acetic acid and 20.52 g (0.18 moles) of 2,2-dimethylvaleraldehyde and heated to 20° C. for 48 hrs in a sealed container. This mixture was then cooled to 90° C., and approximately 90% of the acetic acid distilled off under reduced pressure. The residual crude product was then diluted with approximately 100 ml of hexane and neutralized to pH 7 using saturated aqueous sodium bicarbonate solution with strong stirring. The resulting mixture was extracted with 3×200 ml of hexane. The hexane fractions were combined, washed three times with 50 ml aliquots of pure water, then dried over anhydrous sodium sulfate. After overnight stirring, the solution was then decanted off the magnesium sulfate and then stood over molecular sieves overnight. The molecular sieves were then removed, the hexane distilled off at atmospheric pressure, and the resulting product then distilled at 150° C. under 100 mTorr of pressure. Yield=13.5 g (57% of theoretical) of 2-(1,1-dimethylbutyl)-4,5-di-tert-butylimidazole.

$^1$H NMR: (500 MHz, $C_6D_6$): δ=0.79(t, 3H), δ=1.19-1.23 (m, 2H), δ=1.24(s, 9H), δ=1.26(s, 9H), δ=1.53-1.57(m, 2H), δ=1.65(s, 6H).

Example 15

Di-strontium-tetra(2-(1,1-dimethylbutyl)-4,5-di-tert-butylimidazolate)

Under an atmosphere of dry nitrogen, a solution of 5.54 g (0.01 moles) of strontium bis(hexamethyldisilazane)bis(tetrahydrofuran) dissolved in 15 ml of dry tetrahydrofuran were added dropwise to 5.06 g (0.019 moles) of 2-tert-butyl-4,5-di-(1,1-dimethylbutyl)imidazole dissolved in 30 ml of dry tetrahydrofuran. The resulting mixture was stirred for 12 days at room temperature, after which the solvent and hexamethyldisilazane were removed by vacuum. The resulting crude product was vacuum distilled at 100 mTorr, collecting the main fraction of di-strontium-tetra(2-(1,1-dimethylbutyl)-4,5-di-tert-butylimidazolate) from 150 to 205° C. as a clear liquid, which solidified into a glass at room temperature, slowly crystallizing overnight. Yield 3.5 g (60% of theoretical). Structure proven by single crystal X-ray diffraction using a crystal grown from a hexane solution, see FIG. 13. TGA/DSC showed a melting point of 99.8° C. and an involatile residue of 8.17 wt %.

$^1$H NMR: (500 MHz, $C_6D_6$): δ=0.91 (t, 6H), δ=1.27-1.32 (m, 4H), δ=1.45 (s, 36H), δ=1.54 (s, 12H), 1.75-1.80 (m, 4H).

Example 16

Di-barium-tetra(2-(1,1-dimethylbutyl)-4,5-di-tert-butylimidazolate)

Under an atmosphere of dry nitrogen, a solution of 6.03 g (0.01 moles) of barium bis(hexamethyldisilazane)bis(tetrahydrofuran) dissolved in 15 ml of dry tetrahydrofuran were added dropwise to 5.28 g (0.019 moles) of 2-(1,1-dimethylbutyl)-4,5-di-tert-butylimidazole dissolved in 30 ml of dry tetrahydrofuran. The resulting mixture was stirred for 7 days at room temperature, after which the solvent and hexamethyldisilazane were removed by vacuum. The resulting crude product vacuum distilled at 50 mTorr, collecting the main fraction of di-strontium-tetra(2-(1,1-dimethylbutyl)-4,5-di-tert-butylimidazolate) from 170 to 180° C. as a clear liquid, which crystallized upon cooling to room temperature. Yield 4.8 g (72% of theoretical). Structure proven by single crystal X-ray diffraction using a crystal grown from a hexane solution, see FIG. 15. TGA/DSC showed a melting point of 128° C. and an involatile residue of only 2.99 wt %.

$^1$H NMR: (500 MHz, $C_6D_6$): δ=0.92(t, 6H), δ=1.28-1.4(m, 4H), δ=1.46(s, 36H), δ=1.5(s, 12H), δ=1.73-1.82(m, 4H).

Example 17

Synthesis of 2-(1,1-dimethylbutyl)-4,5-di-(1,1-dimethylpropyl)imidazole 20 g (0.1 moles) of 3,3,6,6-tetramethyl-4,5-octanedione were mixed with 46 g (0.6 moles) of ammonium acetate, 30 g (0.6 moles) of acetic acid and 11.4 g (0.1 moles) of 2,2-dimethylvaleraldehyde and heated to 200° C. for 48 hrs in a sealed container. This mixture was then cooled to 90° C., and approximately 90% of the acetic acid distilled off under reduced pressure. The residual crude product was then diluted with approximately 100 ml of hexane and neutralized to pH 7 using saturated aqueous sodium bicarbonate solution with strong stirring. The resulting mixture was extracted with 3×200 ml of hexane. The hexane fractions were combined, washed three times with 50 ml aliquots of pure water, then dried over anhydrous sodium sulfate. After overnight stirring, the solution was then decanted off the magnesium sulfate, and dried molecular sieves were added. After overnight standing the molecular sieves were removed, the hexane distilled off at atmospheric pressure, and the resulting product then distilled at 150° C. under 100 mTorr of pressure. Yield=15 g (51% of theoretical) of 2-(1,1-dimethylbutyl)-4,5-di-(1,1-dimethylpropyl)imidazole.

$^1$H NMR: (500 MHz, $C_6D_6$): δ=0.69(t, 3H), δ=0.82(t, 3H), δ=1.0(t, 3H), δ=1.15-1.2(m, 2H). δ=1.19(s, 6H), δ=1.25(s, 6H), δ=1.52-1.60(m, 4H), δ=1.59(s, 6H), δ=1.96-2.0(q, 2H), δ=8.0(bs, 1H).

Example 18

Synthesis of distrontium tetra(2-(1,1-dimethylbutyl)-4,5-di-(1,1-dimethylpropyl) imidazolate)

Under an atmosphere of dry nitrogen, a solution of 7.46 g (0.0135 moles) of strontium bis(hexamethyldisilazane)bis (tetrahydrofuran) dissolved in 50 ml of dry tetrahydrofuran were added dropwise to 7.88 gg (0.0269 moles) of 2-(1,1-dimethylbutyl)-4,5-di-(1,1-dimethylpropyl)imidazole dissolved in 50 ml of dry tetrahydrofuran. The resulting mixture was stirred for 2 days at room temperature, after which the solvent and hexamethyldisilazane were removed by vacuum. The resulting crude product vacuum distilled at 50 mTorr, collecting the main fraction of di-strontium-tetra(2-(1,1-dimethylbutyl)-4,5-di-(1,1-dimethylpropyl)imidazolate)

$^1$H NMR: (500 MHz, $C_6D_6$): δ=0.77(t, 12H), δ=0.87(t, 6H), δ=1.1-1.23(m, 4H), δ=1.38 (s, 24H), δ=1.51 (s, 12H), δ=1.62-1.75 (m, 12H).

Example 19

Synthesis of dibarium tetra(2-(1,1-dimethylbutyl)-4, 5-di-(1,1-dimethylpropyl)imidazolate)

Under an atmosphere of dry nitrogen, a solution of 7.0 g (0.0116 moles) of barium bis(hexamethyldisilazane)bis(tetrahydrofuran) dissolved in 50 ml of dry tetrahydrofuran were added dropwise to 8.11 g (0.0277 moles) of 2-(1,1-dimethylbutyl)-4,5-di-(1,1-dimethylpropyl)imidazole (19% excess) dissolved in 50 ml of dry tetrahydrofuran. The resulting mixture was stirred for 2 days at room temperature, after which the solvent and hexamethyldisilazane were removed by vacuum. The product and excess 2-(1,1-dimethylbutyl)-4,5-di-(1,1-dimethylpropyl)imidazole were then vacuum distilled out of the crude reaction product at 200° C./50 mTorr. The excess imidazole ligand was then removed by vacuum distillation at 120° C. to yield di-barium tetra(2-(1,1-dimethylbutyl)-4,5-di-(1,1-dimethylpropyl)imidazolate) as a thick viscous amber liquid, which slowly crystallized upon standing. Mpt 36° C., yield 5.6 g (62%). Recrystallization from hexane yielded colorless crystals, MPt 56.4° C., TGA residue 6.77 wt %. $^1$H NMR: (500 MHz, $C_6D_6$): δ=0.84(t, 12H), δ=0.93(t, 6H), δ=1.22-1.35(m, 4H), δ=1.39 (s, 24H), δ=1.53 (s, 12H), δ=1.7-1.8 (m, 12H)

Example 20

Synthesis of barium bis(2,4,5-tri-phenylylimidazolate)

Under an atmosphere of dry nitrogen, 0.6 g (0.002 moles) of 2,4,5-triphenylimidazole were dissolved in 10 ml of dry tetrahydrofuran. A solution of 0.6 g (0.001 moles) of barium bis(hexamethyldisilazane)bis(tetrahydrofuran) dissolved in 10 ml of dry tetrahydrofuran was then prepared and added to the 2,4,5-triphenylimidazole solution and the resulting mixture stirred overnight. The solvent and hexamethyldisilazane were then removed under vacuum, yielding a thick viscous tar, which eventually solidified. Application of vacuum and heat >200° C. did not liberate any volatile products.

Example 21

ALD of Strontium oxide using di-strontium tetra(2-tert-butyl-4,5-di(1,1-dimethylpropyl) imidazolate)

Figure 18:
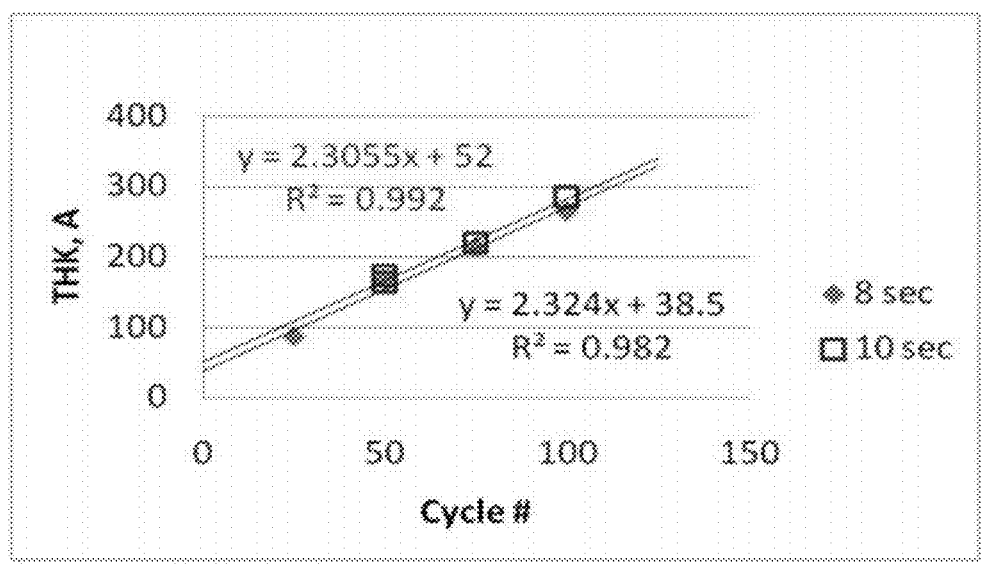
FIG. 18 illustrates the ALD strontium oxide film thickness as a function of the number of ALD cycles for the precursor di-strontium tetra(2-tert-butyl-4,5-di-(1,1-dimethylpropyl) imidazolate) reacted with ozone.
Figure 21:
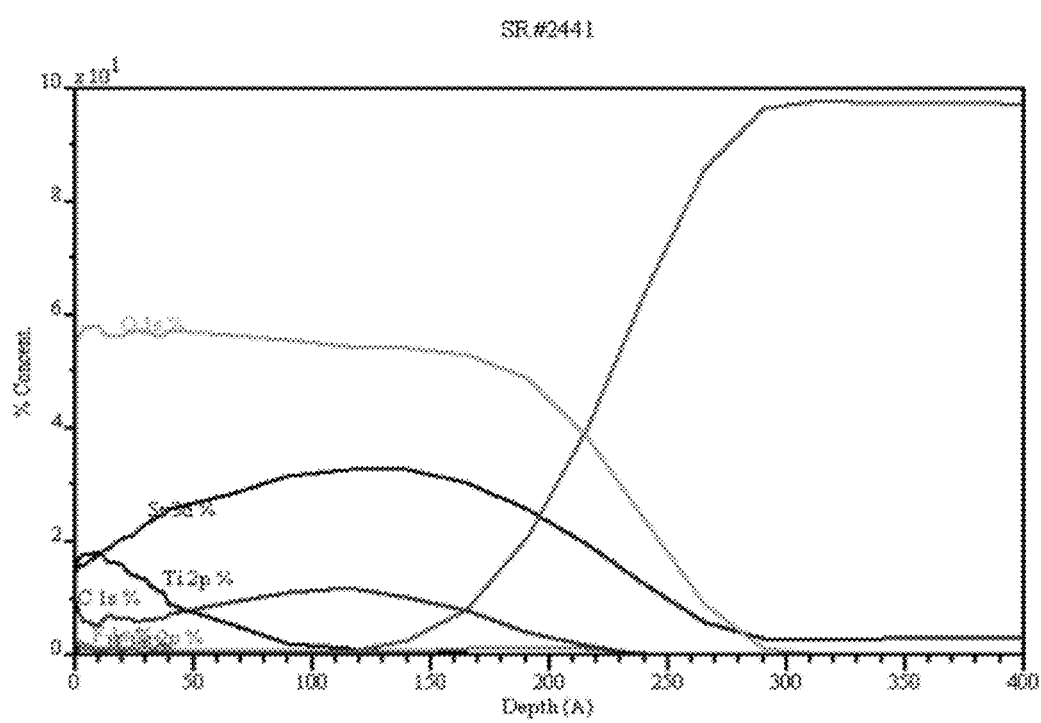
FIG. 21 illustrates the X-ray Photoelectron Spectroscopy (XPS) analysis of an SrO film grown at 350° C. using di-strontium tetra(2-tert-butyl-4,5-di-(1,1-dimethylpropyl)imidazolate)/ozone.

Under an atmosphere of nitrogen, 50 g of di-strontium tetra(2-tert-butyl-4,5-di-(1,1-dimethylpropyl)imidazolate) were loaded into a dry stainless steel container. This container was then heated to 170° C., and argon carrier gas was intermittently flowed through it at a rate of 100 sccm to achieve ALD 'pulses' of the precursor, varying from 6 to 16 seconds. These precursor pulses were directed into an ALD chamber containing a silicon substrate heated from 300-400° C. Each precursor pulse was followed by a purging pulse of argon gas, then followed with a pulse of ozone. FIG. 18 shows the results achieved for SrO deposition at 350° C. substrate temperature using 8 and 10 second precursor pulses, which shows a linear ALD relationship between film growth and total number of precursor pulses, giving a growth rate of 2.3A/cycle of SrO. Using this same deposition procedure at a substrate temperature of 375° C. yielded the SrO film shown in FIG. 20, the upper portion of which is clearly crystalline and the lower portion of which is amorphous. Note that a titanium oxide protective layer is deposited on top of the SrO. In the crystalline region, it is seen that there are 24 layers of SrO per 66 Angstroms, to yield a spacing of 2.75 Angstroms, consistent with (001) SrO. XPS, shown in FIG. 21, which indicates the film to be substantially pure strontium oxide. The low level of carbon throughout the film is partially attributable to post deposition reaction with atmospheric carbon dioxide to yield strontium carbonate.

Example 22

ALD Thermal Stability Demonstration for di-strontium tetra(2-tert-butyl-4,5-di-tert-amylimidazolate)

100 cycles of 5 seconds precursor/10 seconds argon purge using argon, as in Example 15, but no ozone was used to oxidize adsorbed precursor. Substrates were processed from 250-400° C. As FIG. 22 shows, there is no significant thermal deposition occurring until >350° C., indicating excellent stability for ALD.

The invention claimed is:

1. A compound comprising a structure selected from the group consisting of:

Formula E

Formula F

Formula G and

-continued

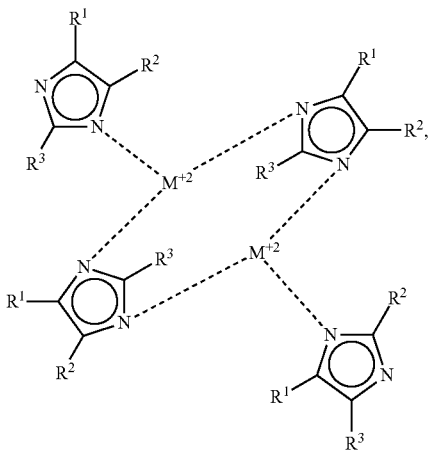

Formula H wherein
R¹, R², R³ and are each individually bulky groups selected from the group consisting of: $C_1$-$C_{10}$ tertiary alkyl; $C_1$-$C_{10}$ tertiary alkoxy; $C_1$-$C_{10}$ tertiary alkylamine; $C_1$-$C_{10}$ tertiary alkyl functionalized with a heteroatom substituted ring structure; $C_1$-$C_{10}$ tertiary alkyl functionalized with an amide group; $C_1$-$C_{10}$ tertiary alkyl functionalized with an ester group, and mixtures thereof;

(L) is a neutral ligand selected from the group consisting of aliphatic $C_3$-$C_{20}$ ether or polyether, crown ether, amine, poly amine, amide, poly amide, ester, polyester, aromatic ether, aromatic ester, aromatic amide, aromatic amine, pyridine, imidazole, pyridine, pyrazine, furan, pyrrole, and mixtures thereof;

n=0-4; and

M=Ba, Sr, Ca, Ra, Mg, or mixtures thereof.

2. The compound of claim 1 wherein the imidazolates anions coordinate to M in a manner selected from the group consisting of: eta-1, eta-2, eta-3, eta-4 and eta-5 mode.

3. The compound of claim 1 selected from the group consisting of: Di-barium tetra(2,4,5-tris-t-butylimidazolate); Di-barium tetra(2-tert-butyl-4,5-di-(1,1-dimethylpropyl)imidazolate); Di-barium tetra(2-(1,1-dimethylbutyl)-4,5-di-tert-butylimidazolate); and Di-barium tetra(2-(1,1-dimethylbutyl)-4,5-di-(1,1-dimethylpropyl)imidazolate).

4. The compound of claim 1 selected from the group consisting of: Di-strontium tetra(2,4,5-tris-t-butylimidazolate); Di-strontium tetra(2-tert-butyl-4,5-di-(1,1-dimethylpropyl) imidazolate); Di-strontium tetra(2-(1,1-dimethylbutyl)-4,5-di-tert-butylimidazolate); and, Di-strontium tetra(2-(1,1-dimethylbutyl)-4,5-di-(1,1-dimethylpropyl)imidazolate).

5. The compound of claim 1 wherein R¹, R², and R³ of each imidazolate anion are the same bulky group.

6. The compound of claim 1 wherein at least one of R¹, R², and R³ of one imidazolate anion is joined to at least one of the R¹, R², and R³ of another imidazolate anion to connect the two imidazolate anions.

7. The compound of claim 1 in a stainless steel container.

* * * * *